United States Patent [19]
Paulson et al.

[11] Patent Number: 5,962,294
[45] Date of Patent: *Oct. 5, 1999

[54] COMPOSITIONS AND METHODS FOR THE IDENTIFICATION AND SYNTHESIS OF SIALYLTRANSFERASES

[75] Inventors: James C. Paulson, Sherman Oaks; Xiaohong Wen; Brian Livingston, both of San Diego; William Gillespie, Culver City, all of Calif.; Sorge Kelm, Kiel, Germany; Alma L. Burlingame, Sausalito; Katalin Medzihradszky, San Francisco, both of Calif.

[73] Assignees: The Regents of the University of California, Oakland; Amgen, Inc., Thousand Oaks, both of Calif.

[ * ] Notice: This patent is subject to a terminal disclaimer.

[21] Appl. No.: 08/102,385

[22] Filed: Aug. 4, 1993

Related U.S. Application Data

[63] Continuation-in-part of application No. 07/925,369, Aug. 4, 1992, abandoned, which is a continuation-in-part of application No. 07/850,357, Mar. 9, 1992, abandoned.

[51] Int. Cl.$^6$ ...................................................... C12N 9/10
[52] U.S. Cl. ..................... 435/193; 435/69.1; 435/252.3; 536/23.1; 536/22.1; 536/23.2; 536/23.5
[58] Field of Search ..................................... 435/193, 69.1, 435/252.3, 240.2; 536/22.1, 23.1, 23.2, 23.5

[56] References Cited

PUBLICATIONS

Sadler et al., "Purification to Homogeneity of a beta–Galactoside alpha2–3 Sialytransferase . . . ", Journal of Biological Chemistry, vol. 254, No. 11, pp. 4434–4443 (1979).

Weinstein et al., "Purification of a Galbeta 1–4GlcNAc alpha2–6 Sialytransferase . . . ", Journal of Biological Chemistry, vol. 267, No. 22, pp. 13835–13844 (1962).

Nemansky et al., "Human liver and human placenta both contain CMP–NeuAc:Galbeta 1–4GlcNAc–R alpha2–3 . . . ", FEBS vol. 312, No. 1 pp. 31–36 Nov. (1992).

Mathews et al., "Mass Spectrometrically Derived . . . ", Journal of Biological Chemistry, vol. 262, No. 16, pp. 7537–7545 (1987).

Lee et al., "Generation of cDNA Probed Directed by Amino Acid Sequence . . . ", Science vol. 239, pp. 1288–1291 (1988).

Primary Examiner—Robert A. Wax
Assistant Examiner—Enrique D. Longton
Attorney, Agent, or Firm—Oppenheimer Wolff & Donnelly LLP

[57] ABSTRACT

DNA isolates coding for sialyltransferase which contain a conserved region of homology and methods of obtaining such DNA are provided, together with expression systems for recombinant production of sialyltransferase.

4 Claims, 16 Drawing Sheets

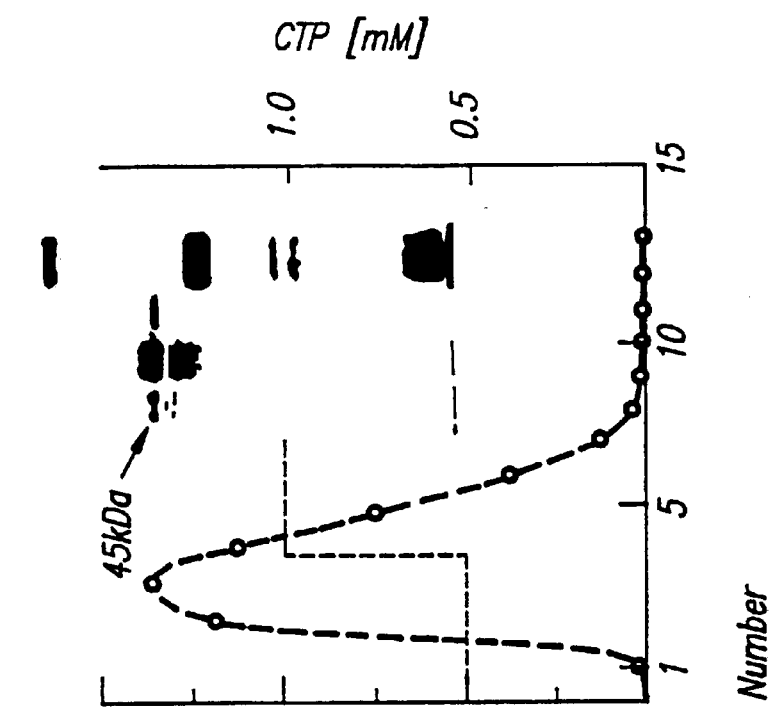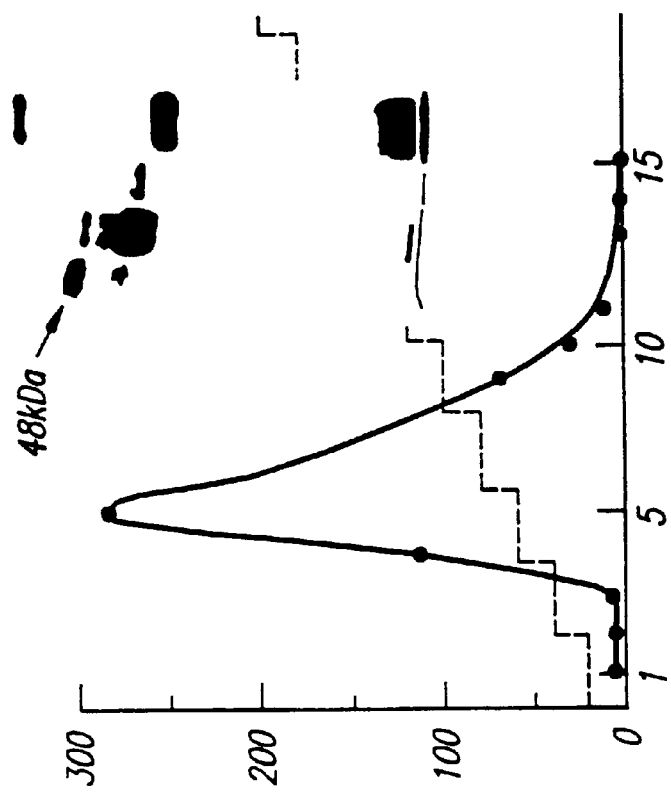
FIG. 4B
FIG. 4A

48 kDa peptide sequence

NH₂-Ser-Thr-Leu-Lys-Leu-His-Thr-Leu-Leu-Val- 10
11 Leu-Phe-Ile-Phe-Leu-Thr-Ser-Phe-Phe-Leu- 20
21 Asn-Tyr-COOH

45 kDa peptide sequence

NH₂-Lys-Tyr-Pro-Tyr-Arg-Pro-Thr-Thr-Thr-Thr- 10
11 Arg-Ile-Ile-Glu-Gln-Lys-Val-Ser-Ala- 20
21 Phe-Phe-COOH

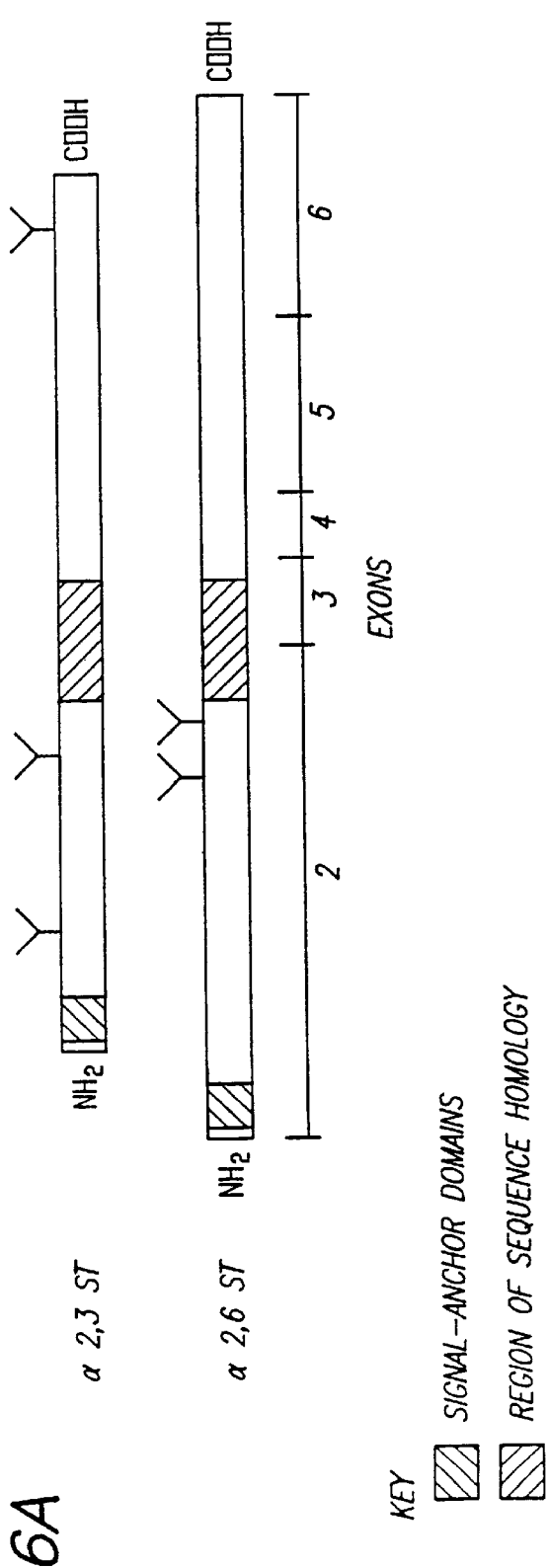

FIG. 12

(Sequence alignment of ST3N, ST3O, ST6N)

```
ST3N  Cys Arg Arg Cys Ile Ile Val Gly Asn Gly Val Leu Ala Asn Lys Ser Leu Gly Ser Arg
ST3O  Cys Arg Arg Cys Ala Val Val Gly Ser Gly Asn Leu Lys Glu Ser Tyr Tyr Gly Pro Gln
ST6N  Tyr Gln Arg Cys Ala Val Val Ser Ser Ala Gly Ser Leu Lys Asn Ser Gln Leu Gly Arg Glu

ST3N  Ile Asp Asp Tyr Asp Ile Val Leu Arg Leu Asn Ser Ala Pro Val Lys Gly Phe Glu Lys Asp
ST3O  Ile Asp Ser His Asp Phe Val Leu Arg Met Asn His Asp Ala Val Leu Arg Phe Gly Ala Pro Thr Asp
ST6N  Ile Asp Asn His Asp Phe Val Leu Arg Phe Ala Leu Arg Asn Gly Gln

ST3N  Val Gly Ser Lys Thr Thr Leu Arg Ile Thr Tyr Pro Glu
ST3O  Val Gly Ser Lys Thr Thr His His Phe Val Tyr Pro Glu
ST6N  Val Gly Ser Lys Thr Thr Ile Arg Leu Met Asn Ser Gln
```

FIG. 13

```
                      1                                                         55
Consensus    c b r C a x V g n s G v l k n s . l G . e I D . h d f V I R . N . A P t . q f e . D V G s K T t t r . m n p a 2,3(O)-ST    C R R C A V V G N S G N L K E S Y Y G P Q I D S H D F V L R H N K A P T E G F E A D V G S K T T H H F V Y P E
2,3(N)-ST    C R R C I I V G N G G V L A N K S L G S R I D D Y D I V I R L N S A P V K G F E K D V G S K T T L R I T T P E
2,6(N)-ST  W Q R C A V V S S A G S L K N S Q L G R E I D N H D A V L R F W G A P T D N F Q Q D V G S K T T I R L M N S Q
                                                                  *                    *  *
SH1          P Q T C A I V G N S G V L L N S G C G Q E I D T H S F V I R C N L A P V Q E Y A R D V G L K T D L V T M N P S
                *
```

FIG. 14

```
  1 ATG CAG CTG CAG TTC CGG AGC TGG ATG CTG GCC GCG CTC ACG CTG CTG GTG GTG TTC CTC ATC TTC GCA GAC ATC TCA GAG ATC GAA GAA  90
  1 Met Gln Leu Gln Phe Arg Ser Trp Met Leu Ala Ala Leu Thr Leu Leu Val Val Phe Leu Ile Phe Ala Asp Ile Ser Glu Ile Glu Glu  30
 91 GAA ATC GGG AAT TCT GGA GGC AGA GGT ACA ATC AGA TCA GCT GTG AAC AGC TTA CAT AGC AAA TCT AAT AGA GCT GAA GTT GTA ATA AAT 180
 31 Glu Ile Gly Asn Ser Gly Gly Arg Gly Thr Ile Arg Ser Ala Val Asn Ser Leu His Ser Lys Ser Asn Arg Ala Glu Val Val Ile Asn  60
181 GGC TCT TCA CTA CCA GCC GTT GCT AGA AGT AAT GAC AGC CTT AAG CAC AGC ATC CAG CCA GCC ATC AGC TCC AAG TGG AGA CAC AAC CAG 270
 61 Gly Ser Ser Leu Pro Ala Val Ala Arg Ser Asn Asp Ser Leu Lys His Ser Ile Gln Pro Ala Ser Ser Lys Trp Arg His Asn Gln  90
271 ACG CTC TCT CTG AGG ATC AGG AAG CAA ATT TTA AAG GAT GCA GAG AAG GAT ATT TCT GTC CTT AAG GGG ACC CTG AAG CCT GGA 360
 91 Thr Leu Ser Leu Arg Ile Arg Lys Gln Ile Leu Lys Asp Ala Glu Lys Asp Ile Ser Val Leu Lys Gly Thr Leu Lys Pro Gly 120
361 GAC ATT ATT CAT CAT CGA GAC AGC ACA ATG AAC CTC TCC CAG AAC CTC TAT GAA CTC CTC CCC AGA ACC TCA CCT CTG AAG 450
121 Asp Ile Ile His His Arg Asp Ser Thr Met Asn Leu Ser Gln Asn Leu Tyr Glu Leu Leu Pro Arg Thr Ser Pro Leu Lys 150
451 AAT AAG CAT TTC CAG ACT TGC GCC ATC GTG GGC AAC TCA GGA GTC TTG CTC AAC AGC GGT GTG CTA AAT AGC GGG TGT GGG GAG ATT 540
151 Asn Lys His Phe Gln Thr Cys Ala Ile Val Gly Asn Ser Gly Val Leu Leu Asn Ser Gly Cys Gly Gln Glu Ile Asp Thr His Ser Phe 180
541 GTC ATA AGG TGC AAC CTG GCT CAG GTT CCA GTT CAG GAG TAT GCC AAG GAT GTG GCC CTA AGG AAC ACT GAC GTG ACC CCC TCA GTC ATC 630
181 Val Ile Arg Cys Asn Leu Ala Pro Val Gln Glu Tyr Ala Arg Asp Val Gly Leu Lys Thr Asp Leu Val Thr Met Asn Pro Ser Val Ile 210
631 CAG CGG GCC TTT GAG GAC GTA GTG AAT GCC ACG TGG CGA GAG GAG AAG CTA CTG CAG CTG CAT CGG CTC AAT GGG AGC ATA CTG TGG ATA 720
211 Gln Arg Ala Phe Glu Asp Val Val Asn Ala Thr Trp Arg Glu Glu Lys Leu Leu Gln Leu His Arg Leu Asn Gly Ser Ile Leu Trp Ile 240
721 CCT GCC TTC ATG ATG GCC CGG GGT GGC AAG GAG TGG GTG GTC AAT GCT CTC ATC CTG AAT GTC AAT GCT CGC ACA GCT TAC 810
241 Pro Ala Phe Met Met Ala Arg Gly Gly Lys Glu Trp Val Asn Ala Leu Ile Leu Asn Val Arg Thr Ala Tyr 270
811 CCT TCC CTG CGC CTG CTG CAC CGA GTC CGA GGA TAT TGG CTG ACC AAC AAC ATC AAA AGA CCA ACC ACT GGC CTC CTG ATG TAC 900
271 Pro Ser Leu Arg Leu Leu His Arg Val Arg Gly Tyr Trp Leu Thr Asn Lys Val His Ile Lys Arg Pro Thr Thr Gly Leu Leu Met Tyr 300
901 ACC CTG GCC ACA CGC TTC TGC AAT CAG ATC TAC CTT TAT GGC TTG CCC TTC CCA TTG GAT CAG AAT CAG AAC CCC GTC AAG TAC CAC 990
301 Thr Leu Ala Thr Arg Phe Cys Asn Gln Ile Tyr Leu Tyr Gly Leu Pro Phe Pro Leu Asp Gln Asn Gln Asn Pro Val Lys Tyr His 330
991 TAT TAT GAC AGC CTC AAG TAT CGC TAC ACC TCC CAG GCC ATG CCC CTT GAA TTC AAG GCC CTC AAG AGC CTA CAT GAA 1080
331 Tyr Tyr Asp Ser Leu Lys Tyr Gly Tyr Thr Ser Gln Ala Ser Pro His Thr Met Pro Leu Glu Phe Lys Ala Leu Lys Ser Leu His Glu 360
1081 CAG GGG GCA TTG AAA CTG ACT GTC GGC CAG TGT GAC GGG GCT ACG TAA
 361 Gln Gly Ala Leu Lys Leu Thr Val Gly Gln Cys Asp Gly Ala Thr STOP
```

FIG.15

|     |                                                        |       |
| --- | ------------------------------------------------------ | ----- |
| 1   | MGLLVFVRNLLLALCLFLVLGFLYYSAWKLHLLQWEEDSNSVVLSFDSAG      | Human |
|     | ‖‖‖‖‖‖‖‖‖‖‖‖‖‖‖‖‖‖‖‖‖‖‖‖‖‖  ‖‖‖‖‖                      |       |
| 1   | MGLLVFVRNLLLALCLFLVLGFLYYSAWKLHLLQWE-DSNSLILSLDSAG      | Rat   |
| 51  | QTLGSEYDRLIGFLLNLDSKLPAELATKYANFSEGACKPGYASALMTAIFP     | Human |
|     | ‖‖‖‖‖‖‖‖‖‖‖‖‖‖‖‖‖‖‖‖‖‖‖‖‖‖‖‖‖‖‖‖‖‖‖‖‖‖‖‖‖‖ ‖‖‖‖‖‖     |       |
| 50  | QTLGTEYDRLIGFLLKLDSKLPAELATKYANFSEGACKPGYASAMMTAIFP     | Rat   |
| 101 | RFSKPAPMFLDDSFRKWARIREFVPPFGIKGQDNLIKAILSVTKEYRLTP      | Human |
|     | ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖      |       |
| 100 | RFSKPAPMFLDDSFRKWARIREFVPPFGIKGQDNLIKAILSVTKEYRLTP      | Rat   |
| 151 | ALDSLRCRRCIIVGNGGVLANKSLGSRIDDYDIVVRLNSAPVKGFEKDVG      | Human |
|     | ‖‖‖‖‖ ‖‖‖‖‖‖‖‖‖‖‖‖‖‖‖‖‖‖‖‖‖‖‖‖‖‖ ‖‖‖‖‖‖‖‖‖‖‖‖‖‖‖‖     |       |
| 150 | ALDSLHCRRCIIVGNGGVLANKSLGSRIDDYDIVIRLNSAPVKGFEKDVG      | Rat   |
| 201 | SKTTLRITYPEGAMQRPEQYERDSLFVLAGFKWQDFKWLKYIVYKERVSA      | Human |
|     | ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖      |       |
| 200 | SKTTLRITYPEGAMQRPEQYERDSLFVLAGFKWQDFKWLKYIVYKERVSA      | Rat   |
| 251 | SDGFWKSVATRVPKEPPEIRILNPYFIQEAAFTLIGLPFNNGLMGRGNIP      | Human |
|     | ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖      |       |
| 250 | SDGFWKSVATRVPKEPPEIRILNPYFIQEAAFTLIGLPFNNGLMGRGNIP      | Rat   |
| 301 | TLGSVAVTMALHGCDEVAVAGFGYDMSTPNAPLHYYETVRMAAIKESWTH      | Human |
|     | ‖‖‖‖‖‖‖‖‖‖ ‖‖‖‖‖‖‖‖‖‖‖‖‖‖ ‖‖‖‖‖‖‖‖‖‖‖‖‖‖‖‖‖‖‖‖‖‖      |       |
| 300 | TLGSVAVTMALDGCDEVAVAGFGYDMNTPNAPLHYYETVRMAAIKESWTH      | Rat   |
| 351 | NIQREKEFLRKLIVKARVITDLSSGI                              | Human |
|     | ‖‖‖‖‖‖‖‖‖‖‖‖‖‖‖‖‖‖‖‖‖‖‖‖‖                              |       |
| 350 | NIQREKEFLRKLIVKARVITDLSSGI                              | Rat   |

```
MOTIF                                                          P          LE         R            D
ST3                    REDRYIEPFYFPIPEKKEPCLQEAESKASKLFGNYSRDQPIFLR LEEDYFWVKIP SAYELPYGTKGSE DL
ST3N    GQTLGSEYDRLGFLL NLDSKLPAELATKYANFSEGACKPGYASALMIAIFPRFSKPAPMF                LDDSFRKWARIRFFVPPFGIKGQD NL
ST30                            KYPYRPCTCTRCIEEQRVSAWFDERFNRSMQPLLTAKNAH LEEDTYKWVL RLQREKQPNNLND TI
ST6N    SKQPDKEDIPILSYHRVTAKVK PQPSFQWDKDSTYSKLNPRLLKIWRNYLNMNKYKVSYKGPGVKFSVEE LRCHL RDHVNVSMIEATDFPF

MOTIF          CRRC VVGN G L NS LG ID  D V R N AP  GFE DVGSKTT R  YPE                               D L
ST3     LLRVLATTSSSIP KNIQSLRCRRCVVVGNGHRLRNSSLGDAINKYDVVIRLNNAPVAGYEGDVGSKTTMRLFTPESAHFDPKVENNPDTLLVLAFK
ST3N    IKAILSVIKEYRLTPALDSLRCRRCIIVGNGGVLANKSLGSRIDDYDIVVRLNSAPVKGFEEKDVGSKTTLRLTTYPEGAMQRPE QYERDSLFVLAGFK
ST30    RELFQLVPGNVDPLLEKRLVSCRRCAVVGNSNLKESYYGPQIDSHDFVLRMNKAPTEGFEADVGSKTTHHFVYPESFRELAQEVSMILVPFKITDLE
ST6N    NTIEWEGYLPKENFRTK VGPWQRCAVVSSAGSLKNSOLGREIDNHDAVLRFNGAPTDNFQQDVGSKTTLRLMNSQLVTT   EKRFLKDSLYTEGILI

MOTIF                       I              F K                       I I P FI                P G L       LH CD V   GFG
ST3     AMDFHWIETILSDKKRV   RKGFWKQPPLIWDVNPKQIRILNPFEMELAADKLLSLPMQQPRKIKQK                 PTTGILAITLALHLCDIVHTAGFGYP
ST3N    WQDFKWLK YIVYKERVS ASDGFWKSVATRVPKEPPEIRILNPYFIQEAAFTLIGLPFNNGLMGRGNI                PTLGSVAVTMALHGCDEVAVAGFGY
ST30                    WVISAITTGTISHTYVPVPAKIKVKRE          KILIYHPAFIKYVFDRWLQGHGRY           PSTGILSVIFSLHICDEVDLYGEGA
ST6N    VWDPSVYHADIPKWYQL PDYNFFETYKSYR     RLNPSQPFYTLKPQMPWELWDIIQEISADLIQPNPPSSGMLGIIIMMTLCDQVDIYEFLPS

MOTIF          HY E     A        H E      L         I
ST3     D   DAYNKKQTIHYYEQITLKSMAGSG  HNVSQEALAIKRMLEMGAIKNLTSF
ST3N    DMSTPNAPLHYYETVRMAAIKESWT HNIQREKEFTLRKLVKARVITDLSSGI
ST30    D SKGN WHHYWENNPSAGAFRKTGVHDGDFESNVTTILASINKIRIFKGR
ST6N    KRKIDVCYYHQ KFFDSACTMGAY HPLLFEKNMVKHLDEGTDEDIYLFGLATLSGFRNIRC
```

FIG.18

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
        (A) LENGTH: 1218 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: porcine
        (F) TISSUE TYPE: liver, submaxillary glands (ix) FEATURE:
        (A) NAME/KEY: CDS
        (B) LOCATION: 91..1119

(D) OTHER INFORMATION: /product= "porcine Gal Beta 1,3
GalNAc alpha 2,3 sialyltransferase"

(xi) SEQUENCE DESCRIPTION: SEQ ID NO:1:

| | | | | | |
|---|---|---|---|---|---|
| CTTCTTGGGA GGTGCTCGTC CGTTAGGCGT GGGTTCCTGC ATCCCATCCC TGGGGTGCCC | | | | | 60 |

| | | | | | | | | | | | | | | | | |
|---|---|---|---|---|---|---|---|---|---|---|---|---|---|---|---|---|
| CTGCCCCGCG | CCCCGGCCGG | GGAGGCAGAC | ATG | GCC | CCC | ATG | AGG | AAG | AAG | AGC | | | | | | 114 |
| | | | Met | Ala | Pro | Met | Arg | Lys | Lys | Ser | | | | | | |
| | | | 1 | | | | 5 | | | | | | | | | |

| | | | | | | | | | | | | | | | | |
|---|---|---|---|---|---|---|---|---|---|---|---|---|---|---|---|---|
| ACC | CTC | AAG | CTG | CTC | ACG | CTC | CTG | GTC | CTC | TTC | ATC | TTC | CTC | ACC | TCC | 162 |
| Thr | Leu | Lys | Leu | Leu | Thr | Leu | Leu | Val | Leu | Phe | Ile | Phe | Leu | Thr | Ser | |
| | 10 | | | | 15 | | | | | 20 | | | | | | |

| | | | | | | | | | | | | | | | | |
|---|---|---|---|---|---|---|---|---|---|---|---|---|---|---|---|---|
| TTC | TTC | CTC | AAC | TAC | TCG | CAC | ACC | GTG | GTC | ACC | ACC | GCC | TGG | TTC | CCC | 210 |
| Phe | Phe | Leu | Asn | Tyr | Ser | His | Thr | Val | Val | Thr | Thr | Ala | Trp | Phe | Pro | |
| 25 | | | | | 30 | | | | | 35 | | | | | 40 | |

| | | | | | | | | | | | | | | | | |
|---|---|---|---|---|---|---|---|---|---|---|---|---|---|---|---|---|
| AAG | CAG | ATG | GTC | ATC | GAG | CTC | TCC | GAG | AAC | TTC | AAG | AAG | CTC | ATG | AAA | 258 |
| Lys | Gln | Met | Val | Ile | Glu | Leu | Ser | Glu | Asn | Phe | Lys | Lys | Leu | Met | Lys | |
| | | | | 45 | | | | | 50 | | | | | 55 | | |

| | | | | | | | | | | | | | | | | |
|---|---|---|---|---|---|---|---|---|---|---|---|---|---|---|---|---|
| TAC | CCC | TAC | AGG | CCC | TGC | ACC | TGC | ACC | CGC | TGC | ATC | GAA | GAG | CAG | AGG | 306 |
| Tyr | Pro | Tyr | Arg | Pro | Cys | Thr | Cys | Thr | Arg | Cys | Ile | Glu | Glu | Gln | Arg | |
| | | | 60 | | | | 65 | | | | | 70 | | | | |

| | | | | | | | | | | | | | | | | |
|---|---|---|---|---|---|---|---|---|---|---|---|---|---|---|---|---|
| GTC | TCC | GCC | TGG | TTC | GAT | GAG | CGA | TTC | AAC | CGG | TCC | ATG | CAG | CCG | CTG | 354 |
| Val | Ser | Ala | Trp | Phe | Asp | Glu | Arg | Phe | Asn | Arg | Ser | Met | Gln | Pro | Leu | |
| | | 75 | | | | | 80 | | | | | 85 | | | | |

| | | | | | | | | | | | | | | | | |
|---|---|---|---|---|---|---|---|---|---|---|---|---|---|---|---|---|
| CTG | ACG | GCC | AAG | AAC | GCG | CAC | CTG | GAG | GAA | GAC | ACT | TAC | AAG | TGG | TGG | 402 |
| Leu | Thr | Ala | Lys | Asn | Ala | His | Leu | Glu | Glu | Asp | Thr | Tyr | Lys | Trp | Trp | |
| | 90 | | | | 95 | | | | | 100 | | | | | | |

| | | | | | | | | | | | | | | | | |
|---|---|---|---|---|---|---|---|---|---|---|---|---|---|---|---|---|
| CTG | AGG | CTC | CAG | CGG | GAG | AAG | CAG | CCC | AAT | AAC | TTG | AAC | GAC | ACC | ATC | 450 |
| Leu | Arg | Leu | Gln | Arg | Glu | Lys | Gln | Pro | Asn | Asn | Leu | Asn | Asp | Thr | Ile | |
| 105 | | | | 110 | | | | | 115 | | | | | 120 | | |

| | | | | | | | | | | | | | | | | |
|---|---|---|---|---|---|---|---|---|---|---|---|---|---|---|---|---|
| AGG | GAG | CTG | TTC | CAG | GTG | GTG | CCT | GGG | AAC | GTG | GAC | CCC | CTG | CTG | GAG | 498 |
| Arg | Glu | Leu | Phe | Gln | Val | Val | Pro | Gly | Asn | Val | Asp | Pro | Leu | Leu | Glu | |
| | | | | 125 | | | | | 130 | | | | | 135 | | |

| | | | | | | | | | | | | | | | | |
|---|---|---|---|---|---|---|---|---|---|---|---|---|---|---|---|---|
| AAG | AGG | CTG | GTC | AGC | TGC | CGG | CGC | TGC | GCC | GTC | GTG | GGC | AAC | TCG | GGC | 546 |
| Lys | Arg | Leu | Val | Ser | Cys | Arg | Arg | Cys | Ala | Val | Val | Gly | Asn | Ser | Gly | |
| | | | 140 | | | | | 145 | | | | | 150 | | | |

| | | | | | | | | | | | | | | | | |
|---|---|---|---|---|---|---|---|---|---|---|---|---|---|---|---|---|
| AAC | CTG | AAG | GAG | TCC | TAC | TAT | GGG | CCT | CAG | ATA | GAC | AGC | CAC | GAC | TTC | 594 |
| Asn | Leu | Lys | Glu | Ser | Tyr | Tyr | Gly | Pro | Gln | Ile | Asp | Ser | His | Asp | Phe | |
| | | 155 | | | | | 160 | | | | | 165 | | | | |

| | | | | | | | | | | | | | | | | |
|---|---|---|---|---|---|---|---|---|---|---|---|---|---|---|---|---|
| GTG | CTG | AGG | ATG | AAC | AAG | GCC | CCC | ACG | GAG | GGG | TTT | GAG | GCC | GAC | GTC | 642 |
| Val | Leu | Arg | Met | Asn | Lys | Ala | Pro | Thr | Glu | Gly | Phe | Glu | Ala | Asp | Val | |
| | 170 | | | | 175 | | | | | 180 | | | | | | |

| | | | | | | | | | | | | | | | | |
|---|---|---|---|---|---|---|---|---|---|---|---|---|---|---|---|---|
| GGG | AGC | AAG | ACC | ACC | CAC | CAT | TTC | GTG | TAC | CCC | GAG | AGC | TTC | CGG | GAG | 690 |
| Gly | Ser | Lys | Thr | Thr | His | His | Phe | Val | Tyr | Pro | Glu | Ser | Phe | Arg | Glu | |
| 185 | | | | 190 | | | | | 195 | | | | | 200 | | |

| | | | | | | | | | | | | | | | | |
|---|---|---|---|---|---|---|---|---|---|---|---|---|---|---|---|---|
| CTG | GCG | CAG | GAG | GTC | AGC | ATG | ATC | CTG | GTC | CCC | TTC | AAG | ACC | ACC | GAC | 738 |
| Leu | Ala | Gln | Glu | Val | Ser | Met | Ile | Leu | Val | Pro | Phe | Lys | Thr | Thr | Asp | |
| | | | | 205 | | | | | 210 | | | | | 215 | | |

| | | | | | | | | | | | | | | | | |
|---|---|---|---|---|---|---|---|---|---|---|---|---|---|---|---|---|
| CTG | GAG | TGG | GTG | ATC | AGC | GCC | ACC | ACC | ACC | GGC | ACC | ATC | TCC | CAC | ACC | 786 |
| Leu | Glu | Trp | Val | Ile | Ser | Ala | Thr | Thr | Thr | Gly | Thr | Ile | Ser | His | Thr | |
| | | | 220 | | | | | 225 | | | | | 230 | | | |

| | | | | | | | | | | | | | | | | |
|---|---|---|---|---|---|---|---|---|---|---|---|---|---|---|---|---|
| TAC | GTT | CCT | GTC | CCC | GCC | AAG | ATC | AAA | GTC | AAA | AAG | GAG | AAG | ATC | CTG | 834 |
| Tyr | Val | Pro | Val | Pro | Ala | Lys | Ile | Lys | Val | Lys | Lys | Glu | Lys | Ile | Leu | |
| | | 235 | | | | | 240 | | | | | 245 | | | | |

| | | | | | | | | | | | | | | | | |
|---|---|---|---|---|---|---|---|---|---|---|---|---|---|---|---|---|
| ATT | TAT | CAC | CCG | GCC | TTC | ATC | AAG | TAC | GTC | TTC | GAC | AGG | TGG | CTG | CAG | 882 |
| Ile | Tyr | His | Pro | Ala | Phe | Ile | Lys | Tyr | Val | Phe | Asp | Arg | Trp | Leu | Gln | |
| | 250 | | | | 255 | | | | | 260 | | | | | | |

| | | | | | | | | | | | | | | | | |
|---|---|---|---|---|---|---|---|---|---|---|---|---|---|---|---|---|
| GGC | CAC | GGG | CGC | TAC | CCG | TCC | ACT | GGC | ATC | CTC | TCC | GTG | ATC | TTC | TCC | 930 |
| Gly | His | Gly | Arg | Tyr | Pro | Ser | Thr | Gly | Ile | Leu | Ser | Val | Ile | Phe | Ser | |
| 265 | | | | 270 | | | | | 275 | | | | | 280 | | |

| | | | | | | | | | | | | | | | | |
|---|---|---|---|---|---|---|---|---|---|---|---|---|---|---|---|---|
| CTG | CAC | ATC | TGT | GAC | GAG | GTG | GAC | TTG | TAT | GGC | TTT | GGG | GCG | GAC | AGC | 978 |

```
Leu His Ile Cys Asp Glu Val Asp Leu Tyr Gly Phe Gly Ala Asp Ser
            285                 290                 295

AAA GGG AAC TGG CAC CAC TAC TGG GAG AAC AAC CCT TCG GCG GGG GCT        1026
Lys Gly Asn Trp His His Tyr Trp Glu Asn Asn Pro Ser Ala Gly Ala
            300                 305                 310

TTC CGA AAG ACC GGG GTG CAC GAC GGG GAC TTC GAG TCC AAC GTG ACA        1074
Phe Arg Lys Thr Gly Val His Asp Gly Asp Phe Glu Ser Asn Val Thr
            315                 320                 325

ACC ATC TTG GCT TCC ATC AAC AAG ATC CGG ATC TTC AAG GGC AGA            1119
Thr Ile Leu Ala Ser Ile Asn Lys Ile Arg Ile Phe Lys Gly Arg
            330                 335                 340

TGACGCCGCG CAGGTTAAGG ACAGTTGCAG CAGCTCACCT CTCGACGTCC AGCCCCGGGA      1179

ACTTGGTGGC CCAGCCTCAG GGGTGTGCCC AGGTGCCCC                             1218

(2) INFORMATION FOR SEQ ID NO:2:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Pro Met Arg Lys Lys Ser Thr Leu Lys Leu Leu Thr Leu Leu
 1               5                  10                  15

Val Leu Phe Ile Phe Leu Thr Ser Phe Phe Leu Asn Tyr Ser His Thr
                20                  25                  30

Val Val Thr Thr Ala Trp Phe Pro Lys Gln Met Val Ile Glu Leu Ser
            35                  40                  45

Glu Asn Phe Lys Lys Leu Met Lys Tyr Pro Tyr Arg Pro Cys Thr Cys
        50                  55                  60

Thr Arg Cys Ile Glu Glu Gln Arg Val Ser Ala Trp Phe Asp Glu Arg
65                  70                  75                  80

Phe Asn Arg Ser Met Gln Pro Leu Leu Thr Ala Lys Asn Ala His Leu
                85                  90                  95

Glu Glu Asp Thr Tyr Lys Trp Trp Leu Arg Leu Gln Arg Glu Lys Gln
            100                 105                 110

Pro Asn Leu Asn Asp Thr Ile Arg Glu Leu Phe Gln Val Val Pro
        115                 120                 125

Gly Asn Val Asp Pro Leu Leu Glu Lys Arg Leu Val Ser Cys Arg Arg
    130                 135                 140

Cys Ala Val Val Gly Asn Ser Gly Asn Leu Lys Glu Ser Tyr Tyr Gly
145                 150                 155                 160

Pro Gln Ile Asp Ser His Asp Phe Val Leu Arg Met Asn Lys Ala Pro
                165                 170                 175

Thr Glu Gly Phe Glu Ala Asp Val Gly Ser Lys Thr Thr His His Phe
            180                 185                 190

Val Tyr Pro Glu Ser Phe Arg Glu Leu Ala Gln Glu Val Ser Met Ile
        195                 200                 205

Leu Val Pro Phe Lys Thr Thr Asp Leu Glu Trp Val Ile Ser Ala Thr
    210                 215                 220

Thr Thr Gly Thr Ile Ser His Thr Tyr Val Pro Val Pro Ala Lys Ile
225                 230                 235                 240

Lys Val Lys Lys Glu Lys Ile Leu Ile Tyr His Pro Ala Phe Ile Lys
                245                 250                 255

Tyr Val Phe Asp Arg Trp Leu Gln Gly His Gly Arg Tyr Pro Ser Thr
```

```
                260                 265                 270
Gly Ile Leu Ser Val Ile Phe Ser Leu His Ile Cys Asp Glu Val Asp
            275                 280                 285

Leu Tyr Gly Phe Gly Ala Asp Ser Lys Gly Asn Trp His His Tyr Trp
    290                 295                 300

Glu Asn Asn Pro Ser Ala Gly Ala Phe Arg Lys Thr Gly Val His Asp
305                 310                 315                 320

Gly Asp Phe Glu Ser Asn Val Thr Thr Ile Leu Ala Ser Ile Asn Lys
                325                 330                 335

Ile Arg Ile Phe Lys Gly Arg
            340
```

(2) INFORMATION FOR SEQ ID NO:3:

(i) SEQUENCE CHARACTERISTICS:
        (A) LENGTH: 1206 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Rattus norvegicus
        (F) TISSUE TYPE: liver (ix) FEATURE:
        (A) NAME/KEY: CDS
        (B) LOCATION: 83..1207
        (D) OTHER INFORMATION: /product= "rat Gal Beta
            1,3(4)GlcNAc alpha 2,3 sialyltransferase"

(xi) SEQUENCE DESCRIPTION: SEQ ID NO:3:

```
TGCCTTTCCC GGGGCCAGAT CCTCTTCGGA GCGACCGGGT CAGTTTGTCA AAGTCATGTA      60

GGAAATTGTG GGTCATGTGA AG ATG GGA CTC TTG GTA TTT GTA CGC AAC CTG      112
                        Met Gly Leu Leu Val Phe Val Arg Asn Leu
                          1               5                  10

CTG CTA GCC CTC TGC CTC TTT CTG GTC CTG GGA TTT TTG TAT TAT TCT      160
Leu Leu Ala Leu Cys Leu Phe Leu Val Leu Gly Phe Leu Tyr Tyr Ser
            15                  20                  25

GCC TGG AAG CTA CAC TTA CTC CAA TGG GAA GAC TCC AAT TCA CTG ATT      208
Ala Trp Lys Leu His Leu Leu Gln Trp Glu Asp Ser Asn Ser Leu Ile
        30                  35                  40

CTT TCC CTT GAC TCC GCT GGA CAA ACC CTA GGC ACA GAG TAT GAT AGG      256
Leu Ser Leu Asp Ser Ala Gly Gln Thr Leu Gly Thr Glu Tyr Asp Arg
    45                  50                  55

CTG GGT TTC CTC CTG AAG CTG GAC TCT AAA CTG CCT GCA GAG CTG GCC      304
Leu Gly Phe Leu Leu Lys Leu Asp Ser Lys Leu Pro Ala Glu Leu Ala
60                  65                  70

ACC AAG TAC GCT AAC TTT TCC GAG GGA GCC TGC AAA CCC GGC TAC GCT      352
Thr Lys Tyr Ala Asn Phe Ser Glu Gly Ala Cys Lys Pro Gly Tyr Ala
 75                  80                  85                  90

TCA GCC ATG ATG ACT GCC ATC TTC CCC AGG TTC TCC AAG CCA GCA CCC      400
Ser Ala Met Met Thr Ala Ile Phe Pro Arg Phe Ser Lys Pro Ala Pro
                95                 100                 105

ATG TTC CTG GAT GAC TCC TTT CGC AAA TGG GCT AGG ATT CGG GAG TTT      448
Met Phe Leu Asp Asp Ser Phe Arg Lys Trp Ala Arg Ile Arg Glu Phe
            110                 115                 120

GTG CCA CCC TTT GGG ATC AAA GGT CAA GAC AAT CTG ATC AAA GCC ATC      496
Val Pro Pro Phe Gly Ile Lys Gly Gln Asp Asn Leu Ile Lys Ala Ile
        125                 130                 135

TTG TCA GTC ACC AAA GAA TAC CGC CTG ACC CCT GCC TTG GAC AGC CTC      544
Leu Ser Val Thr Lys Glu Tyr Arg Leu Thr Pro Ala Leu Asp Ser Leu
```

| | | | | | | | | | | | | | | | | |
|---|---|---|---|---|---|---|---|---|---|---|---|---|---|---|---|---|
| | | 140 | | | | | 145 | | | | | 150 | | | | |
| CAC | TGC | CGC | CGC | TGC | ATC | ATC | GTA | GGC | AAT | GGA | GGG | GTC | CTC | GCC | AAC | 592 |
| His | Cys | Arg | Arg | Cys | Ile | Ile | Val | Gly | Asn | Gly | Gly | Val | Leu | Ala | Asn | |
| 155 | | | | | 160 | | | | | 165 | | | | | 170 | |
| AAG | TCT | CTG | GGG | TCA | CGA | ATT | GAC | GAC | TAT | GAC | ATT | GTG | ATC | AGA | TTG | 640 |
| Lys | Ser | Leu | Gly | Ser | Arg | Ile | Asp | Asp | Tyr | Asp | Ile | Val | Ile | Arg | Leu | |
| | | | | 175 | | | | | 180 | | | | | 185 | | |
| AAC | TCA | GCA | CCT | GTG | AAG | GGC | TTT | GAG | AAG | GAC | GTG | GGC | AGC | AAG | ACC | 688 |
| Asn | Ser | Ala | Pro | Val | Lys | Gly | Phe | Glu | Lys | Asp | Val | Gly | Ser | Lys | Thr | |
| | | | 190 | | | | | 195 | | | | | 200 | | | |
| ACC | CTG | CGC | ATC | ACC | TAC | CCT | GAA | GGT | GCC | ATG | CAG | CGG | CCT | GAG | CAA | 736 |
| Thr | Leu | Arg | Ile | Thr | Tyr | Pro | Glu | Gly | Ala | Met | Gln | Arg | Pro | Glu | Gln | |
| | | 205 | | | | | 210 | | | | | 215 | | | | |
| TAT | GAA | CGA | GAC | TCT | CTC | TTT | GTA | CTA | GCT | GGC | TTC | AAG | TGG | CAG | GAC | 784 |
| Tyr | Glu | Arg | Asp | Ser | Leu | Phe | Val | Leu | Ala | Gly | Phe | Lys | Trp | Gln | Asp | |
| | 220 | | | | | 225 | | | | | 230 | | | | | |
| TTC | AAG | TGG | CTG | AAG | TAC | ATC | GTC | TAC | AAG | GAG | AGA | GTG | AGC | GCA | TCC | 832 |
| Phe | Lys | Trp | Leu | Lys | Tyr | Ile | Val | Tyr | Lys | Glu | Arg | Val | Ser | Ala | Ser | |
| 235 | | | | | 240 | | | | | 245 | | | | | 250 | |
| GAT | GGC | TTC | TCG | AAG | TCC | GTG | GCC | ACC | CGA | GTG | CCC | AAG | GAG | CCC | CCT | 880 |
| Asp | Gly | Phe | Ser | Lys | Ser | Val | Ala | Thr | Arg | Val | Pro | Lys | Glu | Pro | Pro | |
| | | | | 255 | | | | | 260 | | | | | 265 | | |
| GAG | ATC | CGC | ATC | CTC | AAC | CCG | TAC | TTC | ATC | CAG | GAG | GCT | GCC | TTC | ACG | 928 |
| Glu | Ile | Arg | Ile | Leu | Asn | Pro | Tyr | Phe | Ile | Gln | Glu | Ala | Ala | Phe | Thr | |
| | | | 270 | | | | | 275 | | | | | 280 | | | |
| CTC | ATC | CGA | CTG | CCC | TTC | AAC | AAT | GGC | CTC | ATG | GGC | AGA | GGG | AAC | ATC | 976 |
| Leu | Ile | Arg | Leu | Pro | Phe | Asn | Asn | Gly | Leu | Met | Gly | Arg | Gly | Asn | Ile | |
| | | 285 | | | | | 290 | | | | | 295 | | | | |
| CCA | ACC | CTT | GGC | AGT | GTG | GCA | GTG | ACC | ATG | GCA | CTC | GAT | GGC | TGT | GAT | 1024 |
| Pro | Thr | Leu | Gly | Ser | Val | Ala | Val | Thr | Met | Ala | Leu | Asp | Gly | Cys | Asp | |
| | 300 | | | | | 305 | | | | | 310 | | | | | |
| GAA | GTG | GCA | GTC | GCG | GGC | TTT | GGC | TAT | GAC | ATG | AAC | ACA | CCC | AAC | GCC | 1072 |
| Glu | Val | Ala | Val | Ala | Gly | Phe | Gly | Tyr | Asp | Met | Asn | Thr | Pro | Asn | Ala | |
| 315 | | | | | 320 | | | | | 325 | | | | | 330 | |
| CCC | CTG | CAC | TAC | TAT | GAA | ACT | GTG | CGC | ATG | GCA | GCC | ATC | AAA | GAG | TCC | 1120 |
| Pro | Leu | His | Tyr | Tyr | Glu | Thr | Val | Arg | Met | Ala | Ala | Ile | Lys | Glu | Ser | |
| | | | | 335 | | | | | 340 | | | | | 345 | | |
| TGG | ACA | CAC | AAC | ATC | CAG | CGA | GAG | AAA | GAG | TTT | CTG | CGG | AAG | CTA | GTG | 1168 |
| Trp | Thr | His | Asn | Ile | Gln | Arg | Glu | Lys | Glu | Phe | Leu | Arg | Lys | Leu | Val | |
| | | | 350 | | | | | 355 | | | | | 360 | | | |
| AAA | GCA | CGC | GTC | ATC | ACT | GAC | TTA | AGC | AGT | GGT | ATC | TG | | | | 1206 |
| Lys | Ala | Arg | Val | Ile | Thr | Asp | Leu | Ser | Ser | Gly | Ile | | | | | |
| | | 365 | | | | | 370 | | | | | 375 | | | | |

(2) INFORMATION FOR SEQ ID NO:4:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Leu Leu Val Phe Val Arg Asn Leu Leu Ala Leu Cys Leu
  1             5                 10               15

Phe Leu Val Leu Gly Phe Leu Tyr Tyr Ser Ala Trp Lys Leu His Leu
            20                25              30

Leu Gln Trp Glu Asp Ser Asn Ser Leu Ile Leu Ser Leu Asp Ser Ala
         35                40              45

Gly Gln Thr Leu Gly Thr Glu Tyr Asp Arg Leu Gly Phe Leu Leu Lys

```
              50                  55                  60
Leu Asp Ser Lys Leu Pro Ala Glu Leu Ala Thr Lys Tyr Ala Asn Phe
65                  70                  75                  80

Ser Glu Gly Ala Cys Lys Pro Gly Tyr Ala Ser Ala Met Met Thr Ala
                85                  90                  95

Ile Phe Pro Arg Phe Ser Lys Pro Ala Pro Met Phe Leu Asp Asp Ser
            100                 105                 110

Phe Arg Lys Trp Ala Arg Ile Arg Glu Phe Val Pro Pro Phe Gly Ile
        115                 120                 125

Lys Gly Gln Asp Asn Leu Ile Lys Ala Ile Leu Ser Val Thr Lys Glu
    130                 135                 140

Tyr Arg Leu Thr Pro Ala Leu Asp Ser Leu His Cys Arg Arg Cys Ile
145                 150                 155                 160

Ile Val Gly Asn Gly Gly Val Leu Ala Asn Lys Ser Leu Gly Ser Arg
                165                 170                 175

Ile Asp Asp Tyr Asp Ile Val Ile Arg Leu Asn Ser Ala Pro Val Lys
            180                 185                 190

Gly Phe Glu Lys Asp Val Gly Ser Lys Thr Thr Leu Arg Ile Thr Tyr
        195                 200                 205

Pro Glu Gly Ala Met Gln Arg Pro Glu Gln Tyr Glu Arg Asp Ser Leu
    210                 215                 220

Phe Val Leu Ala Gly Phe Lys Trp Gln Asp Phe Lys Trp Leu Lys Tyr
225                 230                 235                 240

Ile Val Tyr Lys Glu Arg Val Ser Ala Ser Asp Gly Phe Ser Lys Ser
                245                 250                 255

Val Ala Thr Arg Val Pro Lys Glu Pro Pro Glu Ile Arg Ile Leu Asn
            260                 265                 270

Pro Tyr Phe Ile Gln Glu Ala Ala Phe Thr Leu Ile Arg Leu Pro Phe
        275                 280                 285

Asn Asn Gly Leu Met Gly Arg Gly Asn Ile Pro Thr Leu Gly Ser Val
    290                 295                 300

Ala Val Thr Met Ala Leu Asp Gly Cys Asp Glu Val Ala Val Ala Gly
305                 310                 315                 320

Phe Gly Tyr Asp Met Asn Thr Pro Asn Ala Pro Leu His Tyr Tyr Glu
                325                 330                 335

Thr Val Arg Met Ala Ala Ile Lys Glu Ser Trp Thr His Asn Ile Gln
            340                 345                 350

Arg Glu Lys Glu Phe Leu Arg Lys Leu Val Lys Ala Arg Val Ile Thr
        355                 360                 365

Asp Leu Ser Ser Gly Ile
    370

(2) INFORMATION FOR SEQ ID NO:5:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: porcine (xi) SEQUENCE DESCRIPTION: SEQ ID NO:5:

ACCCTGAAGC TGCGCACCCT GCTGGTGCTG TTCATCTTCC TGACCTCCTT CTT          53
```

(2) INFORMATION FOR SEQ ID NO:6:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (vi) ORIGINAL SOURCE:
        (A) ORGANISM: porcine (ix) FEATURE:
        (A) NAME/KEY: Region
        (B) LOCATION: 1..22
        (D) OTHER INFORMATION: /label= 48KDa
            /note= "amino terminal amino acid sequence of the
            porcine 48 KDa Gal Beta1,3 GalNAC alpha 2,3
            sialyltransferase"

(ix) FEATURE:
        (A) NAME/KEY: Domain
        (B) LOCATION: 5..20
        (D) OTHER INFORMATION: /note= "putative signal-anchor
            domain"

(xi) SEQUENCE DESCRIPTION: SEQ ID NO:6:

```
Ser Thr Leu Lys Leu His Thr Leu Leu Val Leu Phe Ile Phe Leu Thr
 1               5                  10                  15

Ser Phe Phe Leu Asn Tyr
            20
```

(2) INFORMATION FOR SEQ ID NO:7:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ATGCAGCTGC AGTTCCGGAG CTGGATGCTG GCCGCGCTCA CGCTGCTCGT GGTCTTCCTC    60

ATCTTCGCAG ACATCTCAGA GATCGAAGAA GAAATCGGGA ATTCTGGAGG CAGAGGTACA   120

ATCAGATCAG CTGTGAACAG CTTACATAGC AAATCTAATA GAGCTGAAGT TGTAATAAAT   180

GGCTCTTCAC TACCAGCCGT TGCTGACAGA AGTAATGAAA GCCTTAAGCA CAGCATCCAG   240

CCAGCCTCAT CCAAGTTGAG ACACAACCAG ACGCTCTCTC TGAGGATCAG GAAGCAAATT   300

TTAAAGTTCC TGGATGCAGA GAAGGATATT TCTGTCCTTA AGGGGACCCT GAAGCCTGGA   360

GACATTATTC ATTATATCTT TGATCGAGAC AGCACAATGA ACGTGTCCCA GAACCTCTAT   420

GAACTCCTCC CCAGAACCTC ACCTCTGAAG AATAAGCATT TCCAGACTTG TGCCATCGTG   480

GGCAACTCAG GAGTCTTGCT CAACACGGGC TGTGGGCAGG AGATTGACAC ACACAGCTTT   540

GTCATAAGGT GCAACCTGGC TCCAGTTCAG GAGTATGCCC GGGATGTGGG CCTCAAGACT   600

GACCTAGTGA CCATGAACCC CTCAGTCATC CAGCGGGCCT TGAGGACCT  AGTGAATGCC   660

ACGTGGCGGG AGAAGCTACT GCAGCGACTG CATGGCCTCA ATGGGACCAT ACTGTGGATA   720

CCTGCCTTCA TGGCCCGGGG TGGCAAGGAG CGTGTGGAGT GGGTCAATGC TCTCATCCTG   780

AAGCACCATG TCAACGTACG CACAGCTTAC CCTTCCCTGC GCCTGCTGCA CGCAGTCCGA   840

GGATATTGGC TGACCAACAA AGTCCACATC AAAAGACCAA CCACTGGCCT CCTGATGTAC   900

ACCCTGGCCA CACGCTTCTG CAATCAGATC TACCTTTATG GCTTCTGGCC CTTCCCATTG   960
```

```
GATCAGAATC AGAACCCCGT CAAGTACCAC TATTATGACA GCCTCAAGTA TGGCTACACC       1020

TCCCAGGCCA GCCCCCACAC CATGCCCTTG GAATTCAAGG CCCTCAAGAG CCTACATGAA       1080

CAGGGGGCAT TGAAACTGAC TGTCGGCCAG TGTGACGGGG CTACGTAA                   1128
```

(2) INFORMATION FOR SEQ ID NO:8:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gln Leu Gln Phe Arg Ser Trp Met Leu Ala Ala Leu Thr Leu Leu
 1               5                  10                  15

Val Val Phe Leu Ile Phe Ala Asn Ile Ser Glu Ile Glu Glu Glu Ile
             20                  25                  30

Gly Asn Ser Gly Gly Arg Gly Thr Ile Arg Ser Ala Val Asn Ser Leu
         35                  40                  45

His Ser Lys Ser Asn Arg Ala Glu Val Val Ile Asn Gly Ser Ser Leu
     50                  55                  60

Pro Ala Val Ala Asn Arg Ser Asn Glu Ser Leu Lys His Ser Ile Gln
 65                  70                  75                  80

Pro Ala Ser Ser Lys Trp Arg His Asn Gln Thr Leu Ser Leu Arg Ile
                 85                  90                  95

Arg Lys Gln Ile Leu Lys Phe Leu Asn Ala Glu Lys Asn Ile Ser Val
            100                 105                 110

Leu Lys Gly Thr Leu Lys Pro Gly Asn Ile Ile His Tyr Ile Phe Asn
        115                 120                 125

Arg Asn Ser Thr Met Asn Val Ser Gln Asn Leu Tyr Glu Leu Leu Pro
    130                 135                 140

Arg Thr Ser Pro Leu Lys Asn Lys His Phe Gln Thr Cys Ala Ile Val
145                 150                 155                 160

Gly Asn Ser Gly Val Leu Leu Asn Ser Gly Cys Gly Gln Glu Ile Asn
                165                 170                 175

Thr His Ser Phe Val Ile Arg Cys Asn Leu Ala Pro Val Gln Glu Tyr
            180                 185                 190

Ala Arg Asn Val Gly Leu Lys Thr Asn Leu Val Thr Met Asn Pro Ser
        195                 200                 205

Val Ile Gln Arg Ala Phe Glu Asn Leu Val Asn Ala Thr Trp Arg Glu
    210                 215                 220

Lys Leu Leu Gln Arg Leu His Gly Leu Asn Gly Ser Ile Leu Trp Ile
225                 230                 235                 240

Pro Ala Phe Met Ala Arg Gly Gly Lys Glu Arg Val Glu Trp Val Asn
                245                 250                 255

Ala Leu Ile Leu Lys His His Val Asn Val Arg Thr Ala Tyr Pro Ser
            260                 265                 270

Leu Arg Leu Leu His Ala Val Arg Gly Tyr Trp Leu Thr Asn Lys Val
        275                 280                 285

His Ile Lys Arg Pro Thr Thr Gly Leu Leu Met Tyr Thr Leu Ala Thr
    290                 295                 300

Arg Phe Cys Asn Gln Ile Tyr Leu Tyr Gly Phe Trp Pro Phe Pro Leu
305                 310                 315                 320

Asn Gln Asn Gln Asn Pro Val Lys Tyr His Tyr Tyr Asn Ser Leu Lys
                325                 330                 335
```

Tyr Gly Tyr Thr Ser Gln Ala Ser Pro His Thr Met Pro Leu Glu Phe
            340                 345                 350

Lys Ala Leu Lys Ser Leu His Glu Gln Gly Ala Leu Lys Leu Thr Val
        355                 360                 365

Gly Gln Cys Asn Gly Ala Thr
    370                 375

(2) INFORMATION FOR SEQ ID NO:9:

(i) SEQUENCE CHARACTERISTICS:
        (A) LENGTH: 1188 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:9:

ATGGGACTCT TGGTATTTGT GCGCAATCTG CTGCTAGCCC TCTGCCTCTT TCTGGTACTG        60

GGATTTTTGT ATTATTCTGC GTGGAAGCTA CACTTACTCC AGTGGGAGGA GGACTCCAAT       120

TCAGTGGTTC TTTCCTTTGA CTCCGCTGGA CAAACACTAG GCTCAGAGTA TGATCGGTTG       180

GGCTTCCTCC TGAATCTGGA CTCTAAACTG CCTGCTGAAT AGCCACCAA GTACGCAAAC        240

GGCTTCCTCC TGAATCTGGA CTCTAAACTG CCTGCTGAAT AGCCACCAA GTACGCAAAC        300

TTTTCAGAGG GAGCTTGCAA GCCTGGCTAT GCTTCAGCCT TGATGACGGC CATCTTCCCC       360

CGGTTCTCCA AGCCAGCACC CATGTTCCTG GATGACTCCT TTCGCAAGTG GCTAGAATC        420

CGGGAGTTCG TGCCGCCTTT TGGGATCAAA GGTCAAGACA ATCTGATCAA AGCCATCTTG       480

TCAGTCACCA AAGAGTACCG CCTGACCCCT GCCTTGGACA GCCTCCGCTG CCGCCGCTGC       540

ATCATCGTGG GCAATGGAGG CGTTCTTGCC AACAAGTCTC TGGGGTCACG AATTGACGAC       600

TATGACATTG TGGTGAGACT GAATTCAGCA CCAGTGAAAG GCTTTGAGAA GGACGTGGGC       660

AGCAAAACGA CACTGCGCAT CACCTACCCC GAGGGCGCCA TGCAGCGGCC TGAGCAGTAC       720

GAGCGCGATT CTCTCTTTGT CCTCGCCGGC TTCAAGTGGC AGGACTTTAA GTGGTTGAAA       780

TACATCGTCT ACAAGGAGAG AGTGAGTGCA TCGGATGGCT TCTGGAAATC TGTGGCCACT       840

CGAGTGCCCA AGGAGCCCCC TGAGATTCGA ATCCTCAACC CATATTTCAT CCAGGAGGCC       900

GCCTTCACCC TCATTGGCCT GCCCTTCAAC AATGGCCTCA TGGGCCGGGG GAACATCCCT       960

ACCCTTGGCA GTGTGGCAGT GACCATGGCA CTACACGGCT GTGACGAGGT GGCAGTCGCA      1020

GGATTTGGCT ATGACATGAG CACACCCAAC GCACCCCTGC ACTACTATGA GACCGTTCGC      1080

ATGGCAGCCA TCAAAGAGTC CTGGACGCAC AATATCCAGC GAGAGAAAGA GTTTCTGCGG      1140

AAGCTGGTGA AGCTCGCGT CATCACTGAT CTAAGCAGTG GCATCTGA               1188

(2) INFORMATION FOR SEQ ID NO:10:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO:10:

Met Gly Leu Leu Val Phe Val Arg Asn Leu Leu Leu Ala Leu Cys Leu
1               5                   10                  15

```
Phe Leu Val Leu Gly Phe Leu Tyr Tyr Ser Ala Trp Lys Leu His Leu
             20                  25                  30

Leu Gln Trp Glu Glu Asp Ser Asn Ser Val Val Leu Ser Phe Asp Ser
         35                  40                  45

Ala Gly Gln Thr Leu Gly Ser Glu Tyr Asp Arg Leu Gly Phe Leu Leu
     50                  55                  60

Asn Leu Asp Ser Lys Leu Pro Ala Glu Leu Ala Thr Lys Tyr Ala Asn
 65                  70                  75                  80

Phe Ser Glu Gly Ala Cys Lys Pro Gly Tyr Ala Ser Ala Leu Met Thr
                 85                  90                  95

Ala Ile Phe Pro Arg Phe Ser Lys Pro Ala Pro Met Phe Leu Asp Asp
                100                 105                 110

Ser Phe Arg Lys Trp Ala Arg Ile Arg Glu Phe Val Pro Pro Phe Gly
            115                 120                 125

Ile Lys Gly Gln Asp Asn Leu Ile Lys Ala Ile Leu Ser Val Thr Lys
        130                 135                 140

Glu Thr Arg Leu Thr Pro Ala Leu Asp Ser Leu Arg Cys Arg Arg Cys
145                 150                 155                 160

Ile Ile Val Gly Asn Gly Gly Val Leu Ala Asn Lys Ser Leu Gly Ser
                165                 170                 175

Arg Ile Asp Asp Tyr Asp Ile Val Val Arg Leu Asn Ser Ala Pro Val
            180                 185                 190

Lys Gly Phe Glu Lys Asp Val Gly Ser Lys Thr Thr Leu Arg Ile Thr
        195                 200                 205

Tyr Pro Glu Gly Ala Met Gln Arg Pro Glu Gln Tyr Glu Arg Asp Ser
    210                 215                 220

Leu Phe Val Leu Ala Gly Phe Lys Trp Gln Asp Phe Lys Trp Leu Lys
225                 230                 235                 240

Tyr Ile Val Tyr Lys Glu Arg Val Ser Ala Ser Asp Gly Phe Trp Lys
                245                 250                 255

Ser Val Ala Thr Arg Val Pro Lys Glu Pro Pro Glu Ile Arg Ile Leu
            260                 265                 270

Asn Pro Tyr Phe Ile Gln Glu Ala Ala Phe Thr Leu Ile Gly Leu Pro
        275                 280                 285

Phe Asn Asn Gly Leu Met Gly Arg Gly Asn Ile Pro Thr Leu Gly Ser
290                 295                 300

Val Ala Val Thr Met Ala Leu His Gly Cys Asp Glu Val Ala Val Ala
305                 310                 315                 320

Gly Phe Gly Tyr Asp Met Ser Thr Pro Asn Ala Pro Leu His Tyr Tyr
                325                 330                 335

Glu Thr Val Arg Met Ala Ala Ile Lys Glu Ser Trp Thr His Asn Ile
            340                 345                 350

Gln Arg Glu Lys Glu Phe Leu Arg Lys Leu Val Lys Ala Arg Val Ile
        355                 360                 365

Thr Asp Leu Ser Ser Gly Ile
370                 375

(2) INFORMATION FOR SEQ ID NO:11:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (xi) SEQUENCE DESCRIPTION: SEQ ID NO:11:

```
AGGACAGTGG GTACAATCAG GGTCAAGCCC TCAGCCAGGG CCAGGAGAGG GCCAGAGACT    60

GCTTCTGTTG AGTTAGGGGT CGGAGGGACT CAGAAGGGGG CAGGTGGGAA GGTGGACGGG   120

GGTTGTACCT GCCTGTTGCT GCCTCTAGCT CCTCTCTGCA TGTGTCCTGC AGGCTGGAAG   180

CTCCTGGCCA TGTTGGCTCT GGTCCTGGTC GTCATGGTGT GGTATTCCAT CTCCCGGGAA   240

GACAGGTACA TCGAGCCTTT TTATTTTCCC ATCCCAGAGA AGAAGGAGCC GTGCCTCCAG   300

GGTGAGGCAG AGAGCAAGGC CTCTAAGCTC TTTGGCAACT ACTCCCGGGA TCAGCCCATC   360

TTCCTGCGGC TTGAGGATTA TTTCTGGGTC AAGACGCCAT CTGCTTACGA GCTGCCCTAT   420

GGGACCAAGG GGAGTGAGGA TCTGCTCCTC CGGGTGCTAG CCATCACCAG CTCCTCCATC   480

CCCAAGAACA TCCAGAGCCT CAGGTGCCGC CGCTGTGTGG TCGTGGGGAA CGGGCACCGG   540

CTGCGGAACA GCTCACTGGG AGATGCCATC AACAAGTACG ATGTGGTCAT CAGATTGAAC   600

AATGCCCCAG TGGCTGGCTA TGAGGGTGAC GTGGGCTCCA AGACCACCAT GCGTCTCTTC   660

TACCCTGAAT CTGCCCACTT CGACCCCAAA GTAGAAAACA CCCAGACAC ACTCCTCGTC    720

CTGGTAGCTT TCAAGGCAAT GGACTTCCAC TGGATTGAGA CCATCCTGAG TGATAAGAAG   780

CGGGTGCGAA AGGGTTTCTG GAAACAGCCT CCCCTCATCT GGGATGTCAA TCCTAAACAG   840

ATTCGGATTC TCAACCCCTT CTTCATGGAG ATTGCAGCTG ACAAACTGCT GAGCCTGCCA   900

ATGCAACAGC CACGGAAGAT TAAGCAGAAG CCCACCACGG GCCTGTTGGC CATCACGCTG   960

GCCCTCCACC TCTGTGACTT GGTGCACATT GCCGGCTTTG GCTACCCAGA CGCCTACAAC  1020

AAGAAGCAGA CCATTCACTA CTATGAGCAG ATCACGCTCA AGTCCATGGC GGGGTCAGGC  1080

CATAATGTCT CCCAAGAGGC CCTGGCCATT AAGCGGATGC TGGAGATGGG AGCTATCAAG  1140

AACCTCACGT CCTTCTGA                                                1158
```

(2) INFORMATION FOR SEQ ID NO:12:

(i) SEQUENCE CHARACTERISTICS:
        (A) LENGTH: 332 amino acids
        (B) TYPE: amino acid
        (C) TOPOLOGY: linear (ii) MOLECULE TYPE: protein (xi) SEQUENCE DESCRIPTION: SEQ ID NO:12:

```
Met Cys Pro Ala Gly Trp Lys Leu Leu Ala Met Leu Ala Leu Val Leu
 1               5                  10                  15

Val Val Met Val Trp Tyr Ser Ile Ser Arg Glu Asp Arg Tyr Ile Glu
                20                  25                  30

Pro Phe Tyr Phe Pro Ile Pro Glu Lys Lys Glu Pro Cys Leu Gln Gly
                35                  40                  45

Glu Ala Glu Ser Lys Ala Ser Lys Leu Phe Gly Asn Tyr Ser Arg Asp
        50                  55                  60

Gln Pro Ile Phe Leu Arg Leu Glu Asp Tyr Phe Trp Val Lys Thr Pro
65                  70                  75                  80

Ser Ala Tyr Glu Leu Pro Tyr Gly Thr Lys Gly Ser Glu Asp Leu Leu
                85                  90                  95

Leu Arg Val Leu Ala Ile Thr Ser Ser Ser Ile Pro Lys Asn Ile Gln
                100                 105                 110

Ser Leu Arg Cys Arg Arg Cys Val Val Val Gly Asn Gly His Arg Leu
            115                 120                 125
```

```
Arg Asn Ser Ser Leu Gly Asp Ala Ile Asn Lys Tyr Asp Val Val Ile
    130                 135                 140
Arg Leu Asn Asn Ala Pro Val Ala Gly Tyr Glu Gly Asp Val Gly Ser
145                 150                 155                 160
Lys Thr Thr Met Arg Leu Phe Tyr Pro Glu Ser Ala His Phe Asp Pro
                165                 170                 175
Lys Val Glu Asn Asn Pro Asp Thr Leu Leu Val Leu Val Ala Phe Lys
                180                 185                 190
Ala Met Asp Phe His Trp Ile Glu Thr Ile Leu Ser Asp Lys Lys Arg
                195                 200                 205
Val Arg Lys Gly Phe Trp Lys Gln Pro Pro Leu Ile Trp Asp Val Asn
    210                 215                 220
Pro Lys Gln Ile Arg Ile Leu Asn Pro Phe Phe Met Glu Ile Ala Ala
225                 230                 235                 240
Asp Lys Leu Leu Ser Leu Pro Met Gln Gln Pro Arg Lys Ile Lys Gln
                245                 250                 255
Lys Pro Thr Thr Gly Leu Leu Ala Ile Thr Leu Ala Leu His Leu Cys
                260                 265                 270
Asp Leu Val His Ile Ala Gly Phe Gly Tyr Pro Asp Ala Tyr Asn Lys
                275                 280                 285
Lys Gln Thr Ile His Tyr Tyr Glu Gln Ile Thr Leu Lys Ser Met Ala
    290                 295                 300
Gly Ser Gly His Asn Val Ser Gln Glu Ala Leu Ala Ile Lys Arg Met
305                 310                 315                 320
Leu Glu Met Gly Ala Ile Lys Asn Leu Thr Ser Phe
                325                 330 332

(2) INFORMATION FOR SEQ ID NO:13:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:13:

Lys Tyr Pro Tyr Arg Pro Thr Thr Thr Thr Arg Ile Ile Glu Glu Gln
1               5                   10                  15
Lys Val Ser Ala Phe Phe
            20      22

(2) INFORMATION FOR SEQ ID NO:14:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:14:

Cys Arg Arg Cys Ile Ile Val Gly Asn Gly Gly Val Leu Ala Asn Lys
1               5                   10                  15
Ser Leu Gly Ser Arg Ile Asp Asp Tyr Asp Ile Val Leu Arg Leu Asn
            20                  25                  30
Ser Ala Pro Val Lys Gly Phe Glu Lys Asp Val Gly Ser Lys Thr Thr
            35                  40                  45
Leu Arg Ile Thr Tyr Pro Glu
            50                  55
```

(2) INFORMATION FOR SEQ ID NO:15:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:15:

```
Cys Arg Arg Cys Ala Val Val Gly Asn Ser Gly Asn Leu Lys Glu Ser
 1               5                  10                  15

Tyr Tyr Gly Pro Gln Ile Asp Ser His Asp Phe Val Leu Arg Met Asn
                20                  25                  30

Lys Ala Pro Thr Glu Gly Phe Glu Ala Asp Val Gly Ser Lys Thr Thr
                35                  40                  45

His His Phe Val Tyr Pro Glu
                50                  55
```

(2) INFORMATION FOR SEQ ID NO:16:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:16:

```
Tyr Gln Arg Cys Ala Val Val Ser Ser Ala Gly Ser Leu Lys Asn Ser
 1               5                  10                  15

Gln Leu Gly Arg Glu Ile Asp Asn His Asp Ala Val Leu Arg Phe Asn
                20                  25                  30

Gly Ala Pro Thr Asp Asn Phe Gln Gln Asp Val Gly Ser Lys Thr Thr
                35                  40                  45

Ile Arg Leu Met Asn Ser Gln
                50                  55
```

(2) INFORMATION FOR SEQ ID NO:17:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:17:

```
Phe Gln Thr Cys Ala Ile Val Gly Asn Ser Gly Val Leu Leu Asn Ser
 1               5                  10                  15

Gly Cys Gly Gln Glu Ile Asp Thr His Ser Phe Val Ile Arg Cys Asn
                20                  25                  30

Leu Ala Pro Val Gln Glu Tyr Ala Arg Asp Val Gly Leu Lys Thr Asp
                35                  40                  45

Leu Val Thr Met Asn Pro Ser
                50                  55
```

(2) INFORMATION FOR SEQ ID NO:18:

(i) SEQUENCE CHARACTERISTICS:
        (A) LENGTH: 340 amino acids
        (B) TYPE: amino acid
        (D) TOPOLOGY: linear (ii) MOLECULE TYPE: protein (xi) SEQUENCE DESCRIPTION: SEQ ID NO:18:

```
Ser Lys Gln Asp Pro Lys Glu Asp Ile Pro Ile Leu Ser Tyr His Arg
 1               5                  10                  15

Val Thr Ala Lys Val Lys Pro Gln Pro Ser Phe Gln Val Trp Asp Lys
                20                  25                  30

Asp Ser Thr Tyr Ser Lys Leu Asn Pro Arg Leu Leu Lys Ile Trp Arg
            35                  40                  45

Asn Tyr Leu Asn Met Asn Lys Tyr Lys Val Ser Tyr Lys Gly Pro Gly
 50                  55                  60

Pro Gly Val Lys Phe Ser Val Glu Ala Leu Arg Cys His Leu Arg Asp
 65                  70                  75                  80

His Val Asn Val Ser Met Ile Glu Ala Thr Asp Phe Pro Phe Asn Thr
                85                  90                  95

Thr Glu Trp Glu Gly Tyr Leu Pro Lys Glu Asn Phe Arg Thr Lys Val
            100                 105                 110

Gly Pro Trp Gln Arg Cys Ala Val Val Ser Ser Ala Gly Ser Leu Lys
                115                 120                 125

Asn Ser Gln Leu Gly Arg Glu Ile Asp Asn His Asp Ala Val Leu Arg
130                 135                 140

Phe Asn Gly Ala Pro Thr Asp Asn Phe Gln Gln Asp Val Gly Ser Lys
145                 150                 155                 160

Thr Thr Ile Arg Leu Met Asn Ser Gln Leu Val Thr Thr Glu Lys Arg
                165                 170                 175

Phe Leu Lys Asp Ser Leu Tyr Thr Glu Gly Ile Leu Ile Val Trp Asp
                180                 185                 190

Pro Ser Val Tyr His Ala Asp Ile Pro Lys Trp Tyr Gln Lys Pro Asp
                195                 200                 205

Tyr Asn Phe Phe Glu Thr Tyr Lys Ser Tyr Arg Arg Leu Asp Pro Ser
210                 215                 220

Gln Pro Phe Tyr Ile Leu Lys Pro Gln Met Pro Trp Glu Leu Trp Asp
225                 230                 235                 240

Ile Ile Gln Glu Ile Ser Ala Asp Leu Ile Gln Pro Asn Pro Pro Ser
                245                 250                 255

Ser Gly Met Leu Gly Ile Ile Met Met Thr Leu Cys Asp Gln Val
                260                 265                 270

Asp Ile Tyr Glu Phe Leu Pro Ser Lys Arg Lys Thr Asp Val Cys Tyr
            275                 280                 285

Tyr His Gln Lys Phe Phe Asp Ser Ala Cys Thr Met Gly Ala Tyr His
290                 295                 300

Pro Leu Leu Phe Glu Lys Asn Met Val Lys His Leu Asn Glu Gly Thr
305                 310                 315                 320

Asp Glu Asp Ile Tyr Leu Phe Gly Lys Ala Thr Leu Ser Gly Phe Arg
            325                 330                 335

Asn Ile Arg Cys
            340
```

(2) INFORMATION FOR SEQ ID NO:19:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:19:

Phe Val Arg Asn
1           4

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:20:

Pro Met Arg Lys Lys Ser Thr Leu Lys
1               5               9

(2) INFORMATION FOR SEQ ID NO:21:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:21:

Asp Val Gly Ser Lys Thr Thr
1               5       7

(2) INFORMATION FOR SEQ ID NO:22:

(i) SEQUENCE CHARACTERISTICS:
        (A) LENGTH: 53 nucleotides
        (B) TYPE: nucleic acid
        (C) STRANDEDNESS: single
        (D) TOPOLOGY: linear (ii) MOLECULE TYPE: protein (iv) ORIGINAL SOURCE:
        (A) ORGANISM: porcine (xi) SEQUENCE DESCRIPTION: SEQ ID NO:22:

ACCCTGAAGC TGCGCACCCT GCTGGTGCTG TTCATCTTCC TGACCTCCTT CTT           53

(2) INFORMATION FOR SEQ ID NO:23:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: porcine (xi) SEQUENCE DESCRIPTION: SEQ ID NO:23:

GGAAGCTTTG SCRNMGSTGY RYCRTCGT           28

(2) INFORMATION FOR SEQ ID NO:24:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (ii) MOLECULE TYPE: cDNA (vi) ORIGINAL SOURCE:
             (A) ORGANISM: porcine (xi) SEQUENCE DESCRIPTION: SEQ ID NO:24:

CCGGATCCGG TRGTYTTNSN SCCACRTC                                              28

(2) INFORMATION FOR SEQ ID NO:25:

(i) SEQUENCE CHARACTERISTICS:
             (A) LENGTH: 28 nucleotides
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: porcine (xi) SEQUENCE DESCRIPTION: SEQ ID NO:25:

GGAAGCTTTG SCRNMGSTGY RYCRTCGT                                              28

(2) INFORMATION FOR SEQ ID NO:26:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: porcine (xi) SEQUENCE DESCRIPTION: SEQ ID NO:26:

CCGGATCCGG TRGTYTTNSN CCSACRTC                                              28

(2) INFORMATION FOR SEQ ID NO:27:

(i) SEQUENCE CHARACTERISTICS:
             (A) LENGTH: 55 amino acids
             (B) TYPE: amino acid
             (D) TOPOLOGY: linear (ii) MOLECULE TYPE: protein (xi) SEQUENCE DESCRIPTION: SEQ ID NO:27:

Cys Arg Arg Cys Val Val Val Gly Asn Gly His Arg Leu Arg Asn Ser
  1               5                  10                  15

Ser Leu Gly Asp Ala Ile Asn Lys Tyr Asp Val Val Ile Arg Leu Asn
             20                  25                  30

Asn Ala Pro Val Ala Gly Tyr Glu Gly Asp Val Gly Ser Lys Thr Thr
             35                  40                  45

Met Arg Leu Phe Tyr Pro Glu
             50                  55

(2) INFORMATION FOR SEQ ID NO:28:

(i) SEQUENCE CHARACTERISTICS:
             (A) LENGTH: 55 amino acids
             (B) TYPE: amino acid
             (D) TOPOLOGY: linear (ii) MOLECULE TYPE: protein (xi) SEQUENCE DESCRIPTION: SEQ ID NO:28:

Cys Arg Arg Cys Xaa Val Val Gly Asn Xaa Gly Xaa Leu Xaa Asn Ser
1               5                   10                  15

Xaa Leu Gly Xaa Xaa Ile Asp Xaa Xaa Asp Xaa Val Xaa Arg Xaa Asn
                20                  25                  30

Xaa Ala Pro Xaa Xaa Gly Phe Glu Xaa Asp Val Gly Ser Lys Thr Thr
            35                  40                  45

Xaa Arg Xaa Xaa Tyr Pro Glu
    50                  55

(2) INFORMATION FOR SEQ ID NO:29:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO:29:

Val Val Pro Gly Asn Val Asp Pro Leu Leu Glu Lys Arg Leu Val Ser
1               5                   10                  15

Cys Arg Arg Cys Ala Val Val Gly Asn Ser Gly Asn Leu Lys Glu Ser
                20                  25                  30

Tyr Tyr Gly Pro Gln Ile Asp Ser His Asp Phe Val Leu Arg Met Asn
            35                  40                  45

Lys Ala Pro Thr Glu Gly Phe Glu Ala Asp Val Gly Ser Lys Thr Thr
    50                  55                      60

His His Phe Val Tyr Pro Glu Ser Phe Arg Glu Leu Ala
65                  70                  75

(2) INFORMATION FOR SEQ ID NO:30:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO:30:

Trp Glu Gly Tyr Leu Pro Lys Glu Asn Phe Arg Thr Lys Val Gly Pro
1               5                   10                  15

Tyr Gln Arg Cys Ala Val Val Ser Ser Ala Gly Ser Leu Lys Asn Ser
                20                  25                  30

Gln Leu Gly Arg Glu Ile Asp Asn His Asp Ala Val Leu Arg Phe Asn
            35                  40                  45

Gly Ala Pro Thr Asp Asn Phe Gln Gln Asp Val Gly Ser Lys Thr Thr
    50                  55                      60

Ile Arg Leu Met Asn Ser Gln Leu Val Thr Thr Glu Lys
65                  70                  75

(2) INFORMATION FOR SEQ ID NO:31:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:31:

```
Ala Phe Val Asp Ser Arg Gly Ser Pro Gly Glu Leu Ser Glu
 1               5                  10
```

(2) INFORMATION FOR SEQ ID NO:32:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:32:

```
Leu Asn Ser Ala Pro Val Lys
 1               5
```

(2) INFORMATION FOR SEQ ID NO:33:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:33:

```
Leu Thr Pro Ala Leu Asp Ser Leu His Cys Arg
 1               5                  10
```

(2) INFORMATION FOR SEQ ID NO:34:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:34:

```
Ile Asp Asn His Asp Ala Val Leu Arg Phe Asn Gly Ala Pro Thr Asp
 1               5                  10                  15
```

(2) INFORMATION FOR SEQ ID NO:35:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:35:

```
Ile Asp Ser His Asp Phe Val Leu Arg Met Asn Lys Ala Pro Thr Gln
 1               5                  10                  15
```

(2) INFORMATION FOR SEQ ID NO:36:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:36:

```
Ile Asp Asp Tyr Asp Ile Val Leu Arg Leu Asn Ser Ala Pro Val Lys
 1               5                  10                  15
```

COMPOSITIONS AND METHODS FOR THE IDENTIFICATION AND SYNTHESIS OF SIALYLTRANSFERASES

This application is a continuation-in-part of application Ser. No. 07/925,369 filed Aug. 4, 1992 now abandoned, which was a continuation-in-part of application Ser. No. 07/850,357 filed Mar. 9, 1992 now abandoned.

This invention was made with Government support under Grant Nos. GM-27904 and GM-08042, awarded by the National Institutes of Health. The Government has certain rights in this invention.

BACKGROUND OF THE INVENTION

This invention relates to the sialyltransferase gene family, a group of glycosyltransferases responsible for the terminal sialylation of carbohydrate groups of glycoproteins, glycolypids and oligosaccharides which contain a conserved region of homology in the catalytic domain. Members of the sialyltransferase gene family comprise Galβ1,3GalNAc α2,3 sialyltransferase and Gal1,3(4)GlcNAc α2,3 sialyltransferase. The invention further relates to novel forms and compositions thereof and particularly to the means and methods for the identification and production of members of the sialyltransferase gene family to homogeneity in significant useful quantities. This invention also relates to preparation of isolated deoxyribonucleic acid (DNA) coding for the production of sialyltransferases; to methods of obtaining DNA molecules which code for sialyltransferases; to the expression of human and mammalian sialyltransferases utilizing such DNA, as well as to novel compounds, including novel nucleic acids encoding sialyltransferases or fragments thereof. This invention is also directed to sialyltransferase derivatives, particularly derivatives lacking cytoplasmic and/or transmembrane portions of the protein, and their production by recombinant DNA techniques.

Sialyltransferases are a family of enzymes that catalyze the transfer of sialic acid (SA) to terminal portions on the carbohydrate groups of glycolipids and oligosaccharides in the general reaction:

Cytididine 5 monophosphate-sialic acid (CMP-SA)+HO-acceptor→CMP+SA-O-Acceptor (Beyer, T. A. et. Adv. Enzynol. 52, 23–175 [1981]). Sialyltransferases are found primarily in the Golgi apparatus of cells where they participate in post-translational glycosylation pathways. (Fleischer, B. J. Cell Biol. 89, 246–255 [1981]). They are also found in body fluids, such as breast milk, colostrum and blood. At least 10–12 different sialyltransferases are required to synthesize all the sialyloligossacharide sequences known. Four sialyltransferases have been purified. (Weinstein, J. et al., J. Biol. Chem. 257, 13835–13844 [1982]; Miagi, T and Tsuiki, S. Eur. J. Biochem. 125, 253–261 [1982]; and Joziasse, D. H. et al., J. Biol. Chem. 260, 4941–4951 [1985]). More specifically, a Galβ1,4GlcNAc α2–6 sialyltransferase and a Galβ1,3(4)GlcNAc α2–3 sialyltransferase have been purified from rat liver membranes. (Weinstein et al. Ibid)

Other glycosyltransferases have been isolated as soluble enzymes in serum, milk or colostrum including sialyl-, fucosyl-, galactosyl-, N-acetylgucosaminyl-, and N-acetylgalactosaminyltransferases. (Beyer et al. Ibid.) Bovine and human β-N-acetylglucosamide β1,4-galactosyltransferase has been isolated (Narimatsu, H. et al. Proc. Nat. Acad. Sci. U.S.A. 83, 4720–4724 [1986]; Shaper, N. L. et al., Proc. Nat. Acad. Sci. U.S.A. 83, 1573–1577 [1986]; Appert, H. E. et al., Biochem. Biophys. Res. Common 139, 163–168 [1986]; and, Humphreys-Beyer, M. G. et al., Proc. Nat. Acad. Sci. U.S.A. 83, 8918–8922 [1986]. These purified glycosyltransferases differ in size which may be due to the removal of portions of the protein not essential for activity, such as the membrane spanning domains.

Comparison of the deduced amino acid sequences of the cDNA clones encoding the glycosyltransferases including galactosyltransferases, sialyltransferase, fucosyltransferase and N-acetylgalactosaminyltransferase, reveals that these enzymes have virtually no sequence homology. Some insight into how this family of glycosyltransferases might be structurally related has come from recent analysis of the primary structures of cloned sialyltransferases (Weinstein, J. et al., ibid.). However, they all have a short $NH_2$-terminal cytoplasmic tail, a 16–20 amino acid signal-anchor domain, and an extended stem region which is followed by the large COOH-terminal catalytic domain Weinstein, J. et al., J. Biol. Chem. 262, 17735–17743 [1987] Paulson, J. C. et al., J. Biol. Chem. 264, 17615–17618 [1989]. Signal-anchor domains act as both uncleavable signal peptides and as membrane-spanning regions and orient the catalytic domains of these glycosyltransferases within the lumen of the Golgi apparatus. Common amino acid sequences would be expected within families of glycosyltransferases which share similar acceptor or donor substrates; however, surprisingly few regions of homology have been found within the catalytic domains of glycosyltransferases, and no significant sequence homology is found with any other protein in GenBank (Shaper, N. L. et al., J. Biol Chem 216, 10420–10428 [1988], D'Agostaso, G. et al., Eur J. Biochem 183, 211–217 [1989] and Weinstein, J. et al., J. Biol. Chem 263, 17735–17743 [1987]). This is especially surprising for the Gal α1,3-GT and GlcNAc β1,4-GT, two galactosyltransferases. However, while these galactosyltransferases exhibit no overall homology, there is a common hexapeptide KDKKND for the Gal α1,3-GT (bovine, 304–309) and RDKKNE for the GlcNAc β1,4-GT (bovine, human, murine amino acids 346–351). (Joziasse et al., J. Biol Chem 264, 14290–14297 [1989].)

Sialic acids are terminal sugars on carbohydrate groups present on glycoproteins and glycolipids and are widely distributed in animal tissues (Momol, T. et al., J. Biol. Chem. 261, 16270–16273 [1986]). Sialic acids play important roles in the biological functions of carbohydrate structures because of their terminal position. For instance, sialic acid functions as the ligand for the binding of influenza virus to a host cell (Paulson, J. C., The Receptors, Vol. 2, Conn, P. M., ed., pp. 131–219, Academic Press [1985]). Even a change in the sialic acid linkage is sufficient to alter host specificity (Roger, G. N. et al., Nature 304, 76–78 [1983]). The neural cell adhesion molecule (NCAM) is subject to developmentally regulated polysialylation which is believed to modulate NCAm mediated cell adhesion during the development of the nervous system (Rutishauser, U. et al., Science 240, 53–37 [1988] and Rutishauser, U., Adv. Exp. Med. Biol. 265, 179–18 [1990]). Recently, a carbohydrate structure, sialyl lewis X ($SLe^x$) has been shown to function as a ligand for the endothelial leucocyte adhesion molecule ("E-Selectin") which mediates the binding of neutrophils to activated endothelial cells (Lowe et al., 1990; Phillips et al., 1990; Goelz et al., 1990; Walz et al., 1990; Brandley et al., 1990). P-selectin (platelet activation dependent granule to external membrane protein; CD62), another member of the selectin family (Stoolman, L. M., Cell 56, 907–910 [1989]), has also been demonstrated to recognize $SLe^x$ present on monocytes and PMNs (Larsen et al., Proc. Natl. Acad. Sci.

USA 87, 6674–6678 [1990]; Momol et al., J. Biol. Chem. 261, 16270–16273 [1986]; Polley et al., Proc. Natl. Acad. Sci. USA 88, 6224–6228 [1991]; Chan, K. F. J., J. Biol. Chem. 263, 568–574 [1988]; Beyer, T. A. et al., Adv. Enzymol., 52, 23–175 [1981]). In both instances, sialic acid is a key component for the carbohydrate structure to function as a ligand. In addition to playing a role in cell adhesion, sialic acid containing carbohydrate structures have been implicated as playing a direct role in differentiation. The hematopoietic cell line HL-60 can be induced to differentiate by treatment with the glycolipid $G_{M3}$. Gangliosides are also thought to play a role in modulation of growth factor-protein kinase activities and in the control of the cell cycle.

One such sialyltransferase has been purified, as described in U.S. Pat. No. 5,047,335. While some quantities of purified sialyltransferase have been available, they are available in very low amounts in part because they are membrane bound proteins of the endoplasmic reticulum and the golgi apparatus. Significant cost, both economic and of effort, of purifying these sialyltransferases makes it a scarce material. It is an object of the present invention to isolate DNA encoding sialyltransferase and to produce useful quantities of mammalian, particularly human, sialyltransferase using recombinant DNA techniques. It is a further object to provide a means for obtaining the DNA encoding other members of the sialyltransferase gene family from various tissues as well as from other species. It is a further object of the present invention to prepare novel forms of sialyltransferases. It is still another object herein to provide an improved means for catalyzing the transfer of sialic acid to terminal positions on certain carbohydrate groups. These and other objects of this invention will be apparent from the specification as a whole.

SUMMARY OF THE INVENTION

Objects of this invention have been accomplished by a method comprising: identifying and cloning genes which code for mammalian sialyltransferases (defined hereinafter) including, but not limited to porcine Galβ1,3GalNAc α2,3 sialyltransferase and rat Galβ1,3(4)GlcNAc α2,3 sialyltransferase (other than rat Galβ1,4GlcNAc α2,6 sialyltransferase); incorporating that gene into a recombinant DNA vector; transforming a suitable host with the vector including that gene; expressing the mammalian sialyltransferase genes in such a host; and recovering the mammalian sialyltransferase that is produced. Alternatively, a variety of other recombinant techniques may be used to obtain expression of sialyltransferse. Similarly, the present invention makes it possible to produce mammalian sialyltransferase and/or derivatives thereof by recombinant techniques, as well as providing means for producing such sialyltransferases. The sialyltransferases are low abundance proteins and difficult to purify. The isolation and identification of the sialyltransferase genes were extremely difficult. The mRNA was rare, and cell lines or other sources of large quantities of mRNA were unavailable. This invention for the first time established a sialyltransferase gene family defined by a conserved region of homology in the catalytic domain of the enzymes.

The present invention is directed to compositions of and methods of producing mammalian sialyltransferase via recombinant DNA technology, including: 1) the discovery and identity of the entire DNA sequence of the enzymes and the 5'-flanking region thereof; 2) the construction of cloning and expression vehicles comprising said DNA sequence, enabling the expression of the mammalian sialyltransferase protein, as well as fusion or signal N-terminus conjugates thereof; and 3) viable cell cultures and other expression systems and other expression systems, genetically altered by virtue of their containing such vehicles and capable of producing mammalian sialyltransferase. This invention is further directed to compositions and methods of producing DNA which code for cellular production of mammalian sialyltransferase. Yet another aspect of this invention are new compounds, including deoxyribonucleotides and ribonucleotides which are utilized in obtaining clones which are capable of expressing sialyltransferase. Still another aspect of the present invention is sialyltransferase essentially free of all naturally occurring substances with which it is typically found in blood and/or tissues, i.e., the sialyltransferase produced by recombinant means will be free of those contaminants typically found in its in vivo physiological milieu. In addition, depending upon the method of production, the sialyltransferase hereof may contain associated glycosylation to a greater or lesser extent compared with material obtained from its in vivo physiological milieu, i.e., blood and/or tissue. This invention is further directed to novel sialyltransferase derivatives, in particular derivatives lacking sialyltransferase amino terminal residues, e.g., derivatives lacking the short $NH_2$ cytoplasmic domain or the hydrophobic N-terminal signal-anchor sequence which constitutes the sialyltransferase transmembrane domain and stem region.

The mammalian sialyltransferase and derivatives thereof of this invention are useful in the addition of sialic acids on carbohydrate groups present on glycoproteins and glycolipids. In addition, the sialyltransferase and derivatives thereof are enzymatically useful by adding sialic acid to sugar chains to produce carbohydrates which function as determinants in biological recognition. Such sialyltransferase enzymes may be employed in multi-enzyme systems for synthesis of oligosaccharides and derivatives (Ichikawa et al., J. Am. Chem. Soc. 113, 4698 [1991] and Ichikawa et al., J. Am. Chem. Soc. 113, 6300 [1991]). Finally, the DNA, particularly the conserved region of homology of the catalytic domain, encoding the sialyltransferase gene family of this invention is useful in providing a means for cloning the gene encoding other members of the sialyltransferase gene family. Other uses for the sialyltransferase and the DNA encoding sialyltransferase will be apparent to those skilled in the art.

BRIEF DESCRIPTION OF THE DRAWINGS

FIG. 1 Nucleotide and amino acid sequence of porcine Galβ1,3GalNAc α2,3 sialyltransferase ("α2,3-O"). The nucleotide sequence of the porcine α2,3-O mRNA was determined from DNA sequence analysis of two overlapping clones, λST1 and λST2. Predicted amino acids of the α2,3-O polypeptide are shown above the DNA sequence and are numbered from the first residue of the N-terminal of the analagous purified protein. The proposed signal-anchor sequence is indicated (light box). Potential glycosylation sites with the sequence Asn-X-Thr are marked with an asterisk (*). The sequence corresponds to the long form of the α2,3 sialyltransferase, encoded by the overlapping clones λST1 and λST2. See Sequence ID Nos. 1 and 2.

FIG. 2 Nucleotide and amino acid sequence of rat Galβ1, 3(4)GlcNAc α2,3-sialyltransferase ("α2,3-N"). The nucleotide sequence of the rat α2,3-N mRNA was determined from DNA sequence analysis. Predicted amino acids of the sialyltransferase polypeptide are shown above the DNA sequence and are numbered from the first residue of the mature protein as determined by N-terminal protein sequencing. See Sequence ID Nos.3 and 4.

FIG. 4 Purification of the α2,3-O sialyltransferase on CDP-hexanolamine agarose (column III, CDP elution). Enzyme activities were determined using the specific acceptor substrate antifreeze glycoprotein (AFGP). In columns A and B elution of enzyme activity correlated predominantly with 48 kDa and a 45 kDa protein species, respectively (see inset, SDS-PAGE). These two species, form A and form B of the α2,3 sialyltransferase, had specific activities of 8–10 units/mg protein. The 48 kDA and 45 kDA species were blotted to a PVDF membrane and analyzed by $NH_2$-terminal sequencing.

FIGS. 6A and 6B Comparison of the domain structures and homologous regions of two sialyltransferases. A, Alignment of the primary sequences of the α2,6 sialyltransferase and the α2,3-O sialyltransferase reveals a 45 amino acid region of 64% sequence identity and 84% sequence similarity. B, The homologous domain spans the junction between exons 2 and 3 of the α2,6 sialyltransferase, and lies within the catalytic domains of both enzymes. The α2,3ST sequence shown in FIG. 6B corresponds to SEQ. ID. NO.29. The α2,6ST sequence corresponds to SEQ. ID. NO.30;

FIG. 12 The conserved region shared by the three cloned sialyltransferases. The three cloned sialyltransferases are the rat Galβ1,3(4)GlcNAc α2,3-sialyltransferase (ST3N) (SEQ. ID. NO.14), the porcine Galβ1,3GalNAc α2,3-sialyltransferase (ST30) (SEQ. ID. NO.15), and the rat Galβ1,4GlcNAc α2,6-sialyltransferase (ST6N) (SEQ. ID. NO.16). The region consists of 55 amino acids from residue 156 to residue 210 of the Galβ1,3(4)GlcNAc α2,3-sialyltransferase (ST3N). Amino acid identities are indicted by boxing.

FIG. 13 Predicted amino acid sequence of the amplified fragment, SM1(SEQ. ID. NO.17), and comparison to the previously characterized conserved region of homology. The consensus conserved region of homology was generated from comparison of the conserved region of homology of the cloned and characterized sialyltransferases and the amplified fragment SM1. The invariant amino acids are indicated by upper case letters while amino acids present in more than 50% of the conserved region of homology are in lower case letters. positions where r or q is found are denoted by b; positions were either i or v is found are denoted by x. The underlined amino acids represent the regions that were used in the design of the degenerate primers. Changes in the previously invariant amino acids found in the amplified fragment are marked with asterisks.

FIG. 14 Nucleotide and predicted amino acid sequences of STX1. The predicted amino acid sequence of the longest open reading frame encodes for the conserved region of homology SM1 (amino acids 154–208), identified by a shaded box. The proposed signal-anchor (amino acids 8–23) sequence is boxed and the potential N-linked glycosylation sites are underlined. See (SEQ. ID. NOS. 7 and 8).

FIG. 15 Nucleotide sequence of human Galβ1,3(4) GlcNAcα2,3-sialyltransferase (SEQ. ID. NO:9) showing comparison to corresponding rat enzyme (SEQ. ID. NO:3).

FIG. 16 The amino acid sequence for human Galβ1,3(4) GlcNAcα2,3-sialyltransferase (SEQ. ID. NO:10) showing comparison to corresponding rat enzyme (SEQ. ID. NO:4).

FIG. 17 Nucleotide/Amino acid sequence for ST3 sialyltransferase (SEQ. ID. NOS: 11 and 12, respectively).

FIG. 18 Comparison of amino acid sequences of sialyltransferases of the present invention showing homologous motif (SEQ. ID. NO:28). ST3 corresponds to SEQ. ID. NO: 12; ST3N corresponds to SEQ. ID. NO: 4; ST3O corresponds to SEQ. ID. NO: 2; and ST6N corresponds to SEQ. ID. NO: 18.

DETAILED DESCRIPTION

Figure 3:
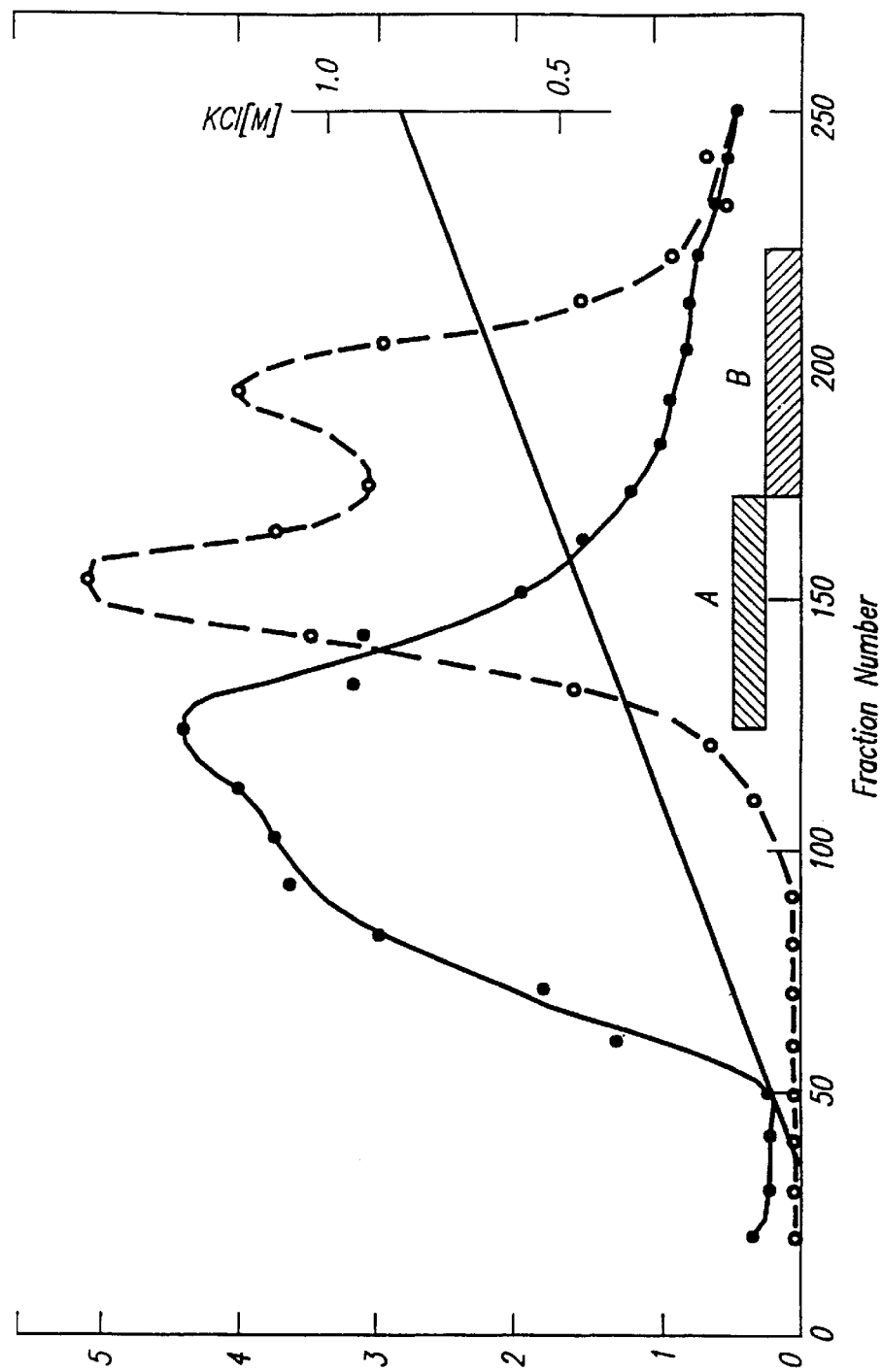
FIG. 3 Purification of the α2,3-O sialyltransferase on CDP-hexanolamine agarose (KCl elution). Homogenate from 2 kg porcine liver were loaded onto a CDP-hexanolamine agarose column and eluted with a linear gradient of KCl (see Experimental Procedures). Protein concentration and sialyltransferase activity using lactose as an acceptor substrate were determined for individual fractions. The two peaks of enzyme activity were separated into pools A and B, as indicated.

As used herein, sialyltransferase or sialyltransferase derivatives refer to sialyltransferase enzymes other than rat Galβ1,4GlcNAc α2,6 sialyltransferase which contain a conserved region of homology in the catalytic domain and are enzymatically active in transferring sialic acid to a terminal position on sugar chains of glycoproteins, glycolipids, oligosaccharides and the like. Examples of enzymatically functional sialyltransferases are those capable of transferring sialic acid from CMP-sialic acid to an acceptor oligosaccharide, where the oligosaccharide acceptor varies depending upon the particular sialyltransferase.

Figure 1:
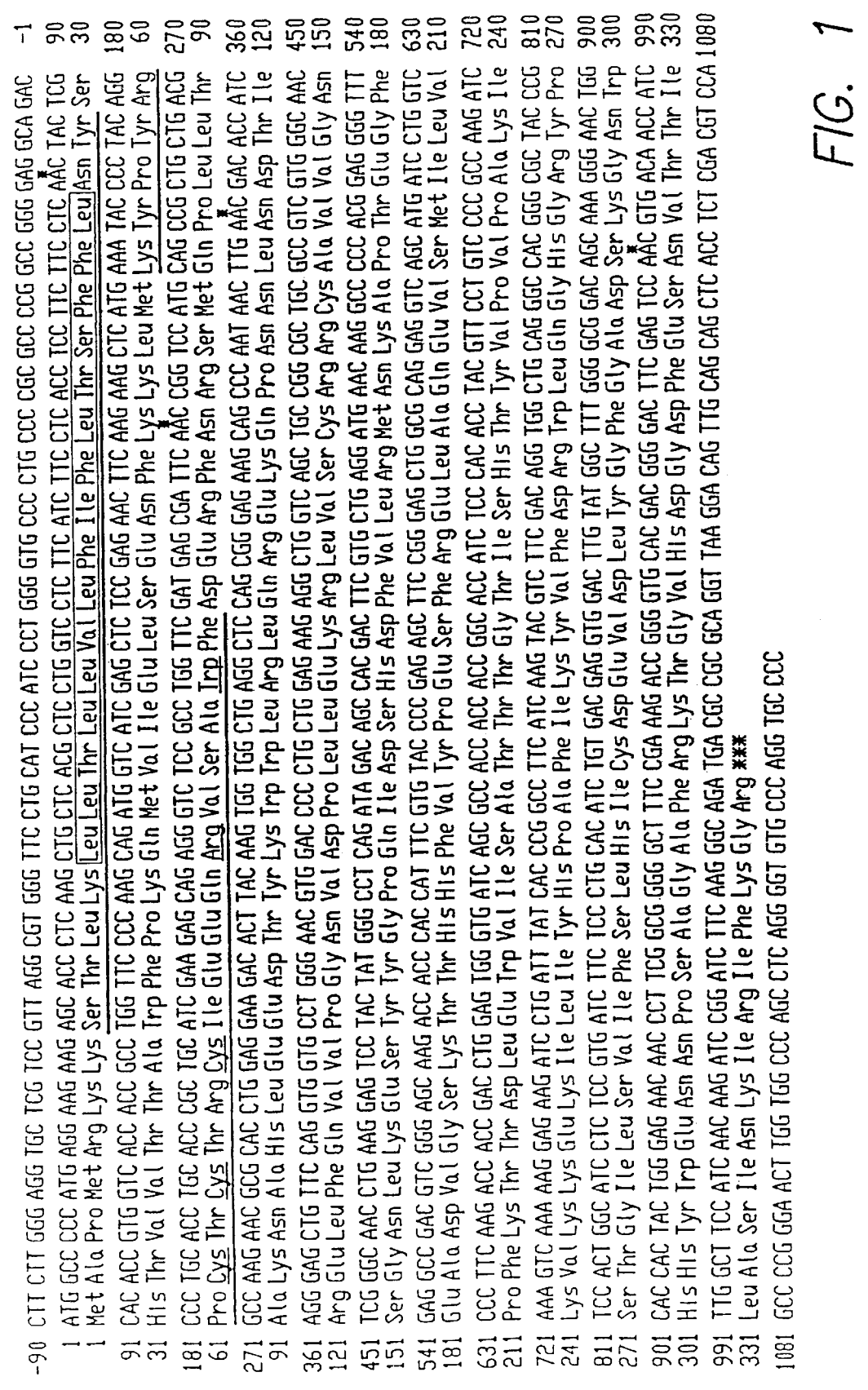

"Conserved region of homology" refers to a series of amino acids in one sialyltransferase which is essentially identical to the same series of amino acids in another sialyltransferase enzyme once the sequences of the two enzymes have been aligned. In the sialyltransferase gene family of this invention the conserved region of homology is in the catalytic domain and extends over at least about 7 contiguous amino acids, preferably at least about 20 amino acids and most preferably over at least about 55 amino acids having the amino acid sequence of residues 156–210 of FIG. 2 or residues 142–196 of FIG. 1. Once having identified the conserved region of homology, amino acid sequence variants of the conserved region may be made and fall into one or more of three classes: substitutional, insertional, or deletional variants. These variants ordinarily are prepared by site-specific mutagenesis nucleotides in the DNA encoding the sialyltransferase, thereby producing DNA encoding sialyltransferase comprising a conserved region of homology variant.

The sialyltransferases in accordance with the present invention include: rat Galβ1,3(4)GlcNAc α2,3 sialyltransferase (herein referred to as "α2,3-N" and identified as Seq. ID No.3) which forms the NeuNAc α2,3Galβ1,3GlcNAc and NeuAcα2,3Galβ1,4GlcNAc sequences which often terminate complex N-linked oligosaccharides; porcine Galβ1, 3GalNAc α2,3 sialyltransferase (herein referred to as "α2, 3-0" and identified as Seq. ID No.1) which forms NeuAcα2, 3Galβ1,3GalNAc found on sugar chains O-linked to threonine or serine as well as a terminal sequence on certain gangliosides; human Galβ1,3(4)G1cNAcα2,3 sialyltransferase (Seq. ID No.10); and the sialyltransferases identified as ST3 and set forth in Seq. ID No.12.

The SEQ. ID. NOS. which are set forth in this specification are summarized in the following table:

| SEQ. ID. NO. | TYPE | IDENTIFICATION | |
|---|---|---|---|
| 1 | DNA | Porcine α2,3-0 (ST30) | |
| 2 | AA | Porcine α2,3-0 (ST30) | |
| 3 | DNA | Rat α2,3-N (ST3N) | |
| 4 | AA | Rat α2,3-N (ST3N) | |
| 5 | DNA | Oligonucleotide | |
| 6 | AA | 48 Kda peptide (FIG. 5) | |
| 7 | DNA | SM1 gene (STX-1) | } Example 10 |
| 8 | AA | STX-1 | |
| 9 | DNA | α2,3-N(Human ST3N) | } Example 11 |
| 10 | AA | α2,3-N(Human ST3N) | |
| 11 | DNA | Human ST3 | } Example 12 |
| 12 | AA | Human ST3 | |
| 13 | AA | 45 Kda peptide (FIG. 5) | |
| 14 | AA | Conserved Region of ST3N (FIG. 12) | |
| 15 | AA | Conserved Region of ST3O (FIG. 12) | |
| 16 | AA | Conserved Region of ST6N (FIG. 12) | |
| 17 | AA | Conserved Region of STX-1 (FIG. 13) | |
| 18 | AA | Rat α2,6-N (ST6N) | |
| 19 | AA | Conformational Bend Residue in ST3N | |
| 20 | AA | Conformational Bend Residue in ST3O | |
| 21 | AA | Seven Amino Acid Conserved Region | |
| 22 | DNA | Oligonucleotide probe | |
| 23 | DNA | Oligonucleotide probe | |
| 24 | DNA | Oligonucleotide probe | |
| 25 | DNA | Oligonucleotide probe | |
| 26 | DNA | Oligonucleotide probe | |
| 27 | AA | Conserved Region of Homology | |
| 28 | AA | Homologous Motif of Conserved Region | |
| 29 | AA | Peptide Containing ST3O Conserved Region | |
| 30 | AA | Peptide Containing ST6N Conserved Region | |

Figure 2:
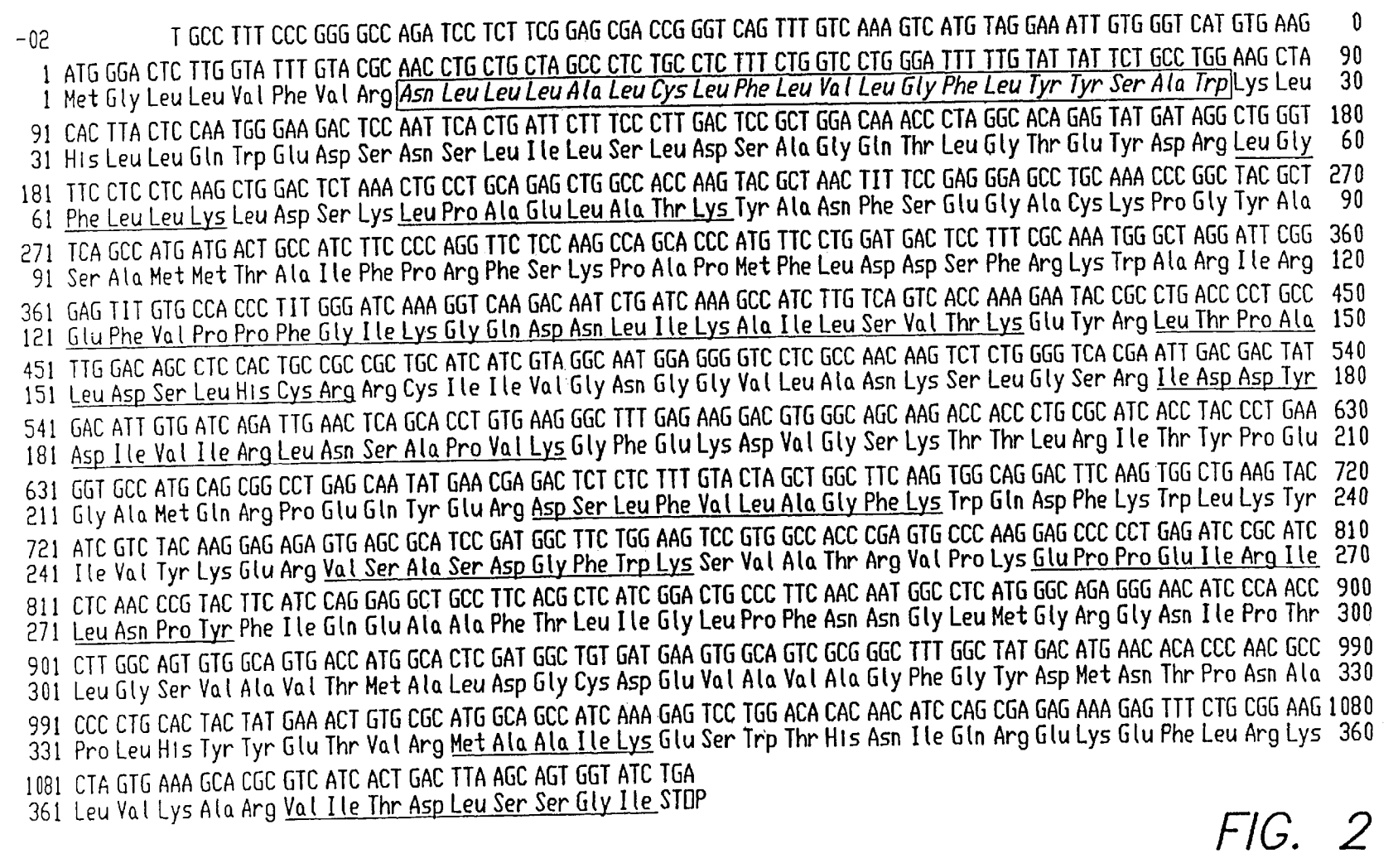

Included within the scope of sialyltransferase as that term is used herein are sialyltransferase having native glycosylation and the amino sequences of rat and porcine sialyltransferase as set forth in FIGS. 1 or 2, analogous sialyltransferase from other animal species such as bovine, human and the like, as well as from other tissues, deglycosylated or unglycosylated derivatives of such sialyltransferases, amino acid sequence variants of sialyltransferase and in vitro-generated covalent derivatives of sialyltransferases. All of these forms of sialyltransferase contain a conserved region of homology and are enzymatically active or, if not, they bear at least one immune epitope in common with enzymatically active sialyltransferase.

Amino acid sequence variants of sialyltransferase fall into one or more of three classes: substitutional, insertional or deletional variants. These variants ordinarily are prepared by site specific mutagenesis of nucleotides in the DNA encoding the sialyltransferase, thereby producing DNA encoding the variant, and thereafter expressing the DNA in recombinant cell culture. However, variant sialyltransferase fragments having up to about 100–150 residues may be conveniently prepared using in vitro synthesis. Amino acid sequence variants are characterized by the predetermined nature of the variation, a feature that sets them apart from naturally occurring allelic or interspecies variation of the sialyltransferase amino acid sequence. The variants in the conserved region of homology typically exhibit the same qualitative biological activity as the naturally-occurring analogue.

While the site for introducing an amino acid sequence variation is predetermined, the mutation per se need not be predetermined. For example, in order to optimize the performance of a mutation at a given site, random mutagenesis may be conducted at the target codon or region and the expressed sialyltransferase variants screened for the optimal combination of desired activity. Techniques for making substitution mutations at predetermined sites in DNA having a known sequence are well known, for example M13 primer mutagenesis or PCR based mutagenesis.

Amino acid substitutions are typically of single residues; insertions usually will be on the order of about from 1 to 10 amino acid residues; and deletions will range from about 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that will be made in the DNA encoding the variant sialyltransferase must not place the sequence out of reading frame and preferably will not create complementary regions that could produce secondary mRNA structure (EP 75,444A).

Substitutional variants are those in which at least one residue in the FIGS. 1, 2, 14, 16 or 17 sequences has been removed and a different residue inserted in its place. Such substitutions generally are made in accordance with the following Table 1 when it is desired to finely modulate the characteristics of sialyltransferase.

TABLE 1

| Original Residue | Exemplary Substitution |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in sialyltransferase properties will be those in which (a) hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g., glycine.

A major class of substitutional or deletional variants are those involving the transmembrane and/or cytoplasmic regions of sialyltransferase. The cytoplasmic domain of sialyltransferase is the sequence of amino acid residues commencing at the start codons shown in FIGS. 1 and 2 and continuing for approximately 11 additional residues. In the rat and porcine residues 10–28 and 12 through 27, respectively, are believed to serve as a stop transfer sequence. The conformational bends introduced by the Phe-Val-Arg-Asn (SEQ. ID. NO:19) and Pro-Met-Arg-Lys-Lys-Ser-Thr-Leu-Lys (SEQ. ID. NO: 20) residues in rat and porcine, respectively, and the electropositive character of those residues act, together with the transmembrane region described below, to bar transfer of sialyltransferase through the cell membrane.

The transmembrane region of sialyltransferase is located in the porcine sequence at about residues 12–27 (where Ala is +1 as shown in FIG. 2), and in the rat sequence at the analogous location. This region is a highly hydrophobic domain that is the proper size to span the lipid bilayer of the cellular membrane. It is believed to function in concert with the cytoplasmic domains to anchor sialyltransferase in the golgi or endoplasmic reticulum.

Deletion or substitution of either or both of the cytoplasmic and transmembrane domains will facilitate recovery of recombinant sialyltransferase by reducing its cellular or membrane lipid affinity and improving its water solubility so that detergents will not be required to maintain sialyltransferase in aqueous solution. (See for example U.S. Pat. No. 5,032,519 describing production of soluble β-galactoside α2,6-sialyltransferase which is specifically incorporated herein by reference.) Deletion of the cytoplasmic domain alone, while retaining the transmembrane sequence, will produce sialyltransferase which would be solubilized with detergent. The cytoplasmic domain-deleted sialyltransferase will be more likely to insert into membranes, thereby enabling one to target its enzymatic activity. Preferably, the cytoplasmic or transmembrane domains are deleted, rather than substituted (for example amino acids 1–33 in rat β2,3-N sialyltransferase for the stop transfer sequence to produce soluble sialyltransferase).

The cytoplasmic and/or transmembrane (C-T) deleted or substituted sialyltransferase can be synthesized directly in recombinant cell culture or as a fusion with a signal sequence, preferably a host-homologous signal. For example, in constructing a procaryotic expression vector the C-T domains are deleted in favor of the bacterial alkaline phosphatase, 1pp or heat stable enterotoxin II leaders, and for yeast the domains are substituted by the yeast invertase, alpha factor or acid phosphatase leaders. In mammalian cell expression the C-T domains are substituted by a mammalian cell viral secretory leader, for example the herpes simplex gD signal. When the secretory leader is “recognized” by the host, the host signal peptidase is capable of cleaving a fusion of the leader polypeptide fused at its C-terminus to C-T deleted sialyltransferase. The advantage of C-T deleted sialyltransferase is that it is capable of being secreted into the culture medium. This variant is water soluble and does not have an appreciable affinity for cell membrane lipids, thus considerably simplifying its recovery from recombinant cell culture.

The addition of detergent, such as a non-ionic detergent, can be used to solubilize, stabilize, and/or enhance the biological activity of proteins that contain a membrane anchoring sequence. For example, deoxycholic acid is a preferred detergent, and Tween, NP-40, and Triton X-100, as well as other detergents may be used. Selection of detergent is determined at the discretion of the practitioner based on the particular ambient conditions and the nature of the polypeptide(s) involved.

Substitutional or deletional mutagenesis is employed to eliminate N- or O-linked glycosylation sites. Alternatively, unglycosylated sialyltransferase is produced in recombinant prokaryotic cell culture. Deletions of cysteine or other labile residues also may be desirable, for example in increasing the oxidative stability of the sialyltransferase. Deletions or substitutions of potential proteolysis sites, e.g. dibasic residues such as Arg Arg, is accomplished by deleting one of the basic residues or substituting one by glutaminyl or histidyl resides.

Insertional amino acids sequence variants of sialyltransferase are those in which one or more amino acid residues are introduced into a predetermined site in the target sialyltransferase. Most commonly, insertional variants are fusions of heterologous proteins or polypeptides to the amino or carboxyl terminus of sialyltransferase.

DNA encoding sialyltransferase is obtained from other sources than rat or porcine by a) obtaining a cDNA library from various tissues such as the liver or submaxillary glands of the particular animal, b) conducting hybridization analysis with labeled DNA encoding the conserved region of homology of sialyltransferase or fragments thereof (usually, greater than 30 bp) in order to detect clones in the cDNA library containing homologous sequences, and c) analyzing the clones by restriction enzyme analysis and nucleic acid sequencing to identify full-length clones. If full length clones are not present in the library, then appropriate fragments may be recovered from the various clones and ligated at restriction sites common to the clones to assemble a full-length clone.

"Essentially free from" or "essentially pure" when used to describe the state of sialyltransferase produced by the invention means free of protein or other materials normally associated with sialyltransferase in its naturally occurring in vivo physiological milieu, as for example when sialyltransferase is obtained from blood and/or tissues by extraction and purification. Sialyltransferase produced by the method of the instant invention was greater than or equal to 95% sialyltransferase by weight of total protein; constituted a single saturated band (by Coomasie blue staining) on polyacrylamide gel electrophoresis; and had a specific activity of at least about 500 nmole/mg protein/min.

The terms "substantial similarity" or "substantial identity" as used herein denotes a characteristic of a polypeptide sequence or nucleic acid sequence, wherein the polypeptide sequence has at least 70 percent sequence identity compared to a reference sequence, and the nucleic acid sequence has at least 80 percent sequence identity compared to a reference sequence. The percentage of sequence identity is calculated excluding small deletions or additions which total less than 35 percent of the reference sequence. The reference sequence may be a subset of a larger sequence, such as those shown in FIGS. 1 and 2; however, the reference sequence is at least 18 nucleotides long in the case of polynucleotides, and at least 6 amino residues long in the case of a polypeptide.

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC no. 31537). These examples are illustrative rather than limiting.

Prokaryotes are also used for expression. The aforementioned strains, as well as E. coli W3110 (F$^-\lambda^-$, prototrophic, ATTC No. 27325), bacilli such as Bacillus subtilus, and other enterobacteriaceae such as Salmonella typhimurium or Serratia marcescans, and various pseudomonas species may be used.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, E. coli is typically transformed using pBR322, a plasmid derived from an E. coli species (Bolivar et al., Gene 2, 95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al., Nature, 275, 615 [1976]; and Goeddel et al., Nature, 281, 544 [1979]), alkaline phosphatase, the tryptophan (trp) promoter system (Goeddel, D., Nucleic Acids Res. 8, 4057 [1980]) and hybrid promoters such as the tac promoter (de Boer, H., PNAS (USA) 80, 21–25 [1983]). However, other functional bacterial promoters are suitable. Their nucleotide sequences are generally known, thereby enabling a skilled worker operably to ligate them to DNA encoding sialyltransferase (Siebenlist et al., Cell 2 [1980]) using linkers or adaptors to supply any required restriction sites. Promoters for use in bacterial systems also will contain a Shine-Dalgarno (S.D.) sequence operably linked to the DNA encoding sialyltransferase.

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (Stinchomb et al., Nature 282, 39 [1979]; Kingsman et al., Gene 7, 141 [1979]; Tschemper et al., Gene 10, 157 [1980]) is commonly used. This plasmid already contains the trpl gene which provides a selection marker for a mutant strain of yeast lacking the ability to grow in tryptophan, for example ATCC no. 44076 or PEP4-1 (Jones, Genetics 85, 12 [1977]). The presence of the trpl lesion as a characteristic of the yeast host cell genome then provides an effective environment for detecting transformation by growth in the absence of tryptophan.

Suitable promoting sequences for use with yeast hosts include the promoters for 3-phosphoglycerate kinase (Hitzeman et al., J. Biol. Chem. 255, 2073 [1980]) or other glycolytic enzymes (Hess et al., J. Adv. Enzyme Reg. 7, 149 [1968]; and Holland, Biochemistry 17, 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the transcribed mRNA.

Preferred promoters controlling transcription from vectors in mammalian host cells may be obtained from various sources, for example, the genomes of viruses such as: polyoma, Simian Virus 40 (SV40), adenovirus, retroviruses, hepatitis-β virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273, 113 ([1978]). The immediate early promoter of the human cytomegalovirus is conveniently obtained as a HindIII E restriction fragment (Greenaway, P. J. et al., Gene 18 355–360 [1982]). Of course, promoters from the host cell or related species also are useful herein.

Transcription of a DNA encoding enkephalinase by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, L. et al., PNAS 78, 993 [1981]) and 3' (Lusky, M. L. et al., Mol. Cell Bio. 3, 1108 [1983]) to the transcription unit, within an intron (Banerji, J. L. et al., Cell 33, 729 [1983]) as well as within the coding sequence itself (Osborne, T. F. et al., Mol. Cell Bio. 4, 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding sialyltransferase. The 3' untranslated regions also include transcription termination sites.

Expression vectors may contain a selection gene, also termed a selectable marker. Examples of suitable selectable markers for mammalian cells are dihydrofolate reductase (DHFR), ornithine decarboxylase, multiple drug resistance biochemical marker, adenosine deaminase, asparagine synthetase, glutamine synthetase, thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because those cells lack certain genes necessary for a complete nucleotide synthesis pathway, they cannot survive unless the missing nucleotide synthesis pathway, are provided in a supplemented media. An alternative to supplementing the media is to introduce an intact DHFR or TK gene into cells lacking the respective genes, thus altering their growth requirement. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern, P. and Berg, P., J. Molec. Appl. Genet, 1, 327 [1982]), mycophenolic acid (Mulligan, R. C. and Berg, P., Science 209, 1422 [1980]) or hygromycin (Sugden, B. et al., Mol. Cell Biol. 5, 410–413 [1985]). The three examples given above employ bacterial genes under eukaryotic control to convey resistance to the appropriate drug G418 or neomycin (genticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the accumulation of multiple copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene by cointegration is referred to as coamplification. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene, replication of this gene gives often rise to replication of the gene encoding the desired protein. The result is that increased copies of the gene, i.e. an amplified gene, encoding the desired heterologous protein express more of the desired heterologous protein.

Preferred suitable host cells for expressing the vectors of this invention encoding sialyltransferase in higher eukaryotes include: monkey kidney CV1 line transformed by SV40 (COS-7, ATCC CRL 1651); human embryonic kidney line (293) (Graham, F. L. et al., J. Gen. Virol. 36, 59 [1977]); baby hamster kidney cells (BHK, ATCC CCL 10); chinese hamster ovary-cells-DHFR (CHO, Urlaub and Chasin, PNAS (USA) 77, 4216 [1980]); mouse sertoli cells (TM4, Mather, J. P., Biol. Reprod. 23, 243–251 [1980]); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N. Y. Acad. Sci. 383, 44–46 [1982]); baculovirus cells.

"Transformation" means introducing DNA into an organism so that the DNA is replicable, either as an extrachromosomal element or by chromosomal integration. Unless indicated otherwise, the method used herein for transformation of the host cells is the method of Graham, F. and Van der Eb, A., Virology 52, 456–457 [(1973]. However, other methods for introducing DNA into cells such as by nuclear ingestion or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. USA 69, 2110 [1972].

For analysis to confirm correct sequences in plasmids constructed, the ligation mixtures are used to transform *E coli* K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9, 309 [1981] or by the method of Maxam et al., Methods in Enzymology 65, 449 [1980].

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinary skilled artisan.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described in Goeddel, D. et al., Nucleic Acids Res., 8, 4057 [1980].

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (Maniatis, T. et al., *Molecular Cloning* pp. 133–134 [1982]). Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated. Construction of suitable vectors containing the desired coding and control sequences employ standard ligation techniques. Isolated plasmids or DNA fragments are cleaved, tailored, and relegated in the form desired to form the plasmids required.

"Filling in" or "blunt ending" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminis. Typically, blunt ending is accomplished by incubating 2–15 μg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 μM of each of the four deocynucleoside triphosphates. The incubation generally is terminated after 30 min. by phenol and chloroform extraction and ethanol precipitation.

Polynucleotides corresponding to or complementary to portions of the disclosed sequences can be used as hybridization probes to identify and/or isolate the respective germline genes. Such polynucleotides can also be used as hybridization probes to screen cDNA and genomic libraries to isolate cDNAs and genes encoding polypeptides that are structurally and/or evolutionarily related to the sialyltransferase sequences of the invention. Alternatively, such polynucleotides may serve as primers for amplification of germline gene sequences or related sequences by polymerase chain reaction (PCR).

Hybridization probes used for identifying and isolating additional sialyltransferase cDNA species are designed on the basis of the nucleotide and deduced amino acid sequences shown in FIGS. 1 and 2. Hybridization probes, which are typically labeled by incorporation of a radioisotope, may consist of one or more pools of degenerate oligonucleotides that encode all or a portion of the conserved region corresponding to the 55 residue segment spanning from amino acid residue 134 to amino acid residue 189 in the porcine α2, 3-0 sialylytransferase (FIG. 1). In particular, the heptapeptide motif -Asp-Val-Gly-Ser-Lys-Thr-Thr- is highly conserved and hybridization probes containing degenerate oligonucleotides encoding this motif, or variants of this motif wherein one or two amino acids are modified such that at least about 4 or 5 amino acids of the heptapeptide remain. Degenerate oligonucleotide probes encoding single or double amino acid substitution variants of the heptapeptide motif are also useful for screening for related sialyltransferase cDNA species. In addition to degenerate oligonucleotides, fragments of cloned polynucleotides, such as those depicted in FIGS. 1 and 2, may be employed as probes; it is preferred that such probes span the heptapeptide motif and, where desired, the conserved 55 amino acid residue segment described above.

Genomic or cDNA clones encoding sialyltransferases may be isolated from clone libraries using hybridization probes designed on the basis of sialyltranferase nucleotide sequences such as those shown in FIGS. 1 and 2. Where a cDNA clone is desired, clone libraries containing cDNA derived from cell expressing sialyltransferase(s) is preferred. Alternatively, synthetic polynucleotide sequences corresponding to all or part of the sequences shown in FIGS. 1 and 2 may be constructed by chemical synthesis of oligonucleotides. Additionally, polymerase chain reaction (PCR) using primers based on the sequence data disclosed in FIGS. 1 and 2 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIGS. 1 and 2 and a second primer that is not based on that sequence data may be used. For example, a second primer that is homologous to or complementary to a polyadenylation segment may be used.

It is apparent to one of skill in the art that nucleotide substitutions, deletions, and additions may be incorporated into the polynucleotides of the invention. However, such nucleotide substitutions, deletions, and additions should not substantially disrupt the ability of the polynucleotide to hybridize to one of the polynucleotide sequences shown in FIGS. 1 and 2 under hybridization conditions that are sufficiently stringent to result in specific hybridization.

The nucleotide and amino acid sequences shown in the Figures enable those of skill in the art to produce polypeptides corresponding to all or part of the encoded polypeptide sequences. Such polypeptides may be produced in prokaryotic or eukaryotic host cells by expression of polynucleotides encoding full-length sialyltransferase(s) or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments of sialyltransferases may be prepared by those of skill in the art. Preferred amino- and carboxy-termini of fragments or analogs occur near boundaries of structural and/or functional domains, for example, near an enzyme active site. Fragments comprising substantially one or more functional domain may be fused to heterologous polypeptide sequences, wherein the resultant fusion protein exhibits the functional property(ies), such as an enzymatic activity, conferred by the fragment. Alternatively, deletion polypeptides wherein one or more functional domain have been deleted exhibit a loss of the property normally conferred by the missing fragment.

Baculovirus eukaryotic gene expression is one of the most efficient means of generating large amounts of functionally active protein from cloned genes (Summers, M. and Luckow, V. (1988) *Bio/Technology* 6: 47, which is incorporated herein by reference). Sialyltransferase polypeptides of the invention may be produced from cloned polynucleotides by expression in a baculovirus expression system (Invitrogen Corporation, San Diego, Calif).

Figures 5, 7:
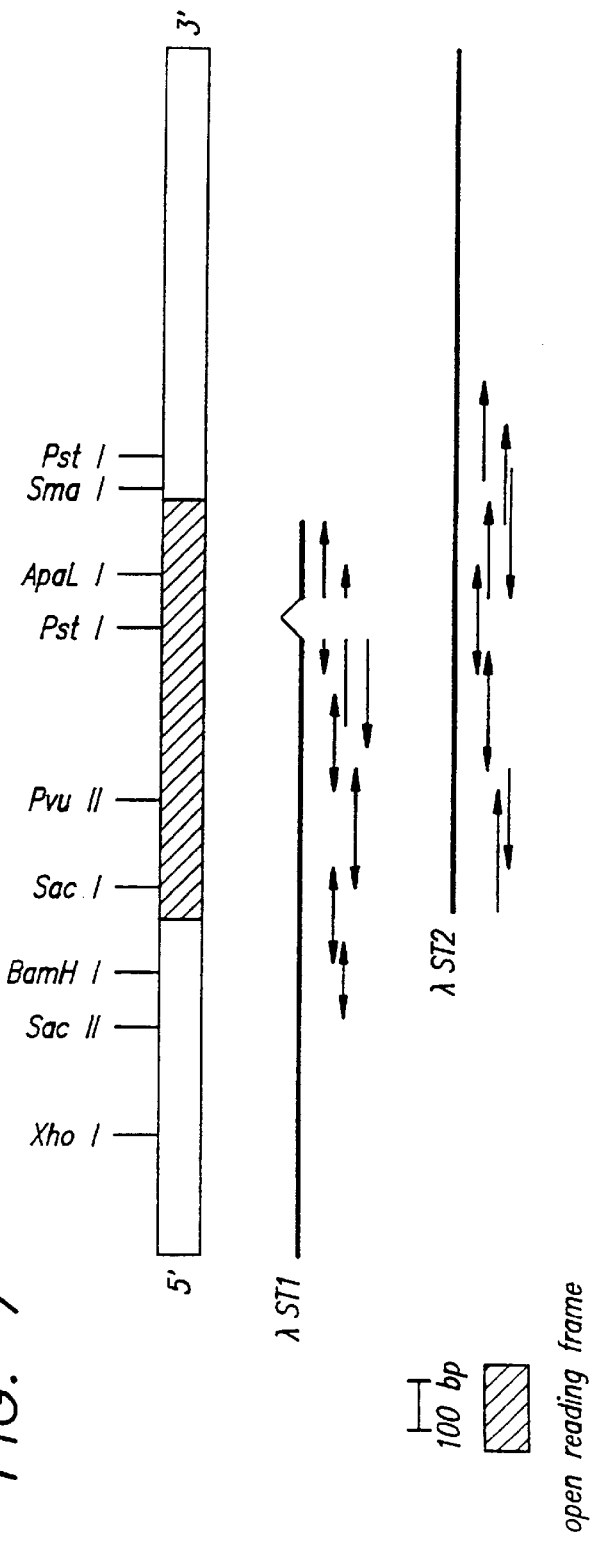
FIG. 5 $NH_2$-terminal amino acid sequences of the 48 kDa and 45 kDa α2,3-O sialyltransferase peptides. The 16 hydrophobic amino acids near the $NH_2$-terminus of the 48 kDa peptide, comprising the putative signal-anchor domain, are underlined (SEQ. ID. NOS:6 and 13).
FIG. 7 Restriction map and sequencing strategy of two α2,3-O sialyltransferase cDNA clones.

A typical sialyltransferase and its recombinant expression product is obtained according to the following protocol:

1. Porcine liver sialyltransferase was purified to apparent homogeneity.
2. The N-terminal amino acid sequence of porcine sialyltransferase was determined.
3. Oligonucleotide probes corresponding to 18 amino acids near the $NH_2$ terminal sequence were chemically synthesized.
4. cDNA libraries were constructed in λgt10, using a) randomly primed polyA+ enriched mRNA from porcine submaxillary glands, b) oligo dT primed polyA+ enriched mRNA from rat liver and c) oligo dT primed poly A+ enriched mRNA from rat brain.
5. A pool of radiolabeled synthetic deoxyligonucleotides complementary to codons for amino acid sequences of sialyltransferase were used, as described below, such as:
   a) 5' ACC CTG AAG CTG CGC ACC CTG CTG GTG CTG TTC ATC TTC CTG ACC TCC TTC TT 3'
   b) 5' GAC GTC GGG AGC AAG ACC ACC 3'
6. The randomly primed porcine submaxillary library was screened using the chemically synthesized oligonucleotide long and short probes labelled using polynucleotide kinase and $^{32}$P-ATP. Double positive plaques were purified and inserts sequenced.
7. One $^{32}$P labelled insert was used to rescreen the oligo dT primed porcine submaxillary libraries.
8. The complete reading frame for porcine sialyltransferase was obtained from two overlapping clones. The cDNA from rat liver and brain contained the conserved region of homology as determined by DNA sequence analysis of the cloned obtained.
9. A full length cDNA encoding porcine sialyltransferase was constructed from two overlapping clones in a plasmid and sequenced. It should be appreciated that disclosure of the DNA sequences in FIGS. 1 and 2 enables one to prepare probes from the conserved region of homology of sialyltransferase cDNA, thereby considerably simplifying and increasing the efficiency of probing cDNA or genomic libraries from these or other species as well as other tissues from these or other species, making it possible to dispense with sialyltransferase purification, sequencing, and the preparation of probe pools.
10. The full length cDNA encoding porcine and rat sialyltransferase was then tailored into an expression vehicle which was used to transform an appropriate host cell, which was then grown in a culture to produce the desired sialyltransferase.
11. Biologically active mature sialyltransferase produced according to the foregoing procedure may have alternative forms as shown in FIGS. 4 and 5, which result in two embodiments of 45 kDa and 48 kDa molecular weight.

Polynucleotides of the invention and recombinantly produced sialyltransferase polypeptides and fragments or amino acid substituted variants thereof may be prepared on the basis of the sequence data provided in FIGS. 1, 2, 3, 5, 7, and 8, or on the basis of sequence data obtained from novel sialyltransferase cDNAs isolated by methods of the invention. The production of polynucleotides and recombinantly produced sialyltransferase polypeptides is performed according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference. Polynucleotide sequences can be expressed in hosts after the sequences have been "operably linked" to (i.e., positioned to ensure the functioning of) an expression control sequence, so that transcription of the polynucleotide sequence occurs under suitable conditions for transcription.

"Specific hybridization" is defined herein as the formation of hybrids between a probe polynucleotide (e.g., a polynucleotide of the invention which may include substitutions, deletion, and/or additions) and a specific target polynucleotide (e.g., a polynucleotide having a complementary sequence), wherein the probe preferentially hybridizes to the specific target such that, for example, a single band can be identified on a Northern blot of RNA prepared from eukaryotic cells that contain the target RNA and/or a single major PCR product is obtained when the probe polynucleotide is used as a PCR primer. In some instances, a target sequence may be present in more than one target polynucleotide species (e.g., a particular target sequence may occur in multiple members of a sialyltransferase gene family or in alternatively-spliced RNAs transcribed from the same gene). It is evident that optimal hybridization conditions will vary depending upon the sequence composition and length(s) of the probe(s) and target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

"Antisense polynucleotides" are polynucleotides that: (1) are complementary to all or part of the sequences shown in FIGS. 1 and 2, and/or sequences obtained from novel sialyltransferase cDNAs isolated by methods of the invention, and (2) which specifically hybridize to a complementary target sequence. Such complementary antisense polynucleotides may include nucleotide substitutions, additions, deletions, or transpositions, so long as specific hybridization to the relevant target sequence (e.g., corresponding to FIGS. 1 or 2) is retained as a functional property of the polynucleotide. Complementary antisense polynucleotides include soluble antisense RNA or DNA oligonucleotides which can hybridize specifically to individual sialyltransferase mRNA species or to multiple members of a sialyltransferase mRNA family, and prevent transcription of the mRNA species and/or translation of the encoded polypeptide (Ching et al., *Proc. Natl. Acad. Sci. U.S.A.* 86:10006–10010 (1989); Broder et al., *Ann. Int. Med.* 113:604–618 (1990); Loreau et al., *FEBS Letters* 274:53–56 (1990); Holcenberg et al., WO91/11535; U.S. Ser. No. 07/530,165 ("New human CRIPTO gene"); WO91/09865; WO91/04753; WO90/13641; and EP 386563, each of which is incorporated herein by reference). The antisense polynucleotides therefore inhibit production of the encoded polypeptide(s). In this regard, antisense polynucleotides that inhibit transcription and/or translation of one or more sialyltransferases can alter the capacity and/or specificity of a cell to glycosylate polypeptides.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties, alternatively phosphorothiolates or O-methylribonucleotides may be used, and chimeric oligonucleotides may also be used (Dagle et al. (1990) *Nucleic Acids Res.* 18: 4751). For some applications, antisense oligonucleotides may comprise polyamide nucleic acids (Nielsen et al. (1991) *Science* 254: 1497). For general methods relating to antisense polynucleotides, see Antisense RNA and DNA, (1988), D. A. Melton, Ed., Cold Spring Harbor Laboratory, Cold Spring Harbor, N.Y.).

Antisense polynucleotides complementary to one or more sequences are employed to inhibit translation of the cognate mRNA species and thereby effect a reduction in the amount of the respective encoded polypeptide. Such antisense polynucleotides can provide a therapeutic function by inhibiting the formation of one or more sialyltransferases in vivo.

Transgenic animals harboring one or more integrated copies of a sialyltransferase transgene can be constructed. Sialyltransferase transgenes are polynucleotides comprising a polynucleotide sequence that encodes a sialyltransferase protein or fragment operably linked to a functional promoter and linked to a selectable marker sequence, such a G-418 resistance gene.

It is possible, using genetic manipulation, to develop transgenic model systems and/or whole cell systems containing a sialyltransferase transgene for use, for example, as model systems for screening for drugs and evaluating drug effectiveness. Additionally, such model systems provide a tool for defining the underlying biochemistry of sialyltransferase metabolism, which thereby provides a basis for rational drug design and experimental testing.

One approach to creating transgenic animals is to target a mutation to the desired gene by homologous recombination in an embryonic stem (ES) cell line in vitro followed by microinjection of the modified ES cell line into a host blastocyst and subsequent incubation in a foster mother (see Frohman and Martin (1989) *Cell* 56:145). Alternatively, the technique of microinjection of the mutated gene, or a portion thereof, into a one-cell embryo followed by incubation in a foster mother can be used. Various uses of transgenic animals, particularly transgenic animals that express a naturally-occurring sialyltransferase protein, or fragment thereof, may be employed. Alternatively, transgenic animals harboring transgenes that encode mutationally altered (e.g., mutagenized) sialyltransferase protein(s) that may or may not have enzymatic activity can be constructed as desired. Additional methods for producing transgenic animals are known in the art.

Alternatively, site-directed mutagenesis and/or gene conversion can be used to mutate in vivo a sialyltransferase gene allele, either endogenous or transfected, such that the mutated allele encodes a variant sialyltransferase.

Alternatively, homologous recombination may be used to insert a sialyltransferase sequence into a host genome at a specific site, for example, at a corresponding host sialyltransferase locus. In one type of homologous recombination, one or more host sequence(s) are replaced; for example, a host sialyltransferase allele (or portion thereof) is replaced with a mutated sialyltransferase sequence (or portion thereof). In addition to such gene replacement methods, homologous recombination may be used to target a polynucleotide encoding a sialyltransferase (or fragment thereof) to a specific site other than a host sialyltransferase locus. Homologous recombination may be used to produce transgenic non-human animals and/or cells that incorporate mutated sialyltransferase alleles. Gene targeting may be used to disrupt and inactivate one or more endogenous sialyltransferase genes; these so-called "knock-out" transgenics have been described in the art for other genes (WO91/10741; Kuhn et al. (1991) Science 708: 707).

The following examples merely illustrate the best mode now known for practicing the invention, but should not be construed to limit the invention. All literature citations herein are expressly incorporated by reference.

EXAMPLE 1

Purification of Porcine Sialyltransferase Purification of Two Forms of the α2,3-0 Sialyltransferase The α-2,3-0 sialyltransferase was purified using a combination of two procedures described previously (Sadler, J. E. et al., J. Biol. Chem. 254, 4434–4443 [1979] and Conradt, H. S. et al., in Sialic Acids 1988 Proceedings of the Japanese-German Symposium on Sialic Acids (Schauer and Yamakawa, eds.) pp. 104–105, Verlag Wissenschaft and Bildung, Kiel [1988]). The enzyme was purified from a porcine liver Triton X-100 extract by affinity chromatography on three successive columns of CDP-hexanolamine agarose. The elution profile from the first and third purification steps are shown in FIG. 3 and FIG. 4, respectively. FIG. 3 shows that two peaks of sialyltransferase activity were observed in the elution profile of the first affinity column. These two peaks were separated by combining the indicated fractions into pools A and B, these two pools were subsequently found to be enriched in two different molecular weight forms of the α2,3-0 sialyltransferase.

The second round of affinity purification on each pool resulted in removal of most of the contaminating α2,6 sialyltransferase, which is also present in porcine liver (Sadler, J. E. et al., J. Biol. Chem. 254, 4434–4443 (1979]). After the third round of affinity chromatography, column fractions were analyzed and individual fractions were found to be enriched in the 48 kDa (FIG. 4A, fractions 4–6) or 45 kDa (FIG. 4B, fractions 2–6) molecular weight forms of the α2,3 sialyltransferase. These two protein species were designated Form A and Form B, respectively. The specific activity for peak fractions from both columns was 8–10 units/mg protein. The strong band (~44 kDa) visible in fraction 6 of FIG. 4 column A is not α2,3 sialyltransferase, since it represented one of the major contaminants in both pool A and pool B after the previous column since enzymatic activity was absent on the final affinity chromatography step.

Sialyltransferase activity was assayed with lactose and/or low molecular weight antifreeze glycoprotein as substrates (Sadler, J. E. et al., J. Biol. Chem. 254, 4434–4443 [1979]).

The enzyme was purified from porcine liver following described methods (Sadler, J. E. et al., J. Biol. Chem. 254, 4434–4443 [1979] and Conradt, H. S. et al., in Sialic Acids 1988 Proceedings of the Japanese-German Symposium on Sialic Acids (Schauer and Yamakawa, eds.) pp. 104–105, Verlag Wissenschaft and Bildung, Kiel [1988]) with some modifications. Briefly, 2 kg of liver was homogenized in a buffer and membranes were prepared as described (Sadler, J. E. et al., J. Biol. Chem. 254, 4434–4443 [1979]). The membranes were extracted three times with buffer (Conradt, H. S. et al., in Sialic Acids 1988 Proceedings of the Japanese-German Symposium on Sialic Acids (Schauer and Yamakawa, eds.) pp. 104–105, Verlag Wissenschaft and Bildung, Kiel [1988]) and the extract was passed over a 1.5 l CDP-hexanolamine agarose column (column 1) (16 umol/ml). After washing the column with 3 L buffer B, the column was eluted with a linear gradient of 0.05 to 1.0 M KCL (2.5 l×2.5 l) in buffer B. Fractions containing α2,3 sialyltransferase were combined into two pools A and B, representing the main part and the trailing end of the peak, respectively (see FIG. 3). The pools were dialysed against buffer B and subjected to another round of affinity chromatography on CDP-hexanolamine agarose (columns IIA and IIB). A 150 ml column was used for pool A and a 30 ml column was used for pool B; two preparations from column I (from total of 4 kg liver) were loaded on the same column in step II. The α2,3 sialyltransferase was eluted with a gradient of 0–2.0 mM CTP (750 ml, pool A; 150 ml, pool B) in buffer B. Fractions with α2,3 sialyltransferase activity were desalted on G50 Sephadex, equilibrated in buffer, and active fractions were applied to 1.0 ml CDP-hexanolamine agarose columns (part III), which were eluted with step gradients of 0.1 to 1.0 mM CTP (20 steps, 1.0 ml each) in buffer B (see FIG. 2). Active fractions were pooled and the combined yield from both columns was 2.5 units at a specific activity of 8–10 units/mg protein.

The 48 kDa and 45 kDa sialyltransferase peptides (see FIG. 4) were resolved on SDS-polyacrylamide gels (Leammli, U. K., Nature 227, 680–685 [1970]), electro-eluted onto a PVDF membrane (Immobilon Transfer, Millipore) and stained with Coomasie Brilliant Blue (Sigma). The sialyltransferase bands were excised and the bound peptides were subjected to $NH_2$-terminal amino acid sequence analysis by Edman degradation using the Applied Biosystems 475A protein sequencer.

Fractions enriched in the 48 kDa (form A) and 45 kDa (form B) forms of the sialyltransferase were subjected to polyacrylamide gel electrophoresis (PAGE), blotted to a PVDF membrane, and analyzed by $NH_2$-terminal sequencing. Twenty two amino acid residues of sequence were obtained from each of the peptides (FIG. 5). The $NH_2$-terminal sequence of Form A contained a hydrophobic stretch of amino acids consistent with the prediction of Sadler et al. (J. Biol. Chem. 254, 4434–4443 [1979]) and Wescott et al. (J. Biol. Chem. 260, 13109–13121) that the smaller form was derived from the larger form by proteolytic cleavage of a hydrophosis peptide. This region was presumed to account for the detergent and membrane binding properties unique to Form A.

EXAMPLE 2

Porcine Sialyltransferase cDNA

Poly A+ RNA was used as a template for construction of single-stranded cDNA using a kit supplied by Invitrogen. The cDNA served as template in polymerase chain reaction (PCR) reactions using reagents and protocols supplied by Perkin Elmer Cetus. The specific conditions used were 92° for 1 min; 50° for 2 min; and 72° for 2 min. for denaturation, annealing and polymerization stays, respectively. PCR reactions were primed with 30 bp, oligonucleotides corresponding to sequences flanking the 120 bp deletion at the 3' end of ST1. The products of the amplification reaction were separated on a 2% agarose gel; two specific bands differing by 120 bp, corresponding to the ST1 and ST2 clones, were identified by ethidium bromide staining. These bands were eluted from the gel (Qiaex kit, Qiagen), subcloned into the TA vector (Invitrogen), and sequenced, as above, for unambiguous identification.

RNA Isolation and cDNA Library Construction.

Fresh porcine submaxillary glands (<30 min. postmortem) were frozen and transported in dry ice-EtOH. Total RNA was isolated according to the procedure of Chomczynski and Sacchi (Anal. Biochem. 162, 156–159 [1987]) Poly A+ RNA was purified by oligo dT-cellulose chromatography (Pharmacia). Double-stranded cDNA was synthesized by reverse transcription of the poly A+ RNA using random hexamers as primers with a Pharmacia cDNA synthesis kit and procedures recommended by the supplier. EcoRI adapters were ligated to EcoRI digested Igt10 and packaged in vitro (ProMega). The cDNA library was plated for screening by infection of E. coli C600 with the packaged mixture.

Isolation and Sequencing of cDNA Clones.

All procedures were performed according to Maniatis et al. (in Molecular Cloning: A Laboratory Manual, Cold Spring Harbor Laboratory, Cold Spring Harbor, N.Y. [1982]) unless otherwise specified. A 53 bp oligonucleotide probe (5'ACCCTGAAGCTGCGCACCCTGCTGGTGCTGTTCA TCTTCCTGACCTCCTTC TT3') (SEQ. ID. NO:22), corresponding to 18 amino acids near the $NH_2$-terminal sequence of the purified 48 kDa sialyltransferase peptide (see FIG. 5), was end-labeled with $^{32}P$ to a specific activity of $10^7$ cpm/pmole. 500,000 plaques were screened by nucleotide hybridization in the following prehybridization/hybridization solution: 5×SSC, 50 mM $NaH_2PO_4$ ph 6.7, 20% formamide, 5×Denhardt's solution, 0.1% SDS, 0.1 mg/ml salmon sperm DNA at 37° (Wood, W., in Guide to Molecular Cloning Techniques, Methods in Enzymology, pp. 443) Nitrocellulose filters (Schleicher and Schuell 0.45 m pore) were washed in 0.2×SSC, 0.1% SDS at 420 for 40 min. One strongly hybridizing clone, λST1, was obtained which contained an open reading frame which encoded amino acid sequence corresponding to the 48 kDa (SEQ. ID. NO:6) and 45 kDa (SEQ. ID. NO:13) purified sialyltransferase peptides. A second clone, λST2, was isolated by nucleotide hybridization using a restriction fragment probe from the 3' end of λST1. This probe, a 0.5 kb Pvu II- EcoRI restriction fragment, was labeled using a random priming kit and ($\alpha$-$^{32}P$ dCTP (Amersham).

EcoRI restriction fragments corresponding to the cDNA inserts of phage DNAs were subcloned into pUC vectors (Pharmacia). The subclones were sequenced using the T7 kit from Pharmacia. The sequence data was analyzed by computer using DNASTAR (DNASTAR Inc., WI, USA).

Several cloning strategies were attempted in order to clone the cDNA for the α2,3sialyltransferase, based on the amino acid sequence information presented in FIG. 5. In our first approach, we prepared the polymerase chain reaction primers in an attempt to generate a probe spanning the $NH_2$-terminal sequences of the 48 and 45 kDa protein species assuming that they were contiguous in the intact enzyme. In retrospect, this approach failed due to inaccuracies in the amino acid sequence obtained for the 45 kDa species (see FIGS. 5 and 6). Other failed attempts to obtain a positive clone utilized short (16–20 bp) degenerate oligonucleotides as probes to screen a porcine submaxillary gland cDNA. The approach that ultimately proved successful was to use a nondegenerate 53 bp oligonucleotide probe designed from a 17 amino acid region of the $NH_2$-terminus of the A form. The 53 bp probe was used to screen 500,000 plaques of a Igt10 porcine submaxillary salivary gland cDNA library. A single 1.6 kb clone was obtained, IST1, which had a consensus ATG start codon (Kozak, M., Cell 49, 283–292 [1986] and Kozak, M., Nuc. Acids Res. 12, 857–872 [1984]), an open reading frame encoding $NH_2$-terminal amino acid sequences of both Form A and Form B of the α2,3 sialyltransferase, and no in-frame stop codon. The fact that $NH_2$-terminal amino acid sequences from both forms of the α2,3 sialyltransferase were present in the translated open reading frame of λST1 indicated that the λST1 clone encoded a portion of the α2,3 sialyltransferase.

A 3' restriction fragment of λST1 was used as a probe to obtain a second, overlapping clone, λST2, from the same library (FIG. 7). λST2 completes the open reading frame originating in λST1. Together, these two cDNAs encode a single open reading frame (909–1029, see below), a 600 bp 5' untranslated region, and a 1000 bp 3' untranslated region. The nucleotide sequence as well as the translated amino acid sequence for the 1029 bp open reading frame is shown in FIG. 6. There was good agreement between the deduced amino acid sequence in the translated open reading frame of λST1 and the amino acid sequence obtained by direct analysis of the purified proteins.

The sequences of the overlapping regions of λST1 and λST2 are identical throughout their lengths except for a single 120 bp gap in λST1. The unique open reading frame continues on both sides of this interruption in λST1 (FIG. 6). To determine whether one or both of the two cDNA forms represented a true mRNA, PCR analysis using primers flanking this gap was performed on a cDNA template derived by reverse transcription of poly A+ RNA from porcine salivary glands. Amplified PCR fragments corresponding to λST1 and λST2 were detected by this approach (data not shown). The PCR products were subcloned and sequenced to confirm their identity, and both were found to be identical to the corresponding regions in λST1 and λST2. Thus, both direct cDNA cloning and PCR amplification results suggests that there are two mRNA specifies for the α2,3 sialyltransferase in porcine submaxillary glands which differ by the presence or absence of a 120 bp insertion in the open reading frame.

The predicted size of the sialyltransferase (1029 bp open reading frame) protein is 39 kDa., with 4 potential N-linked glycosylation sites (see FIG. 6) (Bouse, E., Biochem. J. 209, 331–336 [1983]). Utilization of 3 of these sites would yield a protein with a predicted size of approximately 48 kDa observed for Form A the purified sialyltransferase. Although the amino-terminal sequence contains two ATG codons in close proximity, only the first lies within a strong consensus translation initiation site (Kozak, M., Cell 49, 283–292 [1986] and Kozak, M., Nuc. Acids Res. 12, 857–872 [1984]). A Kyte-Doolittle hydropathy analysis (J. Mol. Biol. 157, 105–132 [1982]) reveals one potential membrane-spanning region consisting of 16 hydrophobic residues, located 11 residues from the amino-terminus (FIG. 6). This structural feature suggests that the α2,3 sialyltransferase, like the other glycosyltransferases which have been studied, has a type II membrane orientation and that this single hydrophobic region could serve as a non-cleavable, amino-terminal signal/anchor domain (Paulson, J. C. and Colley, K. J., J. Biol. Chem. 264, 17615–17618 [1989]).

The open reading frame encoded by λST1 and λST2 contains the entire NH$_2$-terminal amino acid sequences obtained from both Form A and Form B of the α2,3-0 sialyltransferase. As shown in FIG. 6, the NH$_2$-terminal sequence of Form A is found 8 amino acids from the putative start site of translation of the open reading frame, and the corresponding NH$_2$-terminal sequence of Form B is found 27 amino acids residues further toward the COOH-terminus of the protein. Since Form B of the α2,3 sialyltransferase is fully catalytically active (Rearick, J. I. et al., J. Biol. Chem. 254, 4444–4451 [1979]), the protein sequence between the putative initiator methionine of the full-length enzyme and the amino-terminus of Form B is presumably not required for enzymatic activity. Thus, the proteolytically sensitive region of the α2,3-0 sialyltransferase that lies between the signal-anchor domain and the catalytic domain appears to be a stem region, as defined for previously studied glycosyltransferases (Weinstein, J. et al., J. Biol. Chem. 262, 17735–17743 [1987] and Paulson, J. C. and Colley, K. J., J. Biol. Chem. 264, 17615–17618 [1989]).

Twenty mg of total RNA from porcine or rat tissues was electrophoresed on a 1.0% agarose gel containing 2.2 M formaldehyde (26) and transferred to nitrocellulose filters (Schleicher and Schuell) as described. Nitrocellulose filters were hybridized with 32P-labeled cDNA probes and washed as described earlier.

EXAMPLE 3

Expression of Soluble Porcine Sialyltransferase

A secretable chimeric protein was made between the putative catalytic domain of the α2,3-0 sialyltransferase and insulin signal sequence by fusing the C-terminal 890 bp of clone λST2 to the N-terminal portion of the vector pGIR-199 (Hsueh et al., J. Biol. Chem. 261, 4940–4947 [1986]) at a Sac I site contained in the reading frame of both vectors. This chimera, sp-ST, was digested with the restriction enzymes Nhe I and Sma I, the 1.0 kb fragment was isolated, and the subcloned into pSVL (Pharmacia) digested with Xba I and Sma I which cleave sites contained in the polylinker. The resulting construct was called pSVL-spST and was used as a vector for the transient expression of a soluble form of the α2,3-0 sialyltransferase in COS-1 cells. The supercoiled DNA, pSVL sp-ST, was transfected into COS-1 cells using lipofectin according to the procedure recommended by the supplier. (60 mm culture dish containing 50% confluent cells was transfected with 5 µg DNA, 20 ml lipofectin reagent). Forty-eight hours post-transfection the COS-1 cell media was collected and concentrated 15×on Centricon 30 filters (Amicon) for assay of α2,3-0 sialyltransferase activity. α2,3-0 sialyltransferase activity was determined using antifreeze glycoprotein acceptor as described previously (Sadler et al., J. Biol. Chem. 254, 4434–4443 [1979]).

Forty-eight hours post-transfection with pSVL-spST the COS cells (60 mm culture dish) were washed with met-free media (DMEM, 5% fetal calf serum) (Gibco) and cultured in the same media for 1 hr. The cells were pulse-labeled with 150 mCi/150 pmole of $^{35}$S-met Express label (NEN) in 1.5 mls met-free media for 2 hrs. These cells were then washed with PBS and chased for 5 hrs in media without $^{35}$S-met label. The media, containing secreted proteins, was then harvested, concentrated 15× and subjected to SDS-PAGE and analyzed by fluorography.

Figure 8:
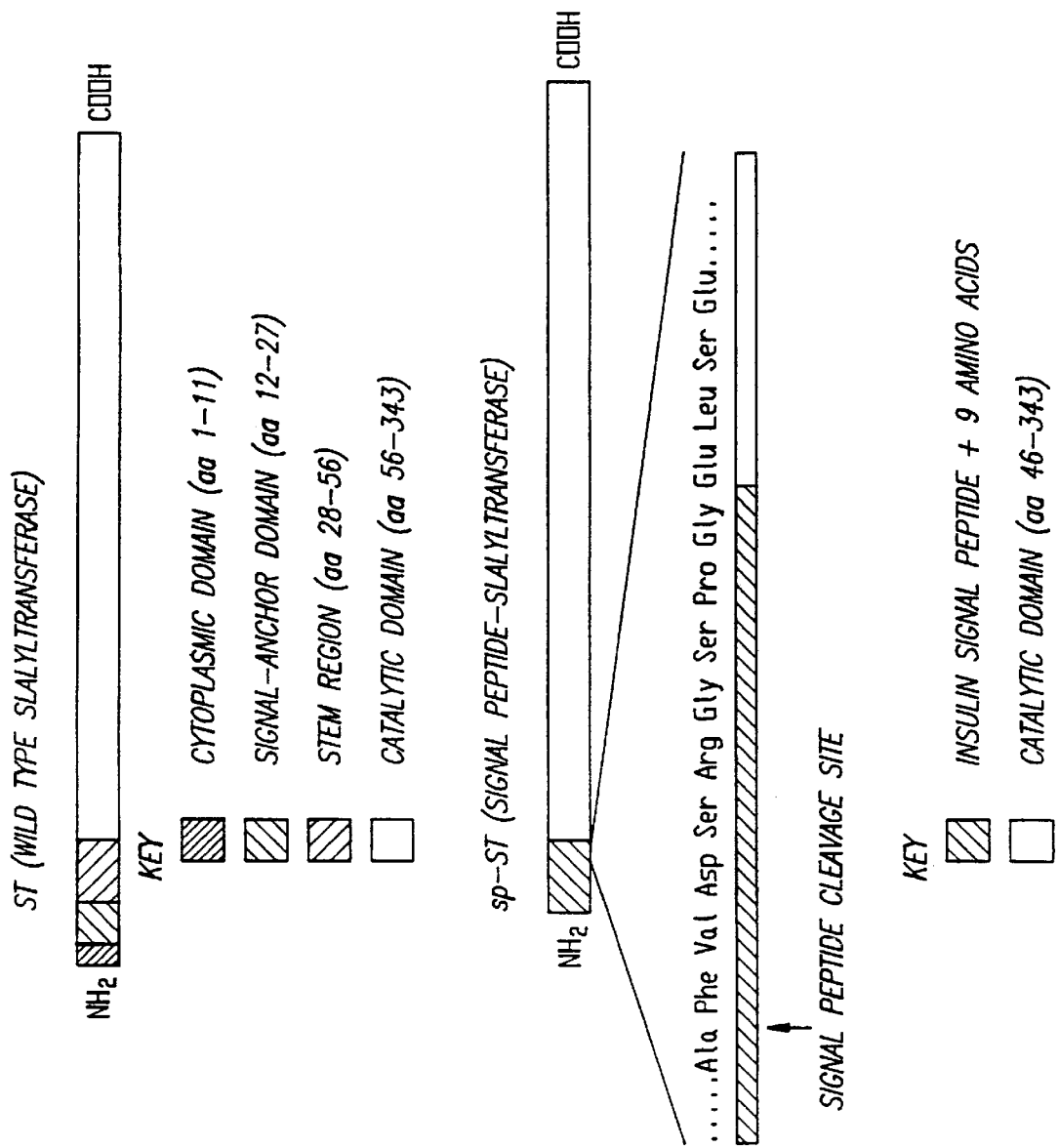
FIG. 8 Expression of a soluble, catalytically active α2,3-O sialyltransferase. A: A cDNA directing the expression of a soluble form of the α2,3-O sialyltransferase, sp-ST, was constructed by replacing the wild-type sialyltransferase cytoplasmic domain and signal anchor domain with the insulin signal peptide; sp-ST was predicted to encode a 38 kDa, secreted protein species when transfected into host cells. B: sp-ST was inserted into the expression vector PSVL and transfected into COS-1 cells; 48 post-transfection the cells were pulse-labeled for 2 hrs. in media containing Tran35S-label, followed by a 5 hr. chase period in media without label. This media was harvested, concentrated 15-fold, and analyzed by SDS-PAGE/fluorography. Duplicate samples of the sp-ST and mock-transfected cell media were analyzed. C: COS-1 cells were transfected with lipofectin (+ sp-ST) or lipofectin alone (mock) in an identical manner as 7B; 48 hrs. post-transfection the media was collected, concentrated 15-fold, and assayed for sialyltransferase activity with the specific acceptor substrate AFGP (Sadler, J. E. et al., J. Biol. Chem. 254, 4434–4443 [1979]. The amino acid sequence shown in FIG. 8 corresponds to SEQ. ID. NO.31.

As previously stated, the Form B of the α2,3-0 sialyltransferase is an enzymatically active, proteolytic cleavage product of the full-length, membrane-bound enzyme. Therefore, we anticipated that a soluble, chimeric protein would retain α2,3-0 sialyltransferase activity, if it included the entire sequence of the B form. To create such a soluble protein, a restriction site upstream of the NH$_2$-terminus of the B-peptide sequence was chosen as a site for fusion of the λST2 cDNA with a vector encoding the insulin signal sequence pGIR-199. As illustrated in FIG. 8, this construct encodes a fusion protein which we termed signal peptide -ST (sp-ST), which consists of the insulin signal sequence followed by 9 amino acids encoded by the pGIR linker, and the entire putative catalytic domain of the α2,3-0 sialyltransferase. The sp-ST construct was expected to direct the synthesis of a 38 kDa, secretable protein when transfected into host mammalian cells. A similar strategy for the production of soluble forms of glycosyltransferases has been used successfully (Paulson, J. C. and Colley, K. J., J. Biol. Chem. 264, 17615–17618 [1989]; Colley, K. J. et al., J. Biol. Chem. 264, 17619–17622 [1989]; Larsen, R. D. et al., Proc. Natl. Acad. Sci. USA 87, 6674–6678 [1990]).

The sp-ST construct was placed in the pSVL expression vector and transiently transfected into COS-1 cells. After 48 hours, the transfected cells were incubated for 2 hrs. in media containing Trans$^{35}$S-label followed by a 5 hr. chase period in media without label; this media was collected, concentrated 15-fold and analyzed by SDS-PAGE/fluorography. FIG. 9b shows that the media contains a prominent 38 kDa species, the expected size of the sp-ST protein. In parallel transfected cultures, the media was harvested 48 hours post-transfection, concentrated, and assayed for α2,3-0 sialyltransferase activity. As illustrated in FIG. 9c, media from cells transfected with sp-ST contained milliunits/ml of the sialyltransferase, while the media from the mock transfected cells had no significant activity.

EXAMPLE 4

Purification and Sequencing of Rat Liver Sialyltransferase

Like other glycosyltransferases which are resident membrane proteins of the endoplasmic reticulum and the Golgi apparatus, sialyltransferases are low abundance proteins and difficult to purify accounting for why only two members of this family have been cloned. The Galβ1,3(4)GlcNAc α2,3-sialyltransferase ("α2,3-N") was first purified 800,000 fold from rat liver in 1982 by Weinstein et al., yielding about 10 µg/ng tissue (Weinstein, J. et al., J. Biol. Chem. 257, 13835–13844 [1982] and Weinstein, J. et al., J. Biol. Chem. 13845–13853 [1982]). Although several attempts were made to obtain amino acid sequence information or raise an antibody against the enzyme using conventional methods, they failed because of the small amounts of dilute protein that could be obtained. As an alternative mass spectrometry has played an increasing role in structure elucidation of biologically important macromolecules. The development of new ionization methods and instrumentation has expanded the accessible mass range and detection sensitivity. High performance tandem mass spectrometry is now established as a powerful technique for protein sequencing (Mathews, W. R. et al., J. Biol. Chem. 262, 7537–7545 [1987]), as well as for determining post-translational and chemical modifications (Dever, T. E. et al., J. Biol. Chem. 264, 20518–20525 [1989]; Settineri, C. A. et al., Biomed. Environ. Mass Spectrom. 19, 665–676 [1990]; and DeWolf Jr., W. E. et al., Biochem. 27, 90993–9101 [1988]). Therefore, mass spectrometry was employed to provide amino acid sequence of sialyltransferase.

Reduction and carboxymethylation—Approximately 13 µg of Galβ1,3(4)GlcNAc α2,3-sialyltransferase (α2,3N) was stored in 350 ml 30 mM sodium cacodylate (pH=6.5), 100 mM NaCl 0.1% Triton CF-54 and 50% glycerol. TrisHCl (pH=8.0), quanidineHCl and dithiothreitol were added to final concentrations of 0.2 M, 6 M and 7 mM, respectively. The reduction was carried out at 60° C., under argon, for 1.5 hrs. Sodium iodoacetate (1.32 mg) was added in 2.5 ml of 0.2 M TrisHCl buffer to the mixture. The alkylation was carried out at room temperature, under argon, in the dark, for 1.5 hrs.

Dialysis—The reduced and carboxymethylated α2,3N was dialysed against 4 liter of 50 mM N-ethyl-morpholine acetate buffer (pH=8.1) using a Bethesda Research Labs ("BRL") Microdialysis System with BRL Prepared Dialysis Membrane with a molecular weight cutoff of 12–14 kDa. When the dialysis was complete, 10% SDS was added to the dialysis wells, resulting in a final SDS concentration of approximately 0.1%. The contents of the wells were pooled and dried using a SpeedVac Concentrator (Savant). To remove the SDS, Konigsberg precipitation was carried out (Konigsberg, W. H., Henderson, L., Methods in Enzymology 91, 254–259 [1993]).

Tryptic digestion—The precipitated α2,3N was dissolved in digestion buffer (100 mM TrisHCl 2M urea, 1 mM CaC12, pH=8.0), yielding a protein concentration of approximately 2 mg/ml. The α2,3N was digested with 10% trypsin (w/w) (Boehringer-Mannheim, sequencing grade, dissolved in 1mM HC1) at 37° C. After 7 hrs. of digestion another aliquot of trypsin was added to the mixture, resulting in a final trypsin concentration of approximately 13%. The digestion was stopped after 18 hrs. The resulting tryptic digestion was separated by reverse phase HPLC (ABI C18 column, 1.0× 100 mm) using an ABI 140A solvent delivery system. Solvent A was 0.1% TFA in water. Solvent B was 0.08% TFA in 70% acetonitrile/30% water. The system operated at a flow rate of 50 ml/min. Ten minutes after the injection, the percentage of solvent B was increased from 0% to 50% over 90 minutes, then up to 100% in 30 minutes. Peptides were detected using an ABI 783A absorbance detector, operating at 215 nm. Some of the fractions were esterified using an HCl/n-hexanol mixture.

Mass spectrometry—Liquid Secondary Ion Mass Spectrometry (LSIMS) experiments were carried out using a Kratos MS50S double focusing mass spectrometer, fitted with a LSIMS source and a high field magnet. Approximately one-fifth of each collected fraction was loaded for LSIMS analysis. One microliter of a glycerol-thioglycerol 1:1 mixture acidified with 1% TFA was used as the liquid matrix. The samples were recollected from the probe tip. The most abundant molecular ions were chosen for collision induced dissociation (CID) analysis. These experiments were performed on a Kratos Concept IIHH four sector mass spectrometer, equipped with an electro-optical multichannel array detector, which can record sequential 4% segments of the mass range simultaneously. The collision energy was set at 4 keV, the collision gas was helium, and its pressure was adjusted to attenuate the abundance of the chosen precursor ion to 30% of its initial value. The remainder of each sample was loaded, and 1 ml of the above-mentioned matrix was added. The high energy CID data were interpreted without the aid of computer analysis.

Tandem mass spectrometry is a powerful method for protein sequencing, exhibiting advantages over conventional Edman techniques. Sequencing even equimolar mixtures is possible by this method. For mass spectrometry analysis the first few peptide fractions from HPLC were esterified to increase their hydrophobicity, thus improving their sputtering efficiency (Falick, A. M. and Maltby, D. A., Anal. Biochem. 182, 165–169 [1989]). LSIMS analysis of each fraction revealed multiple molecular ions, indicating the presence of more than one peptide in each. The most abundant 30 molecular ions were chosen for CID analysis. In these experiments, the 12C isotope peak of the ion of interest is chosen in the first mass spectrometer. Only the fragments of this species resulting from the dissociation induced by collision with helium in the collision cell, situated between the two mass spectrometers, are detected at the end of the second mass spectrometer. In high energy collision induced dissociation (CID) analysis fragmentation occurs mainly along the peptide backbone. Multiple cleavages, i.e., fragmentation in the amino acid side chains are also observed. The fragmentation along the peptide chain results in ion series which differ by amino acid residue weights, thus the corresponding amino acid sequence can be deduced. The high energy modes of fragmentation provide additional information about the amino acid identity, thus confirming the obtained sequences and permitting differentiation between the isobaric Leu/Ile amino acid pair (Johnson, R. S. et al., Anal. Chem. 59, 2621–2625 [1987]). Side chain fragmentation can be observed mostly when there is a basic amino acid, i.e., Arg, Lys or His, in the sequence (Johnson, R. S. et al., Int. J. Mass Spectrom. Ion Proc. 86, 137–154 [1988]). Commonly, preferential protonation of basic amino acid residues at or near to the N-terminus results in preferred charge retention on this end of the molecule. Peptides containing basic amino acids at or close to the C-terminus will show mostly C-terminal fragments. Thus, trypsin is advantageous for an initial digestion. Interpretation of high energy CID data eventually yielded 14 sequences (See Table 2 and FIG. 9).

Figure 9:
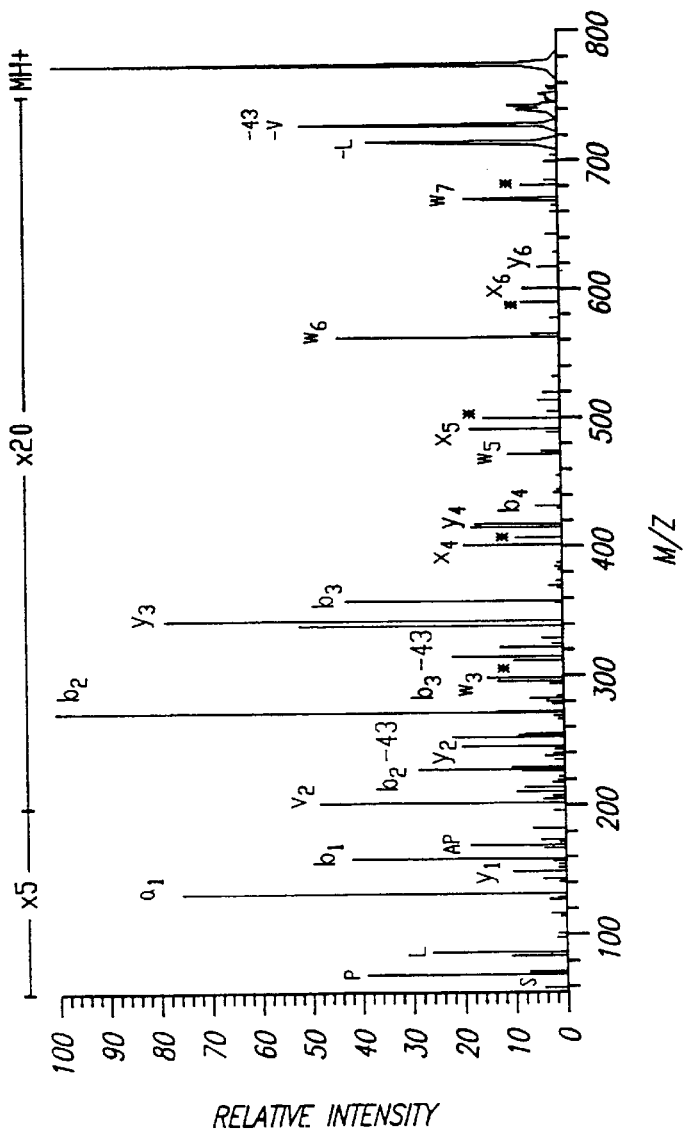
FIG. 9 CID spectrum of a carbamylated tryptic peptide from Gal α2,3-N sialyltransferase enzyme. The peptide sequence is Leu-Asn-Ser-Ala-Pro-Val-Lys (SEQ ID NO.32), $MH^{+-}$771.4. Fragmentation clearly indicates modification at the N-terminus and not at the ε-amino group of the lysine residue. An abundant ion at m/z 669 (w7) confirms the presence of an N-terminal leucine in this peptide. Ions labelled with asterisks are matrix related background ions (Falick et al. (1990) Rapid Commun. Mass Spectrom. 4: 318). Observed fragment ions are included in the table. Ions belonging to the same ion series are listed in rows.
Figure 10:
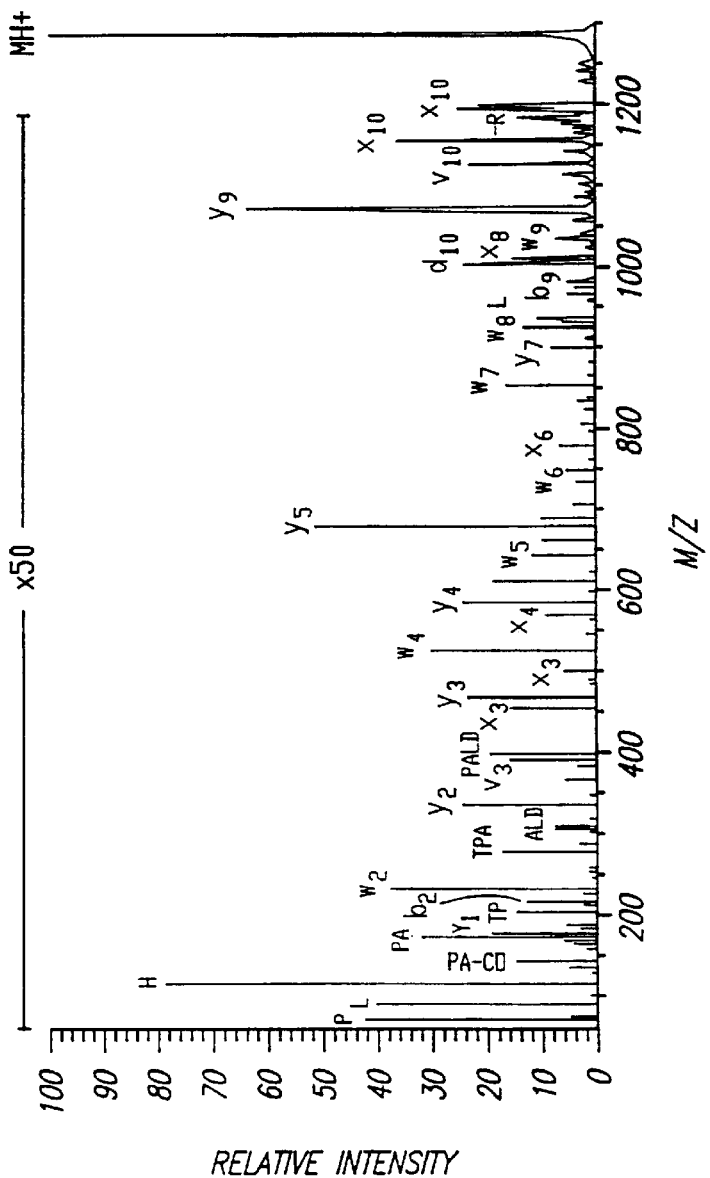
FIG. 10 CID spectrum of the longest sequenced tryptic peptide from Gal α2,3-N sialyltransferase enzyme. The peptide sequence is Leu-Thr-Pro-Ala-Leu-Asp-Ser-Leu-His-Cys*-Arg (SEQ ID NO.33), $MH^+$=1283.6. Cys* represents carboxymethyl cysteine. Ions with charge retention at the N terminus are labelled as a, b, c ions, and the C-terminal ions are designated as x, y, z fragments (Biemann, K. (1990) Meth. Enzymol. 193: 886–887). The first ions (a, x) are products of a cleavage between the α carbon and the carbonyl group. Ions y and b are formed when the peptide bond is cleaved. Ions c and z are present due to the cleavage between the amino group and the α carbon. The numbering of these fragments is always initiated at the respective terminus. The side-chain fragmentation occurs between the β and γ carbons of the amino acids, yielding the so-called d (N-terminal) and w (C-terminal) ions. Observed fragment ions are included in the table. Ions belonging to the same ion series are listed in rows.

The analysis of the CID spectra revealed that some side reactions occurred during the tryptic digestion. Two trypsin autolysis products were identified at m/z 659.3 and 1153.6 (FIG. 9). Because of the long incubation time and lack of a proper scavenger, some tryptic peptides were carbamylated at their N-termini. While such side reactions would preclude Edman degradation, N-terminal modifications may even be useful in mass spectrometric sequencing. In fact, the CID analysis of these modified peptides was helpful in confirming of some of the above mentioned sequences, in one case providing the means for differentiation between an N-terminal leucine or isoleucine (FIG. 10).

EXAMPLE 5

Rat Liver Sialyltransferase

PCR amplification of a specific cDNA probe—Based on the amino acid sequences of eleven of the fourteen peptides derived from the α2,3N, twenty two degenerate oligonucleotide pools of both sense and antisense strands were synthesized (Genosys). Initial PCR experiments were designed based on the observation that peptide 11 and peptide 1 are homologous to a region located near the center of the previously cloned sialyltransferase, the Galβ1,4GlcNAc α2,6-sialyltransferase (Weinstein, J. et al, J. Biol. Chem. 257, 13835–13844 [1982]) and the α2,3-0 described above (FIG. 11). Two groups of PCR experiments were performed using either a sense primer to peptide 11 or an antisense primer to peptide 1 paired with oligonucleotide primers to the other peptides and first strand cDNA synthesized from rat liver total RNA as a template. Beginning with a template melting step (5 minutes at 94° C.), the amplification was carried out, using GeneAmpTM DNA amplification reagent kit with AmpliTaqTM DNA polymerase (Perkin Elmer Cetus), by cycling 35 times, 1 minute at 94° C., 1 minute at 37° C., and 2 minutes at 72° C., and ended with a final extension step (15 minutes at 72° C.). Several cDNA fragments were generated from these PCR reactions. Assuming that peptide 11 and 1 represented a continuous stretch of amino acids, additional sets of PCR experiments were carried out utilizing a nested primer strategy (Mullis, K. B. and Faloona, F., Methods Enzymol. 155, 335–350 [1987]) in order to identify specific cDNA fragments. Using this approach a specific cDNA fragment, 11sense-14antisense (11s-14as), was identified. The 11s-14as cDNA fragment was subcloned into Bluescript plasmid (Stratagene) and sequenced using universal primers (Stratagene) and Sequenase Version 2.0 kit (USB).

Cloning of the sialyltransferase—A cDNA library was constructed from rat liver poly (A)+ RNA using a cDNA synthesis kit from Pharmacia (Gubler, U. and Hoffman, B. J. Gene 25, 263–269 [1983]). Oligo (dT) primed cDNA was synthesized and ligated to EcoRI-NotI linkers. cDNAs were then ligated into EcoRI cleaved Igt10 DNA (Promega). After in vitro packaging with a DNA packaging extract (Stratagene), phage were plated out on host strain E. coli C600 hfl- (Promega). Approximately one million plaques were screened with the 11s-14as cDNA probe (Gubler, U. and Hoffman, B. J. Gene 25, 263–269 [1983]). Two positive phage (18-1 and 9-1) were plaque purified and subcloned into Bluescript plasmid vector (Stratagene) for sequencing.

Figure 11:
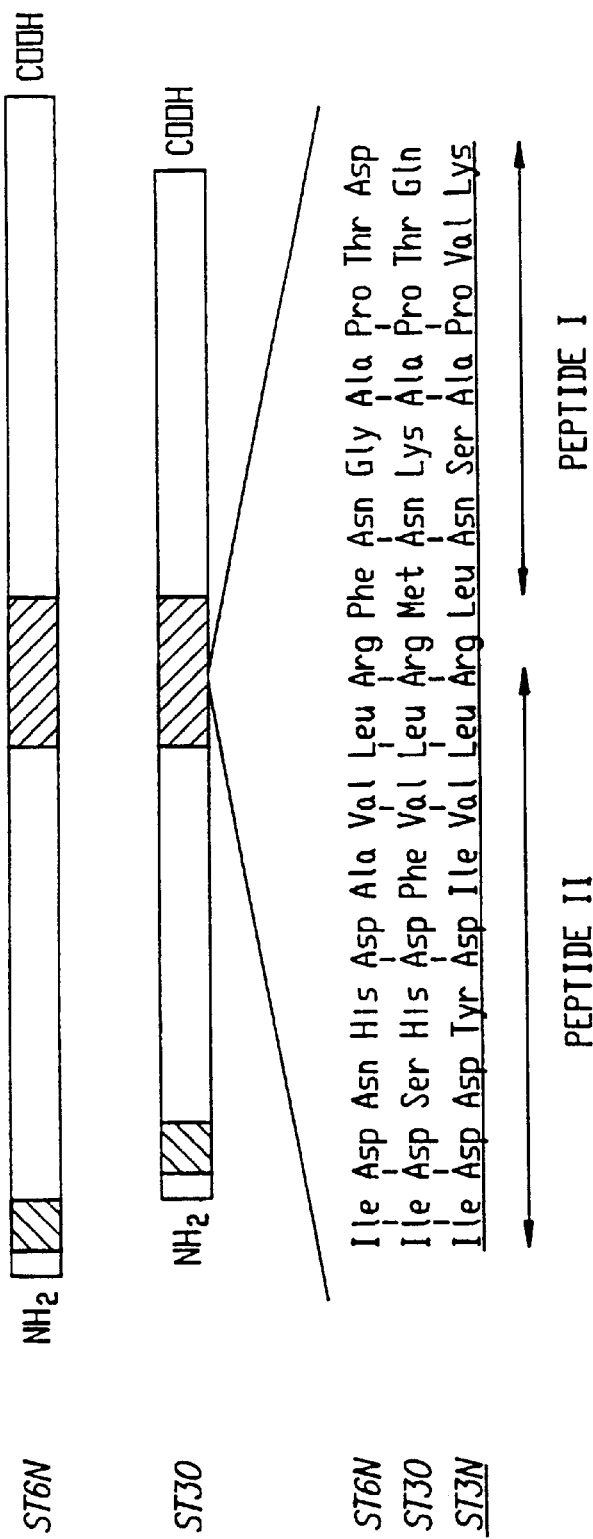
FIG. 11 Alignment of Peptides 1 and 11 derived from the Galβ1,3(4)GlcNAc α2,3-sialyltransferase (ST3N) (SEQ. ID. NO.36) with previously cloned sialyltransferases. Galβ1,4GlcNAc α2,6-sialyltransferase (ST6N) (SEQ. ID. NO.34) and Galβ1,3GalNAc α2,3-sialyltransferase (ST30) (SEQ. ID. NO.35) are shown as open bars. Solid box indicates signal-anchor sequence. Hatched box indicates the homologous region identified between the two sialyltransferases.

Isolation of cDNA Clones—The Dayhoff Protein database was used to screen the peptide sequences for homology with known proteins. This search provided the first evidence of homology between the α2,3-N and other cloned sialyltransferases. From this analysis, peptide 11 (Table 2) was found to be homologous to sequences present in both the rat and human β-galactoside a-2,6-sialyltransferases (these two enzymes are 88% conserved, Gu, T. J. et al., FEBS 275, 83–86 [1990] and Lance, P. et al., Biochem. Biophys. Res. Commun. 164, 225–232 [1989]). When this analysis was extended to include the sequence of porcine α2,3-O (SEQ. ID. NO:2), an additional peptide, peptide 1 (Table 2), was found to be homologous to sequences in both the cloned sialyltransferases. The alignment of these peptides with the sequences present in the previously cloned sialyltransferases suggested that these two peptides represented a continuous stretch of amino acids that had been cleaved at the arginine residue during the trypsin digestion (FIG. 11).

TABLE 2

Amino Acid Sequences of Peptides Derived from the Galβ1,3,(4)GlcNAc α2,3-Sialyltransferase

| Peptide | Amino Acid Sequence | Residue position in Gal α2,3-ST (FIG. 4) |
|---|---|---|
| 1 | LeuAsnSerAlaProValLys | 186–192 |
| 2 | MetAlaAlaIleLys | 340–344 |
| 3 | GluProProGluIleArg | 264–269 |
| 4 | Gly*Lys*AspAsnLeuIleLys | 130–136 |
| 5 | LeuProAlaGluLeuAlaThrLys | 69–76 |
| 6 | AlaIleLeuSerValThrLys | 137–143 |
| 7 | IleLeuAsnProTyr | 270–274 |
| 8 | LeuThrProAlaLeuAspSerLeuHisCysArg | 147–157 |
| 9 | ValSerAlaSerAspGlyPheTrpLys | 247–255 |
| 10 | ValIleThrAspLeuSerSerGlyIle | 366–374 |
| 11 | IleAspAspTyrAspIleValIleArg | 177–185 |
| 12 | GluPheValProProPheGlyIleLys | 121–129 |
| 13 | LeuGlyPheLeuLeuLys | 59–64 |
| 14 | AspSerLeuPheValLeuAlaGlyPheLys | 222–231 |

The underlined sequences show homology to the other known sialyltransferase enzymes (25,26).
The amino acid in italic is the only one different from the amino acid sequence deduced from the nucleotide sequence of the Gal α2,3-ST cDNA.

The recognition that peptide 11 and peptide 1 exhibited homology to a sequence previously identified as the conserved region of homology in the center of two other cloned sialyltransferases provided the basis for our cloning strategy (FIG. 11). We assumed that peptide 11 and peptide 1 might be near the center of the protein, thus PCR experiments were designed to generate a long cDNA probe. Based on the amino acid sequences of the 14 sialyltransferase peptides, degenerate oligonucleotide primers of both sense and anti-sense were synthesized for use in PCR experiments. In these experiments, primer 11 sense and 1 antisense were paired with other primers in attempt to amplify long cDNA fragments of the α2,3-N. Several cDNA fragments were amplified in these experiments. Assuming that peptide 11 and peptide 1 represented a continuous stretch of amino acids, primer 11 and primer 1 were then used in a nested primer strategy (Mullis, K. B. and Faloona, F., Methods Enzymol. 155, 335–350 [1987]) to identify specific cDNA fragments. The fragment amplified using the primers 11 sense and 14 antisense was nearly the same size as the fragment amplified using the 1 sense and 14 antisense primers, suggesting that the fragment produced was the result of specific annealing by the primers and not an artifact.

Cloning and characterization of the 11 sense-14 antisense fragment found that peptide 11 and 1 are indeed continuous. Comparison of the sequence of the cDNA fragment with the two cloned sialyltransferases (Weinstein, J. et al., J. Biol. Chem. 262, 17735–17743 [1987]), we found that the homology extends from peptide 1 and continuous for eighteen amino acids. Because of the homology, we believed that the 11s-14as cDNA fragment was amplified from a sialyltransferase mRNA. The sequence also indicated that the cDNA fragment was not a fragment of the Galb1,4GlcNAc α2,6-sialyltransferase which is abundant in rat liver (Weinstein, J. et al., J. Biol. Chem. 257, 13835–13844 [1982]).

The 11 sense-14 antisense fragment was used to screen an oligo dT primed rat liver cDNA library from which two positive clones were obtained from 1 million plaques screened. Characterization of the positive clones revealed that clone ST3N-1 contained a 2.1 Kb insert while clone ST3N-2 was considerably shorter, only 1.5 Kb in length. Northern analysis indicated that the Gal α2,3-ST mRNA was 2.5 Kb (see below), suggesting that clone ST3N-1 might contain the complete coding sequence of the Gal α2,3-ST. Primary Structure of the α2,3-N sialyltransferase—Sequence analysis revealed that clone ST3N-1 contained the complete open reading frame of the sialyltransferase (FIG. 2) (SEQ. ID. NO: 3). It consists of a 82 bp 5'-untranslated region, an open reading frame 1122 bp in length, a 3'-untranslated region of approximately 1 Kb and a poly (A) tail. The open reading frame of clone ST3N-1 codes a 374 amino acids protein with a predicted molecular weight of 42,033 (SEQ. ID. NO:4). With the exception of a single amino acid difference, the open reading frame encodes all of the 14 peptide sequences obtained from mass spectrometric analysis of the purified sialyltransferase. This confirms that the cDNA of clone ST3N-1 is indeed that of the sialyltransferase. As observed for other cloned glycosyltransferases (Paulson, J. C. and Colley, K. J., J. Biol. Chem. 264, 17615–17618 [1989]), the α2,3-N is predicted to have a short N-terminal cytoplasmic tail, a signal anchor sequence approximately of 20 residues, and a large C-terminal region that comprises the catalytic domain of the enzyme.

EXAMPLE 6

Expression of Soluble Rat Sialyltransferase

In order to produce a soluble form of the sialyltransferase for enzymatic characterization, a fusion protein containing the catalytic domain of the enzyme and the insulin cleavable signal sequence was constructed in the mammalian expression vector pSVL (Pharmacia). Specifically, the catalytic domain of the sialyltransferase was amplified by PCR using a 5' primer at the position +182 (FIG. 11), down stream of the transmembrane domain, and a 3' primer located in 3'UTR upstream of the polyadenylation site. PCR reactions were carried out as described above with annealing temperature at 55° C. The PCR product was subcloned into BamHI-EcoRI sites of pGIR-199 (a gift of K. Drickamer) resulting in a fusion of the sialyltransferase inframe to the insulin signal sequence present in the pGIR vector (Huseh, E. C. et al., J. Biol. Chem. 261, 4940–4947 [1986]). The resulting fusion protein was inserted into the Xba I-Sma I sites of the expression vector pSVL to yield the expression plasmid pBD122.

For transient expression in COS-1 cells, the expression plasmid pBD122 (20 mg) was transfected into COS-1 cells on 100 mm plates using lipofectin as suggested by the manufacturer (BRL). After 48 hrs., the cell culture media was collected and concentrated using a centricon 10 microconcentrator. The concentrated media was assayed for sialyltransferase activity using oligosaccharides as acceptor substrates. Transfer of sialic acid to the oligosaccharide was monitored using ion-exchange chromatography (Sadler, J. E. et al., J. Biol. Chem. 254, 5934–5941 [1979] and Paulson, J. C. et al., J. Biol. Chem. 264, 10931–10934 [1989]).

In order to demonstrate that clone ST3N-1 does encode α2,3-N sialyltransferase, we proceeded to express the clone in COS-1 cells. Amino acid sequence of clone ST3N-1 revealed that the protein contains an $NH_2$-terminal signal-anchor sequence which is predicted to anchor the enzyme to the Golgi apparatus in the cell (Paulson, J. C. and Colley, K. J., J. Biol. Chem. 264, 17615–17618 [1989]). To facilitate functional analysis of the enzyme, we wished to produce a soluble form of the enzyme which when expressed would be secreted from the cell. A fusion protein was constructed using the cleavable insulin signal sequence to replace the signal-anchor sequence at the $NH_2$-terminus of the sialyltransferase. When the expression plasmid pBD122 was expressed in COS-1 cells, the enzyme was secreted from the cells and exhibited sialyltransferase activity.

The enzymatic properties of α2,3-N sialyltransferase was first characterized with purified protein (Weinstein, J. et al., J. Biol. Chem. 257, 13845–13853 [1982]). The sialyltransferase was found to utilize β-galactoside acceptors containing either the Galβ1,3GlcNAc or the Galβ1,4GlcNAc sequences forming the NeuAcα2,3Galβ1,3GlcNAc and NeuAcα2,3Galβ1,4GlcNAc sequences often found to terminate complex type N-linked oligosaccharides. The enzyme secreted from the cells which were transfected with the expression plasmid pBD122 were capable of utilizing β-galactoside acceptors containing either the Galβ1,3GlcNAc or the Galβ1,4GlCNAc sequences (Table 2); cells transfected with the parental vector secreted no such sialyltransferase activity. The secreted enzyme is also capable of sialylating asialo-α1 acid glycoprotein. This data is consistent with the enzymatic properties of the purified α2,3-N.

EXAMPLE 7

Expression of α2,3-N Sialyltransferase in Baculovirus

The terminal tetrasaccharide sialyl Lewis$^x$ (Sle$^x$: SAα2,3Galβ1,4GlcNAc[α1,3Fuc]) has been identified as the ligand for P-selectin and E-selectin, and a synthetic oligosaccharide containing the SLe$^x$ structure is a candidate for blocking selectin-ligand interactions. Complete chemical synthesis of SLe$^x$ is technically and economically difficult, but usage of specific glycosyltranferases to attach the terminal sialic acid and fucose residues to chemically synthesized core saccharide will make synthesis of free SLe$^x$ feasible. The gene encoding α2,3-N sialyltransferase was cloned from a rat liver cDNA library, and was shown to have specific α2,3 (Galβ1,3/4GlcNAc) sialyltransferase activity when expressed in transfected COS-1 cells (Wen et al., manuscript in preparation). A portion of the cDNA clone encoding the enzymatic portion of the polypeptide, but lacking the hydrophobic signal/membrane anchor domain, was fused to the pre-insulin signal sequence to form a cDNA encoding a soluble, secreted α2,3 NST protein. This cDNA was cloned in a Baculovirus transfer vector and used to transfect Sf-9 insect cells in the presence of wild type baculovirus DNA. Recombinant virus containing α2,3-N sialyltransferase cDNA was isolated and purified and used to infect Sf-9 cells. Infected cells secreted α2,3 NST in large amounts into the medium, and this protein was purified by ion-exchange chromatography.

Sf-9 cells were purchased from ATCC. DNA vectors pGIR199 and pBlueBac were obtained from J. C. Paulson and Invitrogen (San Diego, Calif.), respectively. Sf-9 cells were grown in spinner culture at cell densities between 0.3 and 1.5 million cells per milliliter in Graces Insect Media (supplemented with 0.33% lactalbumin hydrolysate and 0.33% yeastolate), obtained from Gibco (Grand Island, N.Y.), plus 10% heat-inactivated fetal calf serum (JRH Biosciences, Lenexa, Kans.). This medium is designated GCMS+10% FCS.

A soluble form of α2,3-N sialyltransferase was made in the following manner. cDNA representing the entire α2,3-N sialyltransferase mRNA was used as template for PCR using as amplimers two oligonucleotides that hybridized (5') at a position just C-terminal of the combination signal/anchor region of the enzyme and (3') upstream of the poly(A) addition site in the 3' untranslated region. Both oligonucleotides encoded BamHI sites at their 5' ends, enabling the PCR products to be cloned at the BamHI site of pGIR199, fused in frame with the pre-insulin signal sequence. Flanking Nhel sites were used to liberate the gene fusion, and this cDNA fragment was cloned in the baculovirus transfer vector pBluebac, under the control of the baculovirus polyhedron promoter. All recombinant DNA manipulations were performed in the conditions recommended by the enzyme manufacturers' instruction. The pBluebac vector contains the E.coli β-galactosidase gene under the control of a different baculovirus promoter, and viruses that have undergone recombination and taken up the DNA vector can convert the chromophore X-gal to a blue product.

Creation of recombinant baculovirus was done using the MaxBac expression system (Invitrogen) following exactly the protocols recommended by the manufacturer. Briefly, plasmid and wild type virus DNA were mixed and used to transfect Sf-9 cells by the calcium phosphate method. Virus was produced by the transfected cells and shed into the culture medium. Recombinant virus was identified in plaque assays by the blue color produced by the action of β-galactosidase on X-gal included in the plaque media at a concentration of 150 μg/ml, and purified from wild type virus by repetitive dilution/plaque formation. Purified virus was expanded to 500 ml by infection of fresh Sf-9 cells. Several clones were analyzed for the ability to cause secretion of α2,3-N sialyltransferase into the infected cell medium by testing an aliquot of the media directly in the radioactive sialyltransferase assay described below.

To grow large amounts of virus, 3×10⁶ Sf-9 cells in a 25 cm² tissue culture flask in 5 ml GCMS+10% FCS were infected with a single blue plaque free of wild type virus and allowed to grow for 5–7 days at 27° C. The resulting 5 ml of virus stock were clarified by centrifugation and further expanded. Sf-9 cells in the logarithmic growth phase (0.5–1.5×10⁶ cells/ml) were infected at a concentration of 1×10⁷ cells per ml at a multiplicity of infection (moi) of 1, assuming a virus titre in the 5 ml stock of 1×10⁸ plaque forming units (pfu) per milliliter. Cells were diluted back ten-fold in GCMS+10% FCS and allowed to growth for 5–7 days at 27° C. The resulting virus was clarified and the virus titre was determined by plaque assay, and generally was greater than 10⁹ pfu/ml. To express α2,3-N sialyltransferase, 2.5×10⁹ Sf-9 cells in the logarithmic growth phase were plated on each layer of a Ten Tray Cell Factor (Nunc, Naperville, Ill.), designated CF-10. Each CF-10 has a total growing area of 6000 cm², and the cells were infected with recombinant baculovirus at moi=5 in a volume of 300 ml. After incubation for one hour, 1 liter of Excell-400 (JRH Biosciences), a serum-free medium, was added, and cells were incubated at 27° C. for 72 hours. The medium was harvested, clarified, and filtered through a 0.2 μm filter unit. Fresh media (Excell 400 supplemented with 2% fetal calf serum) was added and the cells were incubated at 27° C. for an additional 48 hours, whereupon medium was harvested, clarified and filtered.

α2,3-N sialyltranferase activity was assayed using a modification of the published assay (Sadler et al., 1979). In a 30 μl volume, 14 μl of sample was mixed with 3.5 μl lacto-N-tetrose (Galβ1,3GlcNAcβ1, 3Galβ1,4Glc) and 12.5 μl of an assay mix as described below. The samples were mixed briefly, spun to the bottom of the reaction tube, and incubated at 37° C. for 10 minutes. The reactions were then immediately diluted in one ml of 5 mM phosphate buffer, pH 6, and applied to a 0.5 ml ion exchange column. The column run-through and a one ml wash were collected in scintillation tubes and counted. A unit is defined as the amount of enzyme required to transfer one micromole of sialic acid to acceptor per minute.

The sample consisted of either neat supernatant or supernatant diluted such that the kinetics of the reaction were kept in the linear range, approximately 10000 cpm output from the column. The assay mix was prepared by drying 0.65 ml (50 μCi) of [¹⁴C]-CMP-sialic acid (NEN, Boston, Mass.) and resuspending in 0.65 ml water containing 2.3 mg of CMP-sialic acid. To this were added 0.96 of a 1 M solution of sodium cacodylate buffer, pH 6; 0.48 ml of 20% Triton CF-54; 0.29 ml of a 50 mg per ml solution of bovine serum albumin (all obtained from Sigma, St. Louis, Mo.); and water to a total volume of 8 ml. The specific activity of the assay mix was determined, and it was aliquoted and stored at −20° C. The ion exchange resin used is AG1-X8, 200–400 mesh, phosphate form (Biorad, Richmond, Calif.).

Concentration and purification of α2,3-N sialyltransferase. Media (1–3 liters) containing α2,3 NST was filtered and concentrated to approximately 250 ml in an Amicon CH2PRS spiral cartridge system equipped with an S1Y10 cartridge. The unit was then run in diafiltration mode to desalt the concentrated supernatant with three volumes of 10 mM cacodylic acid, 25 mM NaCl, 25% glycerol, pH 5.3 (buffer A). Samples are then applied to a column (2.5×17 cm) of S-Sepharose Fast Flow (Pharmacia) equilibrated with buffer A at a flow rate of 2 ml/min. After all of the sample has been loaded, the column was washed with buffer A until the $OD_{280}$ of the column effluent had returned to baseline (1.6 column volumes). α2,3 NST was then eluted from the column with 50 mM cacodylic acid, 1M NaCl, 25% glycerol pH 6.5. Fractions containing α2,3 NST were pooled and dialyzed overnight against 1L 50 mM cacodylic acid, 0.5M NaCl, 50% glycerol, pH 6.0, and then stored at −80° C.

EXAMPLE 8

Tissue Distribution of the Rat α2,3-N Sialyltransferase

In order to characterize tissue distribution of the cloned rat α2,3-N sialyltransferase, total RNA was isolated from various rat tissues and probed with ³²P-labeled cDNA of the sialyltransferase. Hybridization to an mRNA of ~2.5 Kb was observed in all tissues tested. As observed for the two cloned sialyltransferases, the α2,3-N sialyltransfease exhibited differential expression in tissues of the rat. The highest level of the α2,3-N sialyltransferase mRNA was detected in the brain. Liver, kidney, colon, heart, ovary and lung express intermediate levels of the message while low levels of mRNA was found in submaxillary gland, spleen, and intestine. In contrast, the highest level of the Galβ1,4GlcNAc α2,6-Sialyltransferase mRNA (4.7 and 4.3 Kb, 41, 46) was detected in rat liver and submaxillary gland while low levels of the mRNA was found in heart, ovary, and brain.

EXAMPLE 9

Conserved Region of Homology in Catalytic Domain

The conserved region of the sialyltransferases family—Comparison of the primary structures of the three cloned sialyltransferases revealed a region of extensive homology (FIG. 12). This region consists of 55 amino acids from residue 156 to residue 210 of the α2,3-N sialyltransferase with 42% of the amino acids identical and 58% of the amino acids conserved between all three enzymes. The sequences of all three sialyltransferases have no significant homology outside this region. Since this region of homology is located near the center of the catalytic domain of the enzymes, this region may represent a conserved structure necessary for the enzymatic activity of these sialyltransferases.

Three members of the sialyltransferase family of glycosyltransferases have been cloned. Although 85% of the sequences of all three cloned sialyltransferase have no significant homology, a region of 55 amino acids in the center of each molecule is highly conserved suggesting a protein motif in the sialyltransferase family. A protein motif is a well-conserved group of amino acids in a specific region. Other amino acid residues outside of this region are usually poorly conserved, so there is low overall homology in proteins containing the same motif. By this definition, the conserved region defined by the primary structures of three cloned sialyltransferases is a motif in the sialyltransferase family.

Protein motifs are often involved in catalysis and ligand-binding (Hodgman, T. C., Comput. Applic. Biosci. 5, 1–13 [1989]; Bairoch, A, Prosite: A Dictionary of Protein Sites and Patterns, 5th edn., University of Geneva [1990]; and Sternberg, M. J. E., Nature 349, 111 [1991]). All three cloned sialyltransferases catalyze the transfer of sialic acid from CMP-NeuAc in α2,3 or α2,6 linkage of terminal galactose to form the following sequences:

NeuAcα2,3 Galβ1,3(4)GlcNAc-(ST3N)
NeuAcα2,3 Galβ1,3GlcNAc-(ST3O)
NeuAcα2,3 Galβ1,4GlcNAc-(ST6N)

All three enzymes share a common function. More than 50% of the residues in the conserved region are either charged or polar amino acids consistent with the being at the surface of the enzymes. Six of the charged residues in this region are identical in all three sialyltransferases. It is very striking that there are seven amino acid residues in one stretch in the conserved region identical between all three cloned sialyltransferases-Asp.Val.Gly.Ser.Lys.Thr.Thr (SEQ. ID. NO:21) (FIG. 12).

EXAMPLE 10

Cloning of a New Sialyltransferase Using the Conserved Region of Homology

The conserved region of homology was used to clone another member of the sialyltransferase gene family.
PCR cloning with degenerate oligonucleotides—Two degenerate oligonucleotides corresponding to the 5' and 3' ends of the conserved region of homology (FIG. 13) were synthesized (Genosys). The sequence of the 5' and (SEQ. ID. NO:23) 3' primers were 5'GGAAGCTTTGSCRNMGST-GYRYCRTCGT and 5'CCGGATCCGGTR GTYTTNSN-SCCACRTC (SEQ. ID. NO:24) (N=A+G+T+C, S=G+C, R=A+G, M=A+C, Y=C+T), respectively. PCR experiments were performed using 100 pmol of each primer and first strand cDNA synthesized from newborn rat brain as a template. Amplification was carried out by 30 cycles of 94° C. for 1 minute, 37° C. for 1 minute, and 72° C. for 2 minutes. The PCR products were digested with Bam HI and Hind III and subcloned into these sites of Bluescript KS (Stratagene, 11099 North Torrey Pines Road, La Jolla, Calif. 92037). Subclones were characterized by sequencing with a T3 primer. The amplified fragment from one of these subclones, SM1, was used below to screen for an SM1-containing gene which encodes sialyltransferase.
Cloning of the SM1 containing gene—Random primed newborn rat brain cDNA was ligated with EcoRI-NotI linkers then subsequently ligated into EcoRI digested λgt10. The resultant library was packaged using a Stratagene Gigapack II packaging extract and plated on $E.$ $coli$ C600 hfl. Approximately $10^6$ plaques were screened with the cloned SM1 PCR fragment. Four clones, STX1-4, were purified and subcloned into the NotI site of Bluescript (Stratagene) for further analysis.
Northern Analysis—Total RNA from rat tissues was prepared using an acid phenol procedure as described previously (Chomoznsyi, P., et al., $Anal.$ $Biochem.$ 162, 136–159 [1987]. Newborn RNA samples were isolated from rat pups within four days of birth. RNA was electrophoresed in a 1% agarose gel containing formaldehyde, transferred to nitrocellulose and hybridized following standard procedures (Kriegler, M. Gene transfer and expression, Stockton Press, N.Y., N.Y. [1990]). Northern blots were probed with a gel purified, radiolabeled, 900 bp EcoRI fragment isolated from STX1.
Construction of a soluble form of STX—A truncated form of STX, lacking the first 31 amino acids of the pen reading frame, was prepared by PCR amplification with a 5' primer containing an in-frame Ban HI site and a 3' primer located 50 bp downstream of the stp codon. Amplification was carried out by 30 cycles of 94° C. for 1 minute, 45° C. for 1 minute and 72° C. for 2 minutes. The fusion vector pGIR201 protA was constructed by inserting a BclI/Bam HI fragment, isolated from pRIT5 (Pharmacia LKB Biotech, Inc., 1025 Atlantic Avenue, Suite 101, Alameda, Calif. 94501), encoding the protein A IgG binding domain into the Bam HI site of pGIR201 (a gift from Dr. K. Drickamer, Columbia University). The amplified fragment was subcloned into the Bam HI site of pGIR201protA resulting in fusion of STX to the insulin signal sequence and the protein A present in the vector. An Nhe fragment containing the fusion protein was subcloned into plasmid pSVL resulting in the expression plasmid AX78.
Expression of the soluble form of STX—The expression plasmid AX78 (10 ug) was transfected into COS-1 cells in 10 cm plates. Two days after transfection the culture media was collected and incubated with IgG sepharose (Pharmacia) for 1 hour at room temperature. The beads were assayed for sialyltransferase activity using oligosaccharides, antifreeze glycoprotein, mixed gangliosides and neuraminidase-treated newborn rat brain membranes as acceptor substrates. Transfer of sialic acid to these acceptors was measured using ion-exchange (Weinstein, J., et al., $J.$ $Biol.$ $Chem.$ 257 13835–13844 [1982]), size exclusion (Id.), and descending paper chromatography (McCoy, R. D., et al., $J.$ $Biol$ $Chem.$ 260 12695–12699 [1985]).
Identical transfections were performed for pulse-chase labeling experiments. Following a 36 hour expression period the plates were incubated at 37° C. with 2.5 ml DMEM-methione. After 1 hour 250 uCI$^{35}$S-translabel (Amersham, 2636 S. Clairebrook, Arlington Heights, Ill. 60005) was added to the media and the plates were incubated for an additional 3 hours. At the end of this time the plates were washed and incubated overnight with complete DMEM. Labeled fusion protein was isolated by incubation with IgG sepharose (Pharmacia). Following binding the beads were washed, boiled in Laemalli sample buffer and the released proteins were analyzed by SDS-PAGE/fluorography.
PCR amplification of a conserved region of homology related to those found in characterized sialyltransferases. While approximately 70% of the amino acids present in the conserved region of homology of the characterized sialyltransferases are conserved, the largest continuous regions of conservation are found in the amino acid sequences at the ends of the conserved region of homology (FIG. 13). The amino acid sequence near the C-terminal end of the conserved region of homology had been found to contain a continuous stretch of seven invariant residues. The strong conservation of this amino acid sequence allowed for the design of a relatively low complexity oligonucleotide with a 256 fold degeneracy which encompassed all the observed variation in codon usage. The design of an oligonucleotide corresponding to the N-terminal end of the conserved region of homology was more difficult. The amino acids present in this region exhibit more variability than those found at the opposite end of the conserved region of homology. Oligonucleotide design was further complicated by the high codon redundancy of the amino acids. In order to compensate for these factors the oligonucleotide from the 5' end of the conserved region of homology was synthesized with a 1026 fold degeneracy. While this degree of complexity is near the threshold of degeneracy allowable in PCRE experiments, the resultant primer accounted for all of the nucleotide sequences found to encode for this region of the conserved region of homology.
Neural development is a complex process during which glycosyltransferases are subject to dynamic regulation as is evident from the dramatic changes found in cell surface carbohydrate expression. For this reason newborn rat brain was selected as a source for efforts to isolate new sialyltransferases. Using newborn rat brain cDNA as a template PCR experiments with the degenerate primers resulted in the amplification of a 150 bp band, consistent with the known size of the conserved region of homology. Subcloning and sequencing revealed that the band was a mixture of two DNA fragments. Of thirty isolates characterized 56% encoded the α conserved region of homology; the remaining clones encoded a unique conserved region of homology, SM1. Somewhat surprisingly SM1 contains five changes in amino acids that were found to be invariant in the three previously cloned sialyltransferases. While these changes decrease the total number of invariant residues, the new sequence information provided by the characterization of SM1 raises the overall conservation of the consensus sequence.

The predicted amino acid sequence of SM1 does not exhibit a bias toward any individual conserved region of homology. At some positions (amino acids 1, 2, 53, 54) SM1 is similar to the α2,6 conserved region of homology; in other positions (amino acids 8, 9, 54, 55) SM1 reflects the sequences found in the α2,3 conserved region of homology. While the conserved region of homology is 85% conserved, this balance of similarities results in SM1 being approximately 45% homologous to the other members of the sialyltransferase gene family.

Primary Structure of the SM1 containing gene—Sequence analysis of the 1.5 kb clone STX1 identified a continuous 375 amino acid open reading frame that encoded the SM1 conserved region of homology characterized in earlier PCR experiments (FIG. 14). The deduced amino acid sequence of STX1 suggests that this protein is a type II transmembrane protein as has been observed for each of the other cloned glycosyl-transferases. The predicted amino acid sequence of STX1 indicates the presence of a hydrophobic region eight residues from the amino terminus of the protein which could serve as a signal anchor domain. The conserved region of homology is located near the center of the protein. The overall size of the STX protein and the relative positions of both the hydrophobic region and the conserved region of homology strongly resemble the primary sequence characteristics of cloned sialyltransferases. Although STX exhibits no homology to the other cloned sialyltransferases other than to the conserved region of homology, the pronounced structural similarities of these genes make it clear that STX is a member of the sialyltransferase family.

Enzymatic characterization of STX—Naturally occurring soluble forms of sialyltransferases can be found in various secretions and body fluids (Paulson, J. C., et al., *J. Biol. Chem.* 252 2356–2367 [1977] and Hudgin, R. L., et al., *Can. J. Biochem.* 49 829–837 [1971]). These soluble forms result from proteolytic digestion cleaving the stem region of the sialyltransferase releasing the catalytic domain from the transmembrane anchor. Soluble sialyltransferases can be recombinantly constructed by replacing the endogenous signal-anchor domain with a cleavable signal sequence (Colley, K. J., et al., *J. Biol. Chem.*, 264 17619–17622 [1989]). In order to facilitate functional analysis of STX a soluble form of the protein was generated by replacing the first 31 amino acids with the cleavable insulin signal sequence and the protein A IgG binding domain. The IgG binding domain was included in the construction to aid in the detection of the soluble STX protein. Similar fusions with the ST3N are actively secreted from expressing cells, bound by IgG sepharose and are enzymatically active. When an expression plasmid containing the protein A/STX fusion (AX78) was expressed in COS-1 cells a 85 kd protein was isolated. The size of the fusion protein is approximately 15 kd greater than the predicted molecular weight of the polypeptide suggesting that a number of the STX potential N-linked glycosylation sites are being utilized.

The bound fusion protein was assayed for sialyltransferase activity using a variety of acceptor substrates. Activity was not detected using β-galactoside acceptors containing Galβ1,3(4)GlcNAc sequences; similarly no transfer of sialic acid to the O-linked oligosaccharides of antifreeze glycoprotein was detected. The expression of STX in brain tissue suggests that the gene might be involved in glycolipid biosynthesis; however, mixed gangliosides isolated from adult bovine brain failed to serve as an acceptor substrate. Neuroamidase-treated newborn brain membranes were the only substrate to exhibit even a marginal ability to serve as an acceptor. Incubation of treated membranes with the STX fusion protein resulted in a 50% increase in activity over background.

Developmental and tissue specific expression of STX—In order to determine the pattern of expression and message size of the STX gene, Northern blots were probed with a 900 bp EcoRI fragment isolated from STX1. Of the various tissues examined hybridization of a 5.5 kb message was only observed in newborn rat brain RNA. No cross-hybridization to related conserved region of homology was observed. The restricted expression of STX is a departure from the differential tissue specific expression found with characterized sialyltransferases. While each of these genes is independently regulated resulting in different patterns of issue specific expression, in general each sialyltransferase is variably expressed in a number of diverse tissues (Paulson, J. C., et al., *J. Biol. Chem.* 264 10931–10934 [1989]). In contrast STX is only expressed in newborn brain; the expression does not appear to be a generalized embryonic phenomena as the message was not detected in newborn kidney.

EXAMPLE 11

Cloning and Express of Human Galβ1,3(4) GleNAc α2,3-Sialyltransferase

PCR cloning with degenerate oligonucleotides: Based on the homology in the sequences demonstrated in the preceding examples, two degenerate oligonucleotides were synthesized (Genosys), which were predicted to yield a 150 bp amplified fragment. The sequence of the 5' and 3' primers were 5'-GGAAGCTTTGSCRNMGSTGYRYCRTCGT (SEQ. ID. NO:25) and 5'-CCGGATCCGGTRG TYTTNSNSCCSACRTC (SEQ. ID. NO:26) (N=A+G+T+C, S=G+C, R=A+G, M=A+C, Y=C+T), respectively. For PCR amplification, first strand cDNA synthesized from human placenta total RNA (Clontech) was combined with 100 pmol of each primer. Thirty cycles (95° C. for 1 minute, 37° C. for 1 minute and 73° C. for 2 minutes) were run using pfu polymerase (Stratagene) and the products were digested with BamHI and HindIII and subcloned into these sites of Bluescript SK (Stragene). Clones were sequenced using a T7 primer.

Isolation of human ST3N cDNA—Random primed human placenta cDNA was ligated with EcoRI linkers then subsequently ligated into EcoRI digested λZAPII(Stratagene). The resultant library was packaged using a Stratagene GigapackII packaging extract and plated on *E. coli* XL-1 Blue (Stratagene). Approximately 1 million plaques were screened with the cloned PCR fragment described above. Two positive clones were plaque-purified and then excised into Bluescript vectors by in vivo excision with R408 helper phage.

Construction of soluble forms of human ST3N—A truncated form of human ST3N, which lacked the first 61 amino acids of the open reading frame was amplified by PCR using a 5' primer containing an in-frame BamHI site and a 3' primer located 50 bp downstream of the stop codon. PCR reactions were carried out with Pfu polymerase by 30 cycles of 95° C. for 45 seconds, 55° C. for 45 seconds and 73° C. for 90 seconds. The fusion vector pGIR201protA was constructed by inserting a BclI/BamHI fragment, isolated from pRIT5 (Pharmacia), encoding the protein A IgG binding domain into the BamHI site of pGIR201 (a gift from Dr. K. Drickamer). Then each PCR fragment was subcloned into BamHI site of pGIR201protA resulting in fusion of human ST3N to the insulin signal sequence and the protein A present in the vector. Then each resulting fusion protein was inserted into the expression vector pSVL to yield the expression plasmid A3NHP.

Expression of the soluble form of the sialyltransferase and assaying enzyme activity—The expression plasmid (10 μg) was transfected into COS-1 cells on 100 mm plates using Lipofectin (BRL). After 48 h, the cell culture media was collected and incubated with IgG Sepharose (Pharmacia) for 1 h. The beads were assayed for sialyltransferase activity using oligosaccharides and glycoprotein as acceptor substrates. Transfer of sialic acid to the substrate was monitored using ion-exchange or Sephadex G-50 chromatography.

Northern analysis: Multiple tissue northern blots of poly (A)+ RNAs were purchased from Clontech Laboratories for the analysis. The cDNA inserts of clones ST3NHP1 were gel-purified, radiolabeled (>1×10$^9$ cpm/mg), and used as probes.

Figure 15:
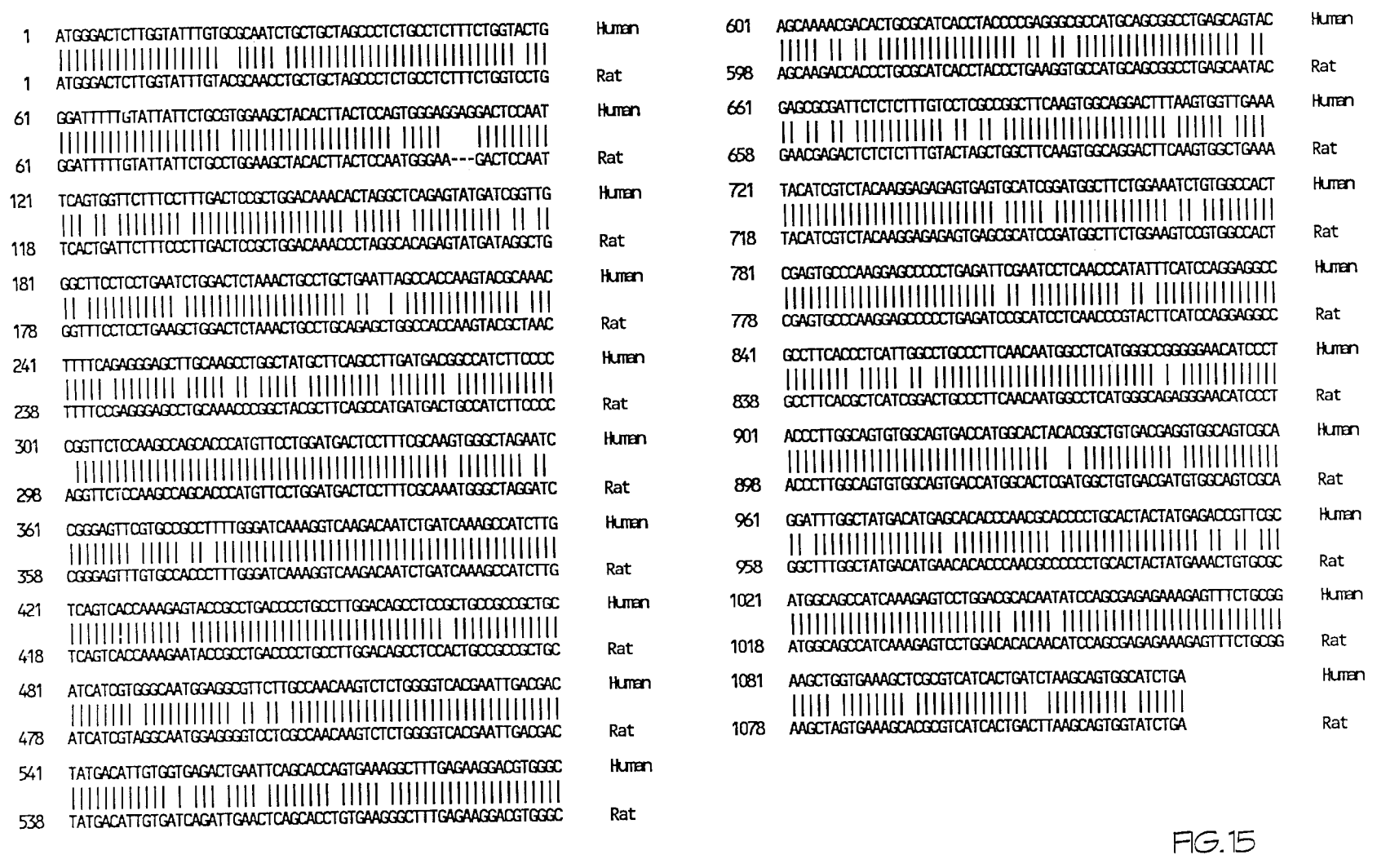

Results—Using human placenta cDNA as a template, PCR experiments with degenerate primers to the conserved region resulted in the amplification of 150 bp band which was subcloned for analysis of individual clones. Of fifty clones sequenced three proved to be the human homolog of the rat ST3N (See Examples 4–6). In order to obtain the entire coding sequence, the human ST3N 150 bp fragment was used to screen a human placenta cDNA library. Two positively hybridizing clones were isolated. Characterization of the positive clones revealed that clone ST3NHP-1 contained a 1.3 Kb insert, whereas clone ST3NHP-2 was 1.1 Kb in length. Sequence analysis revealed that clone ST3NHP-1 contained the complete open reading frame of the sialyltransferase. It consists of a 155-base pair 5'-untranslated region, an open reading frame 1125 base pairs in length, and a 13-base pair 3'-untranslated region. FIG. 15 shows the nucleotide sequence comparison between the open reading frame of ST3NHP-1 cDNA (SEQ. ID. NO:9)with the corresponding portion of the rat ST3N (SEQ. ID. NO:3) (FIG. 2). There is 91% homology at the nucleotide sequence level, and 97% conservation between ST3NHP-1 (SEQ. ID. NO:10) and the rat ST3N (SEQ. ID. NO:4) is observed at the amino acid sequence level (FIG. 16). The differences include a single amino acid insert (Glu) in the stem region of the human protein. This insertion parallels a similar finding for the human α2,6-sialyltransferase which encoded three additional residues E-K-K in the stem region compared to the rat one.

When the expression plasmid, A3NHP (human) was expressed in COS-1 cells, an approximately 80 Kd protein was secreted from each transformant which exhibited sialyltransferase activity. In order to characterize the substrate specificity of these fusion proteins, they were purified on IgG Sepharose and assayed for sialyltransferase activity against a panel of acceptor substrates. As shown in Table 3, there is no significant difference between the human and rat fusion proteins. These results indicate that human ST3N enzyme is quite similar to rat enzyme (Examples 4–6) which has been found to preferentially act on type 1 chain (Galβ1, 3GlcNAc), but which can also catalyze the sialylation of type 2 chain (Galβ1,4GlcNAc), albeit with lower catalytic efficiency.

TABLE 3

Comparison of acceptor specificity of the human and rat ST3N.

| | Relative activity (%) | |
|---|---|---|
| Acceptor (0.2 mM)* | Human | Rat |
| Galβ1, 3GlcNAcβ1, 3Galβ1, 4Glc (LNT) | 100 | 100 |
| Galβ1, 3GlcNAc | 48 | 49 |
| Galβ1, 4GlcNAcβ1, 3Galβ1, 4Glc (LNnT) | 5 | 4 |
| Galβ1, 4GlcNAc | 22 | 19 |
| Galβ1, 4Glc | 9 | 7 |
| Asialo-α$_1$-acid glycoprotein | 14 | 9 |

*The activities are relative to that obtained with LNT, respectively. The rat ST3N kinetic constants for both type 1 and type 2 chains (14) differ primarily in these Km values (0.1–0.6 and 2–4 mM, respectively, and have similar relative Vmax (1.0–1.2 and 0.8–1.0, respectively. For asialo-α$_1$ acid glycoprotein the concentration was set at 0.2 mM relative to the galactose content.

EXAMPLE 12

Cloning and Expression of ST3 Sialyltransferase

PCR cloning with degenerate oligonucleotides—Based on the homology in the sequences demonstrated in the preceding examples, two degenerate oligonucleotides were synthesized in the same manner as described previously. For PCR amplification, first strand cDNA synthesized from human placenta total RNA (Clontech) was combined with 100 pmol of each primer. Thirty cycles (95° C. for 1 minute, 37° C. for 1 minute, and 73° C. for 2 minutes) were run using Pfu polymerase (Stratagene) and the products were digested with BamHI and HindIII, and subcloned into these sites of Bluescript SK (Stratagene). The clones were sequenced using a T7 primer (Stratagene).

Cloning of a human sialyltransferase—Random primed human placenta cDNA was ligated with EcoRI linkers then subsequently ligated into EcoRi digested λZAPII (Stratagene). The resultant library was packaged using a Stratagene Gigapack II packaging extract and plated on Escherichia coli XL-1 Blue (Stratagene). Approximately 1 million plaques were screened with the cloned PCR fragment described above. Six positive clones were plaque-purified and then excised into Bluescript vectors by in vivo excision with R408 helper phage. Northern analysis—Multiple tissue northern blots of poly (A)+ RNAs were purchased from Clontech Laboratories for the analysis. The blots were probed with a gel-purified, radiolabeled (>1×10$^9$ cpm/μg), 1.3 Kb EcoRI fragment isolated from ST3-2.

Construction of soluble form of the sialyltransferase—A truncated form of ST3, lacking the first 39 amino acids of the long-form open reading frame, was amplified by PCR using 5' primer containing an in-frame BamHI site and 3' primer located 50 bp downstream of the stop codon. PCR reaction was carried out with Pfu polymerase by 30 cycles of 95° C. for 45 seconds, 58° C. for 45 seconds, and 73° C. for 90 seconds. The fusion vector pGIR201protA was constructed as described before (13,16). The PCR fragment was subcloned into BamHI site of pGIR201protA resulting in fusion of ST3 to insulin signal sequence and the protein A present in the vector. The resulting fusion protein was inserted into the expression vector pSVL to yield the expression plasmid AZ3.

Expression of the soluble form of the sialyltransferase (ST3) and assaying enzyme activity—The expression plasmid (10 μg) was transfected into COS-1 cells on 100 mm plates using Lipofectin (BRL) as suggested by the manufacturer. After 48 h, the cell culture media was collected and concentrated by ultrafiltration using a Centricon 10 (Amicon). The concentrated media was assayed for sialyltransferase activity using oligosaccharides, glycoproteins and glycolipids as acceptor substrates. Transfer of sialic acid to the substrate was monitored using ion-exchange or Sephadex G-50 chromatography.

Pulse-chase labeling of transfected COS-1 cells—Identical transfections were performed for this purpose. Following a 48 hour expression period the plates were washed with Met-free DMEM media containing 5% fetal calf serum (GIBCO) and cultured in the same media for 1 hr. The cells were pulse-labeled with 250 $\mu$Ci [$^{35}$S]-Met Express label (Du Pont-New England Nuclear) in 2.5 ml of Met-free media for 3 hrs. These cells were then washed with PBS and chased overnight with complete DMEM media containing 5% fetal calf serum. The media, containing secreted proteins, were then harvested, incubated with IgG Sepharose (Pharmacia). Following binding the beads were washed, boiled in Laemalli sample buffer and the released proteins were subjected to SDS-PAGE and analyzed by fluorography.

Linkage specificity analysis of the sialyltransferase—Asialo $\alpha_1$-acid glycoprotein was sialylated with CMP [$^{14}$C] NeuAc (Du Pont-New England Nuclear) using concentrated media containing ST3 enzyme which was expressed in COS-1 cells, ST3N, or ST6N enzymes, respectively. The $^{14}$C-labeled products were isolated by gel filtration on a column of Sephadex G-50, and then concentrated and washed with $H_2O$ to remove salts using Centricon 10 (Amicon). The sialylated glycoprotein was subjected to digestion with sialidase from Newcastle disease virus (Oxford Glycosystems) which enzyme was highly specific for non-reducing terminal sialic acid $\alpha$2,3 linked to galactose or N-acetylgalactosamine, or $\alpha$2,8 linked to sialic acid. The treated products were applied to a column of Sephadex G-50 and the release of [$^{14}$C] NeuAc was monitored by liquid scintillation counting of the eluate.

Figure 17:
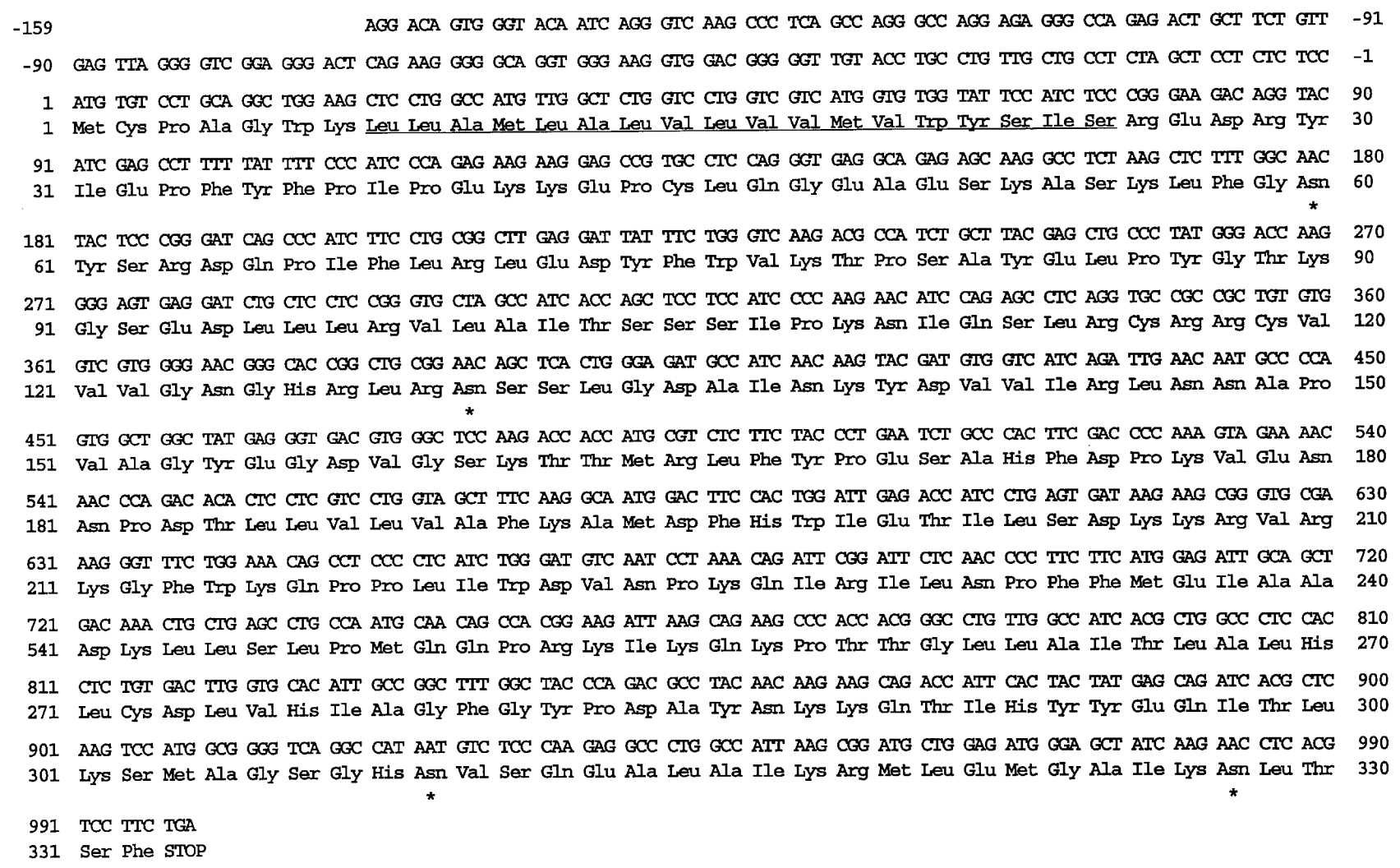

Primary structures of two forms of the ST3—In order to isolate the complete coding sequence of the gene containing ST3 sialyltransferase, the SM3 150 bp fragment was used to screen a human placenta cDNA library. Six positively hybridizing clones (ST3-1~6) were isolated. Characterization of the positive clones revealed that clone ST3-1 contained a 1.8 kb insert, clones ST3-2,3, and 4 were 1.3 kbs, clone ST3-5 was 1.2 kb, and clone ST3-6 was 1.1 kb in length. Sequence analysis of them revealed that the cDNAs occurred in two forms, long- and short-forms, and clone ST3-1 and ST3-2 contained the complete open reading frames of them, respectively. The amino-terminal sequence of long-form, ST3-1, contains three in-frame ATG codons in close proximity. If the first ATG codon is the initiation point for translation of it although the ATG codon is a poor sequence context for translation initiation with pyrimidine at position—3 relative to the ATG, it consists of a 159-base pair 5'-untranslated region, an open reading frame 996 base pairs in length, and 3'-untranslated region of approximately 0.6 kb. The open reading frame of the clone codes a 332 amino acids with four potential N-linked glycosylation sites (FIG. 17). A Kyte-Doolittle hydropathy analysis revealed one potential membrane-spanning region consisting of 18 hydrophobic residues, located 7 residues from the amino terminus. This structural feature indicates that this gene, like the other glycosyltransferases which have been studied, has a type II membrane topology and that this single hydrophobic region could serve as a noncleavable amino-terminal signal-anchor domain.

Homology to other exemplary cloned sialyltransferases—Comparison of the primary structure of ST3 and the three cloned sialyltransferases of the previous examples reveals a limited but distinct homology (FIG. 18). The amino acid sequence of ST3 has 38% identity with that of ST3N (SEQ. ID. NO:12) in the catalytic domain. While the region of the extensive homology is located around the center of the presumed catalytic domain, there are several conservative replacements at other positions throughout the catalytic domain although alignment of the regions requires the introduction of several gaps into the sequences.

Expression of a soluble form of the ST3 and enzymatic characterization of it—In order to facilitate functional analysis of ST3, it was desirable to produce a soluble form of the enzyme which when expressed would be secreted from the cell. A soluble form of the protein was generated by replacing the first 39 amino acids with cleavable insulin signal sequence and the protein A IgG binding domain. When the expression plasmid containing the protein A/ST3 fusion (AZ3) was expressed in COS-1 cells, approximately 80 kd protein was secreted. The size of the fusion protein was approximately 15 kd greater than the predicted molecular weight of the polypeptide suggesting that a number of the ST3 potential N-linked glycosylation sites are being utilized.

To characterize the substrate specificity of the fusion proteins, we assayed the media from cells transfected with AZ3 using a variety of acceptor substrates as shown in Table 4. To compare it to that of the other two cloned $\alpha$2,3-sialyltransferases, ST3N and ST3O, we did the same experiments using each expression plasmid as described in the previous examples.

Homology to other sialyltransferases—Comparison of the primary structure ST3 protein (SEQ. ID. NO.12) and the three other cloned sialyltransferases indicates that it is the shortest of the four enzymes which range from 332 to 403 amino acids in length. Previous comparisons of the sequences of the other three sialyltransferases have found limited regions of high conservation resulting in the definition of a common sialylmotif (Wen, D. X., Livingston, B. D., Medzihradzky, K. F., Kelm, S., Burlingame, A. L., and Paulson, J. C. (1992) *J. Biol. Chem.* 267, 21011–21019; Drickamer, K. (1993) *Glycobiology* 3, 2–3; Livingston, B. D., and Paulson, J. C. (1993) *J. Biol. Chem.* 268, 11504–11507). Following the lead of Drickamer and optimizing alignment of the sequences by allowing the introduction of 12 gaps, we observed extensive sequence homology was revealed that was not recognized earlier. Indeed, the aligned proteins exhibited identity in three or more sequences at 72 positions, and two or more sequences at greater than 180 positions. The highest homology of ST3 to the other three sequences was with that of ST3N (SEQ. ID. NO:4), with 35% identity throughout the aligned sequences.

These observations suggest that these genes are more conserved in overall structure than was previously realized.

TABLE 4

Comparison of acceptor specificity of ST3, ST3O, and ST3N.

| | Relative rate (%) | | | | | |
|---|---|---|---|---|---|---|
| | 0.2 mM | | | 2.0 mM | | |
| Acceptor | ST3 | ST3O | ST3N | ST3 | ST3O | ST3N |
| Gal$\beta$1,3GalNAc | 100 | 100 | 3 | 100 | 100 | 10 |
| Gal$\beta$1,3GlcNAc | 0 | 2 | 49 | — | — | — |
| Gal$\beta$1,4GlcNAc | 4 | 0 | 19 | 23 | 0.9 | 46 |
| Gal$\beta$1,4Glc | 3 | 0 | 7 | 11 | 0.9 | 20 |
| Gal$\beta$1,3GlcNAc$\beta$1,3Gal$\beta$1,4Glc (LNT) | 0 | 0.5 | 100 | 2.3 | 3 | 100 |

TABLE 4-continued

Comparison of acceptor specificity of ST3, ST3O, and ST3N.

| | Relative rate (%) | | | | | |
|---|---|---|---|---|---|---|
| | 0.2 mM | | | 2.0 mM | | |
| Acceptor | ST3 | ST3O | ST3N | ST3 | ST3O | ST3N |
| Galβ1,4GlcNAcβ1,3Galβ1,4Glc (LNnT) | 24 | 0 | 4 | 49 | 0.5 | 18 |
| Galβ1,3(Fucα1,4)GlcNAcβ1,3Galβ1,4Glc (Le*) | 0 | 0 | 0 | 0 | 0 | 0 |
| Galβ1,4(Fucα1,3)GlcNAcβ1,3Galβ1,4Glc (Le*) | 0.1 | 0 | 0 | 1 | 0 | 0 |
| Antifreeze glycoprotein (Galβ1,3GalNAc-Thr)* | 50 | 57 | 2 | — | — | — |
| Asialofetuin (Galβ1,3GalNAc-Thr/Ser and Galβ1,4GlcNAc-R)* | 92 | 26 | 18 | — | — | — |
| Asiao-α₁ acid glycoprotein (Galβ1,4GlcNAc-R)* | 51 | 0 | 9 | — | — | — |
| Ovine submacillary asialo-mucin (GalNAc-Thr/Ser)* | 3.8 | 5 | 0.5 | — | — | — |
| Galβ1,3GalNAcβ1,4Galβ1,4Glcβ1-Cer (Asialo-$G_{M1}$) | 64 | 88 | 8 | — | — | — |
| Galβ1,3GalNAcβ1,4(NeuAcα2-3)Galβ1,4Glcβ1-Cer($G_{M1}$) | 27 | 47 | 0 | — | — | — |
| GalNAcβ1,4Galβ1,4Glcβ1-Cer (Asialo-$G_{M2}$) | 2 | 0.5 | 0 | — | — | — |
| GalNAcβ1,4(NeuAcα2-3)Galβ1,4Glcβ1-Cer ($G_{M2}$) | 1 | 0.3 | 0 | — | — | — |
| Galβ1,4Glcβ1-Cer (LacCer) | 4 | 0.1 | 0 | — | — | — |
| NeuAcα2,3Galβ1,4Glcβ1-Cer ($G_{M3}$) | 0 | 0.1 | 0 | — | — | — |
| Galβ1,4GlcNAcβ1,3Galβ1,4Glcβ1-Cer (n$L_{c4}$) | 11 | 0.1 | 0.6 | — | — | — |

*The concentration was set at 0.2 mM relative to the galactose (or N-acetylgalactosamine) content of each glycoprotein.

As shown in Table 4, sialic acid was incorporated into antifreeze glycoprotein, asialo-fetuin and asialo-α₁-acid glycoprotein by ST3 enzyme (SEQ. ID. NO:12) whereas ovine submaxillary asialo-mucin was not an acceptor. In addition, there was not any significant amount of sialic acid incorporated in any other glycoproteins examined including intact fetuin and α₁-acid glycoprotein (data not shown). Of which asialo-fetuin is best acceptor, which contains both Galβ1,3GalNAc and Galβ1,4GlcNAc sequences. Even the small amount of sialic acid incorporated into the asialo-mucin can be accounted for by microheterogeneity of tis oligosaccharide chains including small amounts of Galβ1,3GalNAc structures. In contrast, the ST30 enzyme is quite specific for the Galβ1,3GalNAc sequence of glycoproteins and the ST3N (SEQ. ID. NO:4) one acts on acceptors with Galβ1,4GlcNAc termini, albeit with low efficiency.

When used the glycolipids as acceptor substrates, the preferred one for the ST3 enzyme (SEQ. ID. NO:12) is asialo-$G_{M1}$ with $G_{M1}$, and lacto-neotetraosylceramide (n$L_{c4}$) also serving as substrates, but to a lesser extent (Table 4). In addition, low but significant level incorporation was also observed on lactosylceramide (LacCer). In contrast, the ST30 enzyme acts on asialo-$G_{M1}$ and $G_{M1}$ well whereas all glycolipids, even lacto-neotetraosylceramide are quite poor acceptors for the ST3N enzyme (SEQ. ID. NO:12)

Linkage specificity analysis of the ST3 enzyme—Since the ST3 enzyme (SEQ. ID. NO:12) utilizes Galβ1,3GalNAc and Galβ1,4GlcNAc sequences but 2,3-sialylated oligosaccharides of them fail to serve as acceptor substrates, this enzyme is thought to be a α2,3-sialyltransferase. In order to confirm the linkage specificity of the product formed by ST3 enzyme, we used Newcastle disease virus sialidase which was known to exhibit strict specificity for hydrolysis of the NeuAcα2,3Gal linkage contained in glycoprotein oligosaccharides both N-linked to asparagine and O-linked to threonine or serine under condition that left oligosaccharides containing the NeuAcα2,6Gal and NeuAcα2,6GalNAc linkage intact. Each [$^{14}$C] NeuAc labeled α₁-acid glycoprotein was produced from the asialo-derivative using ST3, ST3N, and ST6N (SEQ. ID. NO:4) enzymes, respectively. Then, these labeled products were hydrolyzed with Newcastle disease virus sialidase. 83%, 82% and 0% of total [$^{14}$C] NeuAc were released from ST3, ST3N and ST6N products, respectively. This result demonstrates that the sialylated product formed by ST3 enzyme has NeuAcα2,3Gal linkage and thus the ST3 enzyme is β-galactoside α2,3-sialyltransferase.

What is claimed is:

1. A synthetic enzyme which exhibits sialyltransferase activity, said enzyme comprising a catalytic domain, said catalytic domain comprising a conserved region having amino acid SEQ. ID. NO:28 and wherein the amino acid sequence of said conserved region is not SEQ. ID NO:14, SEQ. ID NO:15 or SEQ. ID. NO:16.

2. A synthetic enzyme according to claim 1 which further comprises a stem region.

3. A synthetic enzyme according to claim 2 which further comprises an amino terminal cytoplasmic domain.

4. A synthetic enzyme according to claim 3 which further comprises an amino terminal transmembrane domain.

* * * * *

UNITED STATES PATENT AND TRADEMARK OFFICE
CERTIFICATE OF CORRECTION

PATENT NO. : 5,962,294
DATED : October 5, 1999
INVENTOR(S) : PAULSON et al.

It is certified that error appears in the above-indentified patent and that said Letters Patent is hereby corrected as shown below:

On the cover sheet:

[73] Assignees: The Regents of the University of California, Oakland; Cytel Corporation, San Diego, both of Calif.

Signed and Sealed this

Twenty-ninth Day of August, 2000

Attest:

Q. TODD DICKINSON

Attesting Officer

Director of Patents and Trademarks